US006417338B1

(12) United States Patent
Stracke et al.

(10) Patent No.: US 6,417,338 B1
(45) Date of Patent: Jul. 9, 2002

(54) AUTOTAXIN: MOTILITY STIMULATING PROTEIN USEFUL IN CANCER DIAGNOSIS AND THERAPY

(75) Inventors: Mary Stracke, Rockville; Lance Liotta, Potomac; Elliott Schiffman, Chevy Chase; Henry Krutzch, Bethesda, all of MD (US); Jun Murata, Akita (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/483,831

(22) Filed: Jan. 17, 2000

Related U.S. Application Data

(63) Continuation of application No. 08/977,221, filed on Nov. 24, 1997, now Pat. No. 6,084,069, which is a division of application No. 08/364,455, filed on Dec. 27, 1994, now abandoned, which is a continuation-in-part of application No. 08/249,182, filed on May 25, 1994, now abandoned, which is a continuation-in-part of application No. 07/822,043, filed on Jan. 17, 1992, now Pat. No. 5,449,753.

(51) Int. Cl.$^7$ ................................................. A23J 1/00

(52) U.S. Cl. ...................... 530/412; 530/412; 530/350; 530/330; 530/326; 530/324; 435/69.1; 435/7.92; 536/23.1; 536/23.5

(58) Field of Search ............................. 435/69.1, 7.92; 536/23.1, 23.5; 530/350, 330, 326, 324, 412

(56) References Cited

U.S. PATENT DOCUMENTS 5,449,753 A * 9/1995 Stracke et al. ............... 530/326

OTHER PUBLICATIONS

Stracke et al., "Identification, Purification and Partial Sequence Analysis of Autotaxin, a Novel Motility–stimulating protein", Journal of Biological Chemistry, vol. 267 (4) pp. 2524–2529, Feb. 1992.*
Murata et al., "cDNA Cloning of the human tumor motility–stimulating protein, autotaxin, reveals a homology with phosphodiesterases", Journal of Biological Chemistry, vol. 269 (48), pp. 30479–30484, Dec. 1994.*
M. Narita, et al., "Molecular Cloning, Expression, and Localization of a Brain–Specific Phosphodiesterase I/Nucleotide Pyrophoasphatase (PD–Iα) From Rat Brain," *The Journal of Biological Chemistry*, 1994, pp. 28235–28242.
R. M. Warn, et al, "Motility Factors on the March," *Nature*, vol. 340, Jul. 20, 1989, pp. 186–187.
M. Stoker, et al. "Scatter Factor is a Fibroblast–Derive Modulator of Epithelial Cell Motility," *Nature*, vol. 327, May 1987, pp. 239–242.
B. Alberts, et al. "Molecular Biology of the Cell," Garland Publishing, Inc. (1983).
K. Yoshida, et al. "Studies On The Mechanisms of Invasion in Cancer. I. Isolation and Purification of a Factor Chemotactic For Cancer Cells," *Int. J. Cancer*, 1970, pp. 123–132.
M. Narita, et al., "Molecular Cloning, Expression, and Localization of a Brain–Specific Phosphodiesterase I/Nucleotide Pyrophoasphatase (PD–Iα) From Rat Brain," *The Journal of Biological Chemistry*, 1994, pp. 28235–28242.
M. L. Stracke, et al., "Identification, Purification, and Partial Sequence Analysis of Autotaxin, a Novel Motility–stimulating Protein", *The Journal of Biological Chemistry*, vol. 267, Feb. 5, 1992, No. 4, 1992, pp. 2524–2529.
H. Watanabe, et al. "Purification of Human Tumor Cell Autocrine Motility Factor and Molecular Cloning of Its Receptor," *The Journal of Biological Chemistry*, vol. 20, Jul. 15, 1991, pp. 13442–13448.
S. Silletti, et al. "Purification of B16–F1 Melanoma Autocrine Motility Factor and Its Receptor," *Cancer Research*, Jul. 1, 1991, pp. 3507–3511.
T. Ohnishi, et al. "Motility Factor Produced By Malignant Glioma Cells: Role in Tumor Invasion," *J. Neurosurg.*, vol. 73, Dec. 1990, pp. 881–888.
K. Michael Weidner, et al., "Scatter Factor: Molecular Characteristics and Effect on the Invasiveness of Epithelial Cells," *The Journal of Cellular Biology*, vol. 111, Nov. 1990, pp. 2097–2108.
E. M. Rosen, et al. "Purified Scatter Factor Stimulates Epithelial and Vascular Endothelial Cell Migration," *Society for Experimental Biology and Medicine*, Copyright 1990, pp. 34–43.
R. M. Warn, et al, "Motility Factors on the March," *Nature*, vol. 340, Jul. 20, 1989, pp. 186–187.
E. Gherardi et al., "Purification of Scatter Factor, a Fibroblast–Derived Basic Protein That Modulates Epithelial Interactions and Movement," *Proc. Natl. Acad. Sci.*, vol. 86, Aug. 1989, pp. 5844–5848.
M. L. Stracke, et al., "The Type Insulin–Like Growth Factor Receptor Is A Motility Receptor in Human Melanoma Cells," *The Journal of Biological Chemistry*, vol. 264, Dec. 25, 1989, pp. 21544–21549.
S. L. Schor, et al., "Foetal and Cancer Patient Fibroblasts Produce an Autocrine Migration–Stimulating Factor Not Made by Normal Adult Cells," *Journal of Cell Science*, 1988, pp. 391–399.

(List continued on next page.)

Primary Examiner—Karen Cochrane Carlson
Assistant Examiner—Hope A. Robinson
(74) Attorney, Agent, or Firm—Morgan & Finnegan, L.L.P.; William S. Feiler; Dorothy R. Auth

(57) ABSTRACT

The present invention relates, in general, to autotaxin. In particular, the present invention relates to a DNA segment encoding autotaxin; recombinant DNA molecules containing the DNA segment; cells containing the recombinant DNA molecule; a method of producing autotaxin; antibodies to autotaxin; and identification of functional domains in autotaxin.

4 Claims, 16 Drawing Sheets

OTHER PUBLICATIONS

K. D. Atnip, et al. "Chemotactic Reponse of Rat Mammary Adenocarcinoma Cell Clones to Tumor–Derived Cytokines," *Biochemical and Biophysical Research Communications*, vol. 146, Aug. 14, 1987, pp. 996–1002.

M. Stoker, et al. "Scatter Factor is a Fibroblast–Derive Modulator of Epithelial Cell Motility," *Nature*, vol. 327, May 1987, pp. 239–242.

L. A. Liotta, et al. "Tumor Cell Autocrine Motility Factor," *Proc. Natl. Acad. Sci.*, vol. 83, May 1986, pp. 3302–3306.

S. J. Singer, et al. "The Directed Migration of Eukaryotic Cells," *Ann. Rev, Cell Biol.*, pp. 337–362.

I. R. Nabi, et al. "Identification of B16–F1 Melanoma Autocrine Motility–Like Factor Receptor," *Cancer Research*, Jan. 15, 1990, pp. 409–414.

B. Alberts, et al. "Molecular Biology of the Cell," Garland Publishing, Inc.

G. J. Todaro, et al. Transforming Growth Factors produced by Certain Human Tumor Cells: Polypeptides That Interact With Epidermal Growth Factor Receptors, *Proc. Natl. Acad. Sci.*, vol. 77, No. 9, Sep. 1990, pp. 5258–5262.

K. Yoshida, et al. "Studies On The Mechanisms of Invasion in Cancer. I. Isolation and Purification of a Factor Chemotactic For Cancer Cells," *Int. J. Cancer*, pp. 123–132.

J. Murata, et al., "cDNA Cloning of the Human Tumor Motility–stimulating Protein, Autotaxin, Reveals a Homology with Phosphodiesterases", *The Journal of Biological Chemistry*, vol. 269, No. 48, Dec. 2, 1994 pp. 30479–30484.

\* cited by examiner

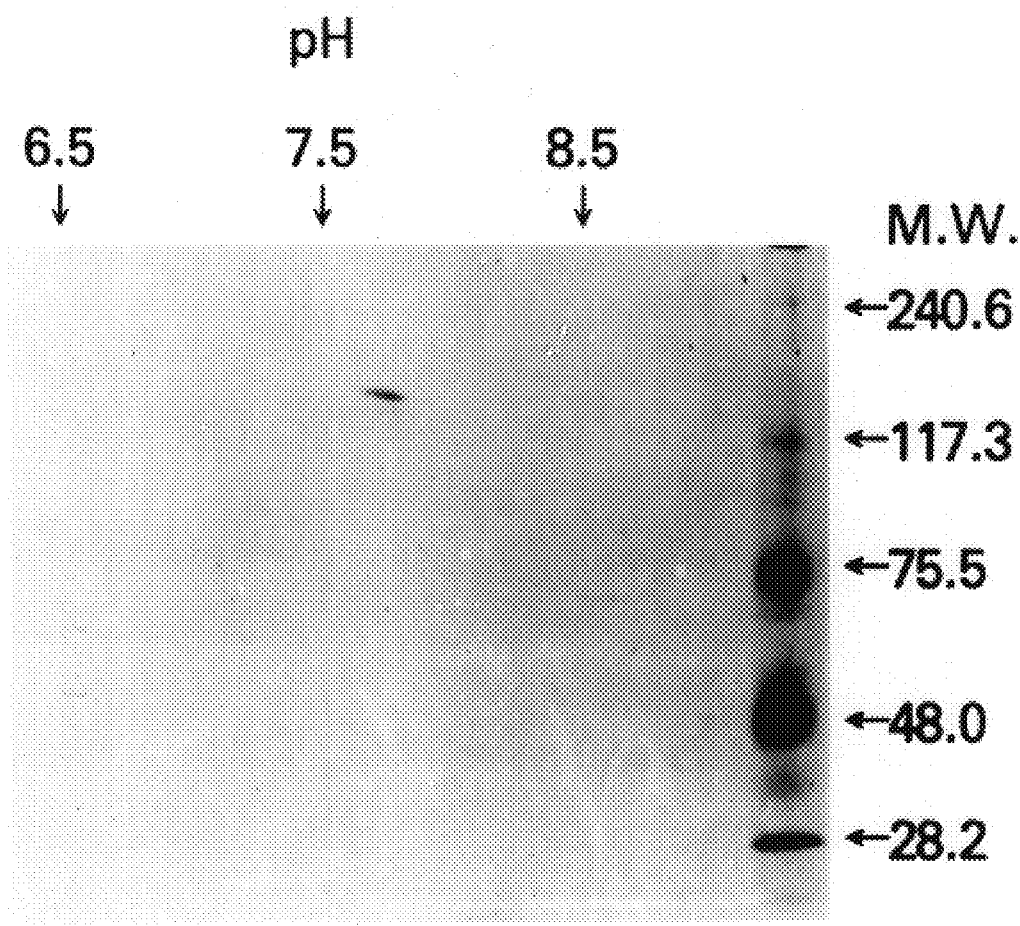

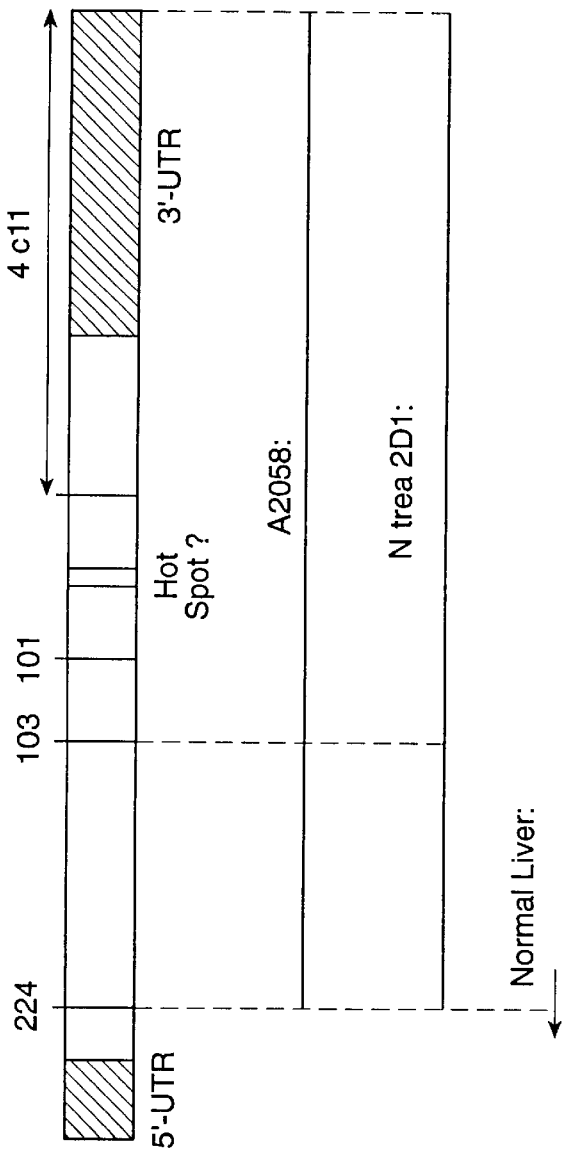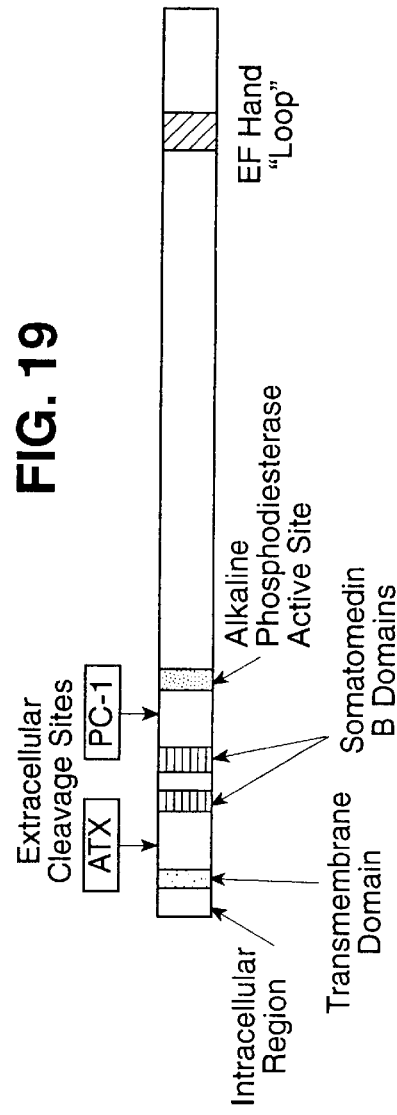

←—125 kDa

FIG. 18A

```
hATX    MARRSFQSCQIISLFTFAVGVSICLGFTAHRIKRAEGWEEGPPTVLSDSPWTNISGSCKGRCFELQEAGPPDCRCDNLCKSYTSCCHDF    90 hPC1    MDVGEEPLEKAAARTAKDPNTYKVLSLVLSVCVLTTIL........GCIFG....LKPSCAKEVK.SCKGRCF...ERTFGNCRCDAACVELGHCCLDY   84 hATX    DELCLKTARGWECTKDRCGEVRNEENACHCSEDCLARGDCCTNYQVVCKGESHWDDDCEEIKAAECPAGFVRPPLIIFSVDGFRASYMKKGSKVMPNIE    190 hPC1    QETCIEPEHIWTCNKFRCGEKRLTRSLCACSDDCKDKGDCCINYSSVCQGEKSWVEEPCESINEPQCPAGFETPPTLLFSLDGFRAEYLHTWGGLLPVIS   184 hATX    KLRSCGTHSPYMRPVYPTKTFPNLYTLATGLYPESHGIVGNSMYDPVFDATFHLRGREKFNHRWGGQPLWITATKQGVKAGTFFWS............   272 hPC1    KLKKCGTYTKNMRPVYPTKTFPNHYSIVTGLYPESHGIIDNKMYDPKMNASFSLKSKEKFNPEWYKGEPIWTAKYQGLKSGTFFWPGSDVEINGIFPDI   284 hATX    ....VVIPHERRILTIILRWLTLPDHERPSVYAFYSEQPDFSGHKYGPFGPEESSYGSPFTPAKRPKRKVAPKRQERPVAPPKKRRKIHRMDHYAAET   372 hPC1    YKMYNGSVPFEERILAVLQWLQLPKDERPHFYTLYLEEPDSSGHSYGPVSSE.............................................   336 hATX    RQDKMTNPLREIDKIVGQLMDGLKQLKLRRCVNIFVGDHGMEDVTCDRTEFLSNVLTNVDDITLVPGTLGRIR.SKFSNN.AKYDPKAIIANLTCKKPD   470 hPC1    ....VIKALQRVDGMVGMLMDGLKELNLHRCLNLILTSDHGMEQGSCKKYIYLNKYLGDVKNIKVIYGPAARLRPSDVPDKYYSPNYEGIARNLSCREPN   432 hATX    QHFKPYLKQHLPKRLHYANNRRIEDIHLLVERRWHVARKPLDVYKKPSGKCFFQGDHGFDNKVNSMQTVPVGYGPTFKYKTKVPPFENIELYNVMCDLIG   570 hPC1    QHFKPYLKHGLPKRLHFAKSDRIEPLTFYLDPQWQLALNPSE....HGSDNVFSNMQALFVGYGPFKHGIEADTFENIEVYNLMCDLLN   526
```

FIG. 18B

```
hATX   LKPAPNNGTHGSLNHLLRTNTFRPTMPEEVTRPNYPGIMYLQSDFDLGCTCDDKVEPKNKLD.ELNKRLHTKGSTEERHLLYGRPAVLYRTR.YDILYHT  668
           ||||||||||||  |  |   |    |||||   |    |      |||   |      |||||  ||  ||       |    
hPC1   LTPAPNNGTHGSLNHLLKNPVYTPKHPKEV.HPLVQCPFTRNPRDNLGCSCNPSILPIEDFQTQFNLTVAEEKIIKHETLPYGRPRVLQKENTICLLSQH  625 hATX   DFESGYSEIFLMLLWTSYTVSKQAEVSSVPDHLTSCVRPDVRVSPSFSQNCLAYKNDKQMSYGFLFPPYLSSSPEAKY.DAFLVTNMVPMYPAFKRVWNY  767
        |||  ||||  ||||||||  |   |||   || ||     |||  |||     ||    ||  |  ||   |    ||  ||||||     |  
hPC1   QFMSGYSQDILMPLWTSYTVDRNDSFS..TEDFSNCLYQDFRIPLSPVHKCSFYKNNTKVSYGFLSPPQLNKNSSGIYSEALLTTNIVPMYQSFQVIWRY  723 hATX   FQRVLVKKYASERNGVNNISGPIFDYDYDGLHDTEDKIKQ...YVEGSSIPVPTHYYSIITSCLDFTQPADKCDGPLSVSSFILPHRPDNEESCNSSEDE  875
        |   ||   ||||||   |||||||||| |||||||         ||||||  |    ||||| |    |  ||||  |||||| |  |||  |||
hPC1   FHDTLLRKYAEERNGVNVVSGPVFDFDYDGRCDSLENLRQKRRVIRNQEILIPTHFFIVLTSCKDTSQTPLHCEN.LDTLAFILPHRTDNSESCVHGKHD  822 hATX   SKWVEELMKMHTARVRDIEHLTSLDFFRKTSRSYPEILTLKTYLHTYESEI  915
         |||||| |    |  |||  |   ||        |  ||    |  ||
hPC1   SSWVEELLMLHRARITDVEHITGLSFYQQRKEPVSDILKLKTHLPTFSQED  873
```

SEQUENCE LISTING

```
<160> NUMBER OF SEQ ID NOS: 70

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 1

Trp His Val Ala Arg
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 2

Pro Leu Asp Val Tyr Lys
  1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 3

Tyr Pro Ala Phe Lys
  1               5

<210> SEQ ID NO 4
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Gln Ala Glu Val Ser
  1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Pro Glu Glu Val Thr Arg Pro Asn Tyr Leu
  1               5                  10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Tyr Asp Val Pro Trp Asn Glu Thr Ile
  1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Val Pro Pro Phe Glu Asn Ile Glu Leu Tyr
  1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gly Gly Gln Pro Leu Trp Ile Thr Ala Thr Lys
  1               5                  10

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Val Asn Ser Met Gln Thr Val Phe Val Gly Tyr Gly Pro Thr Phe Lys
```

```
                 1               5              10              15
```

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Asp Ile Glu His Leu Thr Ser Leu Asp Phe Phe Arg
 1               5                  10

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Thr Glu Phe Leu Ser Asn Tyr Leu Thr Asn Val Asp Asp Ile Thr Leu
 1               5                  10                  15

Val Pro Glu Thr Leu Gly Arg
            20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (10)
<223> OTHER INFORMATION: Base n represents a or g or c or t/u, unknown,
      or other.
<221> NAME/KEY: variation
<222> LOCATION: (13)
<223> OTHER INFORMATION: Base r represents g or a.

<400> SEQUENCE: 12
gttggcagcn acrtgcca                                                   18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (6)
<223> OTHER INFORMATION: Base Y represents  t/u or c.
<221> NAME/KEY: variation
<222> LOCATION: (9)
<223> OTHER INFORMATION: Base n represents a or g or c or t/u, unknown,
      or other.

<400> SEQUENCE: 13
tggcaygtng ctgccaac                                                   18

<210> SEQ ID NO 14
<211> LENGTH: 15
<212> TYPE: DNA
<213> ORGANISM: Artificial Sequence
<220> FEATURE:

```
<223> OTHER INFORMATION: Description of Artificial Sequence:  Synthetic
      Primers

<400> SEQUENCE: 14
cttgaaggca gggta                                                     15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (3)
<223> OTHER INFORMATION: Base y  represents t/u or c.
<221> NAME/KEY: variation
<222> LOCATION: (9)
<223> OTHER INFORMATION: Base n represents a or g or c or t/u, unknown,
      or other.
<221> NAME/KEY: variation
<222> LOCATION: (12)
<223> OTHER INFORMATION: Base y  represents  t/u or c.

<400> SEQUENCE: 15
taycctgcnt tyaag                                                     15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (4)
<223> OTHER INFORMATION: Base n represents a or g or c or t/u, unknown,
      or other.
<221> NAME/KEY: variation
<222> LOCATION: (7)
<223> OTHER INFORMATION: Base y  represents t/u or c.
<221> NAME/KEY: variation
<222> LOCATION: (10)
<223> OTHER INFORMATION: Base y  represents  t/u or c.

<400> SEQUENCE: 16
ggtnacytcy tcagg                                                     15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (12)
<223> OTHER INFORMATION: Base n represents a or g or c or t/u, unknown,
      or other.
<221> NAME/KEY: variation
<222> LOCATION: (6)
<223> OTHER INFORMATION: Base r represents a or g.
<221> NAME/KEY: variation
<222> LOCATION: (9)
<223> OTHER INFORMATION: Base r represents a or g.

<400> SEQUENCE: 17
cctgargarg tnacc                                                     15

<210> SEQ ID NO 18
<211> LENGTH: 21
```

```
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (1)
<223> OTHER INFORMATION: Base n represents a or g or c or t/u, unknown,
      or other.
<221> NAME/KEY: variation
<222> LOCATION: (4)
<223> OTHER INFORMATION: Base n represents a or g or c or t/u, unknown,
      or other.
<221> NAME/KEY: variation
<222> LOCATION: (7)
<223> OTHER INFORMATION: Base r  represents a or g.
<221> NAME/KEY: variation
<222> LOCATION: (10)
<223> OTHER INFORMATION: Base r  represents a or g.
<221> NAME/KEY: variation
<222> LOCATION: (19)
<223> OTHER INFORMATION: Base r  represents a or g.

<400> SEQUENCE: 18
ngtngcrtcr aatggcacrt c                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (3)
<223> OTHER INFORMATION: Base y represents t/u or c.
<221> NAME/KEY: variation
<222> LOCATION: (12)
<223> OTHER INFORMATION: Base y represents t/u or c.
<221> NAME/KEY: variation
<222> LOCATION: (15)
<223> OTHER INFORMATION: Base y  represents t/u or c.
<221> NAME/KEY: variation
<222> LOCATION: (18)
<223> OTHER INFORMATION: Base n represents a or g or c or t/u, unknown,
      or other.
<221> NAME/KEY: variation
<222> LOCATION: (21)
<223> OTHER INFORMATION: Base n represents a or g or c or t/u, unknown,
      or other.

<400> SEQUENCE: 19
gaygtgccat tygaygcnac n                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (4)
<223> OTHER INFORMATION: Base d represents a or g or t/u.
<221> NAME/KEY: variation
<222> LOCATION: (7)
<223> OTHER INFORMATION: Base r  represents a or g.
<221> NAME/KEY: variation
<222> LOCATION: (10)
<223> OTHER INFORMATION: Base s  represents g or c.
<221> NAME/KEY: variation
<222> LOCATION: (13)
<223> OTHER INFORMATION: Base r  represents a or g.

<400> SEQUENCE: 20
```
gttdatrtts tcraatgggg g                                                  21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primers

<400> SEQUENCE: 21
cccccatttg agaacatcaa c                                                  21

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (4)
<223> OTHER INFORMATION: Base n represents a or g or c or t/u, unknown,
      or other.
<221> NAME/KEY: variation
<222> LOCATION: (7)
<223> OTHER INFORMATION: Base n represents a or g or c or t/u, unknown,
      or other.
<221> NAME/KEY: variation
<222> LOCATION: (10)
<223> OTHER INFORMATION: Base n represents a or g or c or t/u, unknown,
      or other.
<221> NAME/KEY: variation
<222> LOCATION: (13)
<223> OTHER INFORMATION: Base d represents a or g or t/u.
<221> NAME/KEY: variation
<222> LOCATION: (19)
<223> OTHER INFORMATION: Base n represents a or g or c or t/u, unknown,
      or other.
<221> NAME/KEY: variation
<222> LOCATION: (21)
<223> OTHER INFORMATION: Base r  represents a or g.
<221> NAME/KEY: variation
<222> LOCATION: (25)
<223> OTHER INFORMATION: Base y  represents c or t/u.

<400> SEQUENCE: 22
cttngtngcn gtdatccana rgggytggcc gcc                                     33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primers
<221> NAME/KEY: variation
<222> LOCATION: (9)
<223> OTHER INFORMATION: Base r represents a or g.
<221> NAME/KEY: variation
<222> LOCATION: (13)
<223> OTHER INFORMATION: Base y represents c or t/u.
<221> NAME/KEY: variation
<222> LOCATION: (15)
<223> OTHER INFORMATION: Base n represents a or g or c or t/u, unknown,
      or other.
<221> NAME/KEY: variation
<222> LOCATION: (21)
<223> OTHER INFORMATION: Base h  represents a or  c or t/u.
<221> NAME/KEY: variation
<222> LOCATION: (24)
<221> NAME/KEY: variation
<222> LOCATION: (27)

```
<223> OTHER INFORMATION: Base n represents a or g or c or t/u, unknown,
      or other.
<221> NAME/KEY: variation
<222> LOCATION: (30)
<223> OTHER INFORMATION: Base n represents a or g or c or t/u, unknown,
      or other.

<400> SEQUENCE: 23
ggcggccarc ccytntggat hacngcnacn aag                                33

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      Primers
<221> NAME/KEY: variation
<222> LOCATION: (4)
<223> OTHER INFORMATION: Base r  represents a or g.
<221> NAME/KEY: variation
<222> LOCATION: (16)
<223> OTHER INFORMATION: Base r  represents a or g.
<221> NAME/KEY: variation
<222> LOCATION: (25)
<223> OTHER INFORMATION: Base r represents a or g.
<221> NAME/KEY: variation
<222> LOCATION: (34)
<223> OTHER INFORMATION: Base y  represents c or t/u.

<400> SEQUENCE: 24
cttraaggtg gggccrtagc ccacraagac tgtytgcat                          39

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      Primers
<221> NAME/KEY: variation
<222> LOCATION: (6)
<223> OTHER INFORMATION: Base r  represents a or g.
<221> NAME/KEY: variation
<222> LOCATION: (15)
<223> OTHER INFORMATION: Base y represents c or t/u.
<221> NAME/KEY: variation
<222> LOCATION: (24)
<223> OTHER INFORMATION: Base y  represents c or t/u.
<221> NAME/KEY: variation
<222> LOCATION: (36)
<223> OTHER INFORMATION: Base y  represents c or t/u.
<221> NAME/KEY: variation
<222> LOCATION: (39)
<223> OTHER INFORMATION: Base r  represents a or g.

<400> SEQUENCE: 25
atgcaracag tcttygtggg ctayggcccc accttyaar                          39

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Gln Tyr Leu His Gln Tyr Gly Ser Ser
 1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Val Leu Asn Tyr Phe
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Tyr Leu Asn Ala Thr
 1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

His Leu Leu Tyr Gly Arg Pro Ala Val Leu Tyr
 1               5                  10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Ser Tyr Pro Glu Ile Leu Thr Pro Ala Asp Asn
 1               5                  10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide
<221> NAME/KEY: CARBOHYD
<222> LOCATION: (1)
<223> OTHER INFORMATION: X refers to potentially glycosylated residues.

<400> SEQUENCE: 31

Xaa Tyr Gly Phe Leu Phe Pro Pro Tyr Leu Ser Ser Ser Pro
 1               5                  10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
```

Peptide

<400> SEQUENCE: 32

Thr Phe Pro Asn Leu Tyr Thr Phe Ala Thr Gly Leu Tyr
1               5                  10

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Val Asn Val Ile Ser Gly Pro Ile Asp Asp Tyr Asp Tyr Asp Gly Leu
1               5                   10                  15

His Asp Thr Glu Asp Lys
            20

<210> SEQ ID NO 34
<211> LENGTH: 829
<212> TYPE: PRT
<213> ORGANISM: Homo sapiens
<220> FEATURE:
<223> OTHER INFORMATION: Putative protein sequence of A2058 Autotoxin

<400> SEQUENCE: 34

Cys His Asp Phe Asp Glu Leu Cys Leu Lys Thr Ala Arg Gly Trp Glu
1               5                   10                  15

Cys Thr Lys Asp Arg Cys Gly Glu Val Arg Asn Glu Glu Asn Ala Cys
            20                  25                  30

His Cys Ser Glu Asp Cys Leu Ala Arg Gly Asp Cys Cys Thr Asn Tyr
        35                  40                  45

Gln Val Val Cys Lys Gly Glu Ser His Trp Val Asp Asp Cys Glu
    50                  55                  60

Glu Ile Lys Ala Ala Glu Cys Pro Ala Gly Phe Val Arg Pro Pro Leu
65                  70                  75                  80

Ile Ile Phe Ser Val Asp Gly Phe Arg Ala Ser Tyr Met Lys Lys Gly
                85                  90                  95

Ser Lys Val Met Pro Asn Ile Glu Lys Leu Arg Ser Cys Gly Thr His
            100                 105                 110

Ser Pro Tyr Met Arg Pro Val Tyr Pro Thr Lys Thr Phe Pro Asn Leu
        115                 120                 125

Tyr Thr Leu Ala Thr Gly Leu Tyr Pro Glu Ser His Gly Ile Val Gly
    130                 135                 140

Asn Ser Met Tyr Asp Pro Val Phe Asp Ala Thr Phe His Leu Arg Gly
145                 150                 155                 160

Arg Glu Lys Phe Asn His Arg Trp Trp Gly Gly Gln Pro Leu Trp Ile
                165                 170                 175

Thr Ala Thr Lys Gln Gly Val Lys Ala Gly Thr Phe Phe Trp Ser Val
            180                 185                 190

Val Ile Pro His Glu Arg Arg Ile Leu Thr Ile Leu Arg Trp Leu Thr
        195                 200                 205

Leu Pro Asp His Glu Arg Pro Ser Val Tyr Ala Phe Tyr Ser Glu Gln
    210                 215                 220

Pro Asp Phe Ser Gly His Lys Tyr Gly Pro Phe Gly Pro Glu Glu Ser
225                 230                 235                 240

-continued

```
Ser Tyr Gly Ser Pro Phe Thr Pro Ala Lys Arg Pro Lys Arg Lys Val
                245                 250                 255

Ala Pro Lys Arg Arg Gln Glu Arg Pro Val Ala Pro Lys Lys Arg
            260                 265                 270

Arg Arg Lys Ile His Arg Met Asp His Tyr Ala Ala Glu Thr Arg Gln
            275                 280                 285

Asp Lys Met Thr Asn Pro Leu Arg Glu Ile Asp Lys Ile Val Gly Gln
290                 295                 300

Leu Met Asp Gly Leu Lys Gln Leu Lys Leu Arg Arg Cys Val Asn Val
305                 310                 315                 320

Ile Phe Val Gly Asp His Gly Met Glu Asp Val Thr Cys Asp Arg Thr
                325                 330                 335

Glu Phe Leu Ser Asn Tyr Leu Thr Asn Val Asp Asp Ile Thr Leu Val
                340                 345                 350

Pro Gly Thr Leu Gly Arg Ile Arg Ser Lys Phe Ser Asn Asn Ala Lys
                355                 360                 365

Tyr Asp Pro Lys Ala Ile Ile Ala Asn Leu Thr Cys Lys Lys Pro Asp
            370                 375                 380

Gln His Phe Lys Pro Tyr Leu Lys Gln His Leu Pro Lys Arg Leu His
385                 390                 395                 400

Tyr Ala Asn Asn Arg Arg Ile Glu Asp Ile His Leu Leu Val Glu Arg
                405                 410                 415

Arg Trp His Val Ala Arg Lys Pro Leu Asp Val Tyr Lys Lys Pro Ser
                420                 425                 430

Gly Lys Cys Phe Phe Gln Gly Asp His Gly Phe Asp Asn Lys Val Asn
            435                 440                 445

Ser Met Gln Thr Val Phe Val Gly Tyr Gly Pro Thr Phe Lys Tyr Lys
            450                 455                 460

Thr Lys Val Pro Pro Phe Glu Asn Ile Glu Leu Tyr Asn Val Met Cys
465                 470                 475                 480

Asp Leu Leu Gly Leu Lys Pro Ala Pro Asn Asn Gly Thr His Gly Ser
                485                 490                 495

Leu Asn His Leu Leu Arg Thr Asn Thr Phe Arg Pro Thr Met Pro Glu
            500                 505                 510

Glu Val Thr Arg Pro Asn Tyr Pro Gly Ile Met Tyr Leu Gln Ser Asp
            515                 520                 525

Asp Asp Leu Gly Cys Thr Cys Asp Asp Lys Val Glu Pro Lys Asn Lys
530                 535                 540

Leu Asp Glu Leu Asn Lys Arg Leu His Thr Lys Gly Ser Thr Glu Glu
545                 550                 555                 560

Arg His Leu Leu Tyr Gly Arg Pro Ala Val Leu Tyr Arg Thr Arg Tyr
                565                 570                 575

Asp Ile Leu Tyr His Thr Asp Phe Glu Ser Gly Tyr Ser Glu Ile Phe
                580                 585                 590

Leu Met Leu Leu Trp Thr Ser Tyr Thr Val Ser Lys Gln Ala Glu Val
            595                 600                 605

Ser Ser Val Pro Asp His Leu Thr Ser Cys Val Arg Pro Asp Val Arg
            610                 615                 620

Val Ser Pro Ser Phe Ser Gln Asn Cys Leu Ala Tyr Lys Asn Asp Lys
625                 630                 635                 640

Gln Met Ser Tyr Gly Phe Leu Phe Pro Pro Tyr Leu Ser Ser Ser Pro
                645                 650                 655

Glu Ala Lys Tyr Asp Ala Phe Leu Val Thr Asn Met Val Pro Met Tyr
```

-continued

```
            660                 665                 670

Pro Ala Phe Lys Arg Val Trp Asn Tyr Phe Gln Arg Val Leu Val Lys
        675                 680                 685

Lys Tyr Ala Ser Glu Arg Asn Gly Val Asn Val Ile Ser Gly Pro Ile
    690                 695                 700

Phe Asp Tyr Asp Tyr Asp Gly Leu His Asp Thr Glu Asp Lys Ile Lys
705                 710                 715                 720

Gln Tyr Val Glu Gly Ser Ser Ile Pro Val Pro Thr His Tyr Tyr Ser
                725                 730                 735

Ile Ile Thr Ser Cys Leu Asp Phe Thr Gln Pro Ala Asp Lys Cys Asp
            740                 745                 750

Gly Pro Leu Ser Val Ser Ser Phe Ile Leu Pro His Arg Pro Asp Asn
        755                 760                 765

Glu Glu Ser Cys Asn Ser Ser Glu Asp Glu Ser Lys Trp Val Glu Glu
    770                 775                 780

Leu Met Lys Met His Thr Ala Arg Val Arg Asp Ile Glu His Leu Thr
785                 790                 795                 800

Ser Leu Asp Phe Phe Arg Lys Thr Ser Arg Ser Tyr Pro Glu Ile Leu
                805                 810                 815

Thr Leu Lys Thr Tyr Leu His Thr Tyr Glu Ser Glu Ile
            820                 825
```

<210> SEQ ID NO 35
<211> LENGTH: 2946
<212> TYPE: DNA
<213> ORGANISM: Homo sapiens
<220> FEATURE:
<223> OTHER INFORMATION: Partial DNA sequence of A2058 Autotoxin

<400> SEQUENCE: 35

```
gctgccatga ctttgatgag ctgtgtttga agacagcccg tggctgggag tgtactaagg     60
acagatgtgg agaagtcaga aatgaagaaa atgcctgtca ctgctcagag gactgcttgg    120
ccaggggaga ctgctgtacc aattaccaag tggtttgcaa aggagagtcg cattgggttg    180
atgatgactg tgaggaaata aaggccgcag aatgccctgc agggtttgtt cgccctccat    240
taatcatctt ctccgtggat ggcttccgtg catcatacat gaagaaaggc agcaaagtca    300
tgcctaatat tgaaaaacta aggtcttgtg gcacacactc tccctacatg aggccggtgt    360
acccaactaa aacctttcct aacttataca ctttggccac tggggctatat ccagaatcac    420 atggaattgt tggcaattca atgtatgatc ctgtatttga tgccactttt catctgcgag    480
ggcgagagaa atttaatcat agatggtggg gaggtcaacc gctatggatt acagccacca    540
agcaaggggt gaaagctgga acattctttt ggtctgttgt catccctcac gagcggagaa    600
tattaaccat attgcggtgg ctcaccctgc cagatcatga gaggccttcg gtctatgcct    660
tctattctga gcaacctgat ttctctggac acaaatatgg ccctttcggc cctgaggaga    720
gtagttatgg ctcacctttt actccggcta agagacctaa gaggaaagtt gcccctaaga    780
ggagacagga aagaccagtt gctcctccaa agaaaagaag aagaaaaata cataggatgg    840
atcattatgc tgcggaaact cgtcaggaca aaatgacaaa tcctctgagg gaaatcgaca    900
aaattgtggg gcaattaatg gatggactga aacaactaaa actgcgtcgg tgtgtcaacg    960
tcatctttgt cggagaccat ggaatggaag atgtcacatg tgatagaact gagttcttga   1020
gtaattacct aactaatgtg gatgatatta ctttagtgcc tggaactcta ggaagaattc   1080
gatccaaatt tagcaacaat gctaaatatg accccaaagc cattattgcc aatctcacgt   1140
```

```
gtaaaaaacc agatcagcac tttaagcctt acttgaaaca gcaccttccc aaacgtttgc   1200
actatgccaa caacagaaga attgaggata tccatttatt ggtggaacgc agatggcatg   1260
ttgcaaggaa acctttggat gtttataaga accatcagg aaaatgcttt ttccagggag    1320
accacggatt tgataacaag gtcaacagca tgcagactgt ttttgtaggt tatggcccaa   1380
catttaagta caagactaaa gtgcctccat ttgaaaacat tgaactttac aatgttatgt   1440
gtgatctcct gggattgaag ccagctccta ataatgggac ccatggaagt ttgaatcatc   1500
tcctgcgcac taataccttc aggccaacca tgccagagga agttaccaga cccaattatc   1560
cagggattat gtaccttcag tctgattttg acctgggctg cacttgtgat gataaggtag   1620
agccaaagaa caagttggat gaactcaaca acggcttca tacaaaaggg tctacagaag    1680
agagacacct cctctatggg cgacctgcag tgctttatcg gactagatat gatatcttat   1740
atcacactga ctttgaaagt ggttatagtg aaatattcct aatgctactc tggacatcat   1800
atactgtttc caaacaggct gaggtttcca gcgttcctga ccatctgacc agttgcgtcc   1860
ggcctgatgt ccgtgtttct ccgagtttca gtcagaactg tttggcctac aaaaatgata   1920
agcagatgtc ctacggattc ctctttcctc cttatctgag ctcttcacca gaggctaaat   1980
atgatgcatt ccttgtaacc aatatggttc caatgtatcc tgctttcaaa cgggtctgga   2040
attatttcca agggtattg gtgaagaaat atgcttcgga agaaatgga gttaacgtga     2100 taagtggacc aatcttcgac tatgactatg atggcttaca tgacacagaa gacaaaataa   2160
aacagtacgt ggaaggcagt tccattcctg ttccaactca ctactacagc atcatcacca   2220
gctgtctgga tttcactcag cctgccgaca gtgtgacgg ccctctctct gtgtcctcct    2280
tcatcctgcc tcaccggcct gacaaagagg agagctgcaa tagctcagag gacgaatcaa   2340
aatgggtaga agaactcatg aagatgcaca cagctagggt gcgtgacatt gaacatctca   2400
ccagcctgga cttcttccga aagaccagcc gcagctaccc agaaatcctg acactcaaga   2460
catacctgca tacatatgag agcgagattt aactttctga gcatctgcag tacagtctta   2520
tcaactggtt gtatattttt atattgtttt tgtatttatt aatttgaaac caggacatta   2580
aaaatgttag tattttaatc ctgtaccaaa tctgacatat tatgcctgaa tgactccact   2640
gtttttctct aatgcttgat ttaggtagcc ttgtgttctg agtagagctt gtaataaata   2700
ctgcagcttg agaaaaagtg gaagcttcta aatggtgctg cagatttgat atttgcattg   2760
aggaaatatt aattttccaa tgcacagttg ccacatttag tcctgtactg tatggaaaca   2820
ctgattttgt aaagttgcct ttatttgctg ttaactgtta actatgacag atatatttaa   2880
gccttataaa ccaatcttaa acataataaa tcacacattc agttttaaaa aaaaaaaaa    2940 aaaaaa                                                              2946
```

<210> SEQ ID NO 36
<211> LENGTH: 788
<212> TYPE: PRT
<213> ORGANISM: Homo sapiens
<220> FEATURE:
<223> OTHER INFORMATION: N-tera 2D1 putative ATX protein sequence

<400> SEQUENCE: 36

Cys Asp Asn Leu Cys Lys Ser Tyr Thr Ser Cys Cys His Asp Phe Asp
1               5                   10                  15

Glu Leu Cys Leu Lys Thr Ala Arg Ala Trp Glu Cys Thr Lys Asp Arg
            20                  25                  30

-continued

```
Cys Gly Glu Val Arg Asn Glu Glu Asn Ala Cys His Cys Ser Glu Asp
         35                  40                  45
Cys Leu Ala Arg Gly Asp Cys Cys Thr Asn Tyr Gln Val Val Cys Lys
         50                  55                  60
Gly Glu Ser His Trp Val Asp Asp Cys Glu Ile Lys Ala Ala
 65              70                  75                  80
Glu Cys Leu Gln Val Asp Ser Pro Ser Ile Asn His Leu Leu Arg Gly
                 85                  90                  95
Trp Leu Pro Met Thr Ser Tyr Met Lys Lys Gly Ser Lys Val Met Pro
             100                 105             110
Asn Ile Glu Lys Leu Arg Ser Cys Gly Thr His Ser Pro Tyr Met Arg
         115                 120             125
Pro Val Tyr Pro Thr Lys Thr Phe Pro Asn Leu Tyr Thr Leu Ala Thr
 130                 135                 140
Gly Leu Tyr Pro Glu Ser His Gly Ile Val Gly Asn Ser Met Tyr Asp
 145                 150                 155                 160
Pro Val Phe Asp Ala Thr Phe His Leu Arg Gly Arg Glu Lys Phe Asn
             165                 170                 175
His Arg Trp Trp Ala Gly Gln Pro Leu Trp Ile Thr Ala Thr Lys Gln
             180                 185                 190
Arg Gly Glu Ser Trp Asn Ile Leu Leu Val Cys His Pro Ser Arg
         195                 200                 205
Ala Glu Ile Leu Thr Ile Leu Gln Trp Leu Thr Leu Pro Asp His Glu
 210                 215                 220
Arg Pro Ser Val Tyr Ala Phe Tyr Ser Glu Gln Pro Asp Phe Ser Gly
 225                 230                 235                 240
His Lys His Met Pro Phe Gly Pro Glu Met Pro Asn Pro Leu Arg Glu
             245                 250                 255
Met His Lys Ile Val Gly Gln Leu Met Asp Gly Leu Lys Gln Leu Lys
             260                 265                 270
Leu His Arg Cys Val Asn Val Ile Phe Val Glu Thr Met Asp Gly Arg
         275                 280                 285
Cys His Met Tyr Arg Thr Glu Phe Leu Ser Asn Tyr Leu Thr Asn Val
 290                 295                 300
Asp Asp Ile Thr Leu Val Pro Gly Thr Leu Gly Arg Ile Arg Ser Lys
 305                 310                 315                 320
Phe Ser Asn Asn Ala Lys Tyr Asp Pro Lys Ala Ile Ile Ala Asn Leu
             325                 330                 335
Thr Cys Lys Lys Pro Asp Gln His Phe Lys Pro Tyr Leu Lys Gln His
             340                 345                 350
Leu Pro Lys Arg Leu His Tyr Ala Asn Asn Arg Arg Ile Glu Asp Ile
         355                 360                 365
His Leu Leu Val Glu Arg Arg Trp His Val Ala Arg Lys Pro Leu Asp
 370                 375                 380
Val Tyr Lys Lys Pro Ser Gly Asn Ala Phe Ser Arg Glu Thr Thr Ala
 385                 390                 395                 400
Phe Asp Asn Lys Val Asn Ser Met Gln Thr Val Phe Val Gly Tyr Gly
             405                 410                 415
Pro Thr Phe Lys Tyr Lys Thr Lys Val Pro Pro Phe Glu Asn Ile Glu
             420                 425                 430
Leu Tyr Asn Val Met Cys Asp Leu Leu Gly Leu Lys Pro Ala Pro Asn
         435                 440                 445
Asn Gly Thr His Phe Ser Leu Asn His Leu Leu Arg Thr Asn Thr Phe
```

```
            450             455             460
Arg Pro Thr Met Pro Glu Glu Val Thr Arg Pro Asn Tyr Pro Gly Ile
465             470             475             480

Met Tyr Leu Gln Ser Asp Phe Asp Leu Gly Cys Thr Cys Asp Asp Lys
            485             490             495

Val Glu Pro Lys Asn Lys Leu Asp Glu Leu Asn Lys Arg Leu His Thr
        500             505             510

Lys Gly Ser Thr Glu Glu Arg His Leu Leu Tyr Gly Asp Arg Pro Ala
        515             520             525

Val Leu Tyr Arg Thr Arg Tyr Asp Ile Leu Tyr His Thr Asp Phe Glu
        530             535             540

Ser Gly Tyr Ser Glu Ile Phe Leu Met Pro Leu Trp Thr Ser Tyr Thr
545             550             555             560

Val Ser Lys Gln Ala Glu Val Ser Ser Val Pro Asp His Leu Thr Ser
            565             570             575

Cys Val Arg Pro Asp Val Arg Val Ser Pro Ser Phe Ser Gln Asn Cys
            580             585             590

Leu Ala Tyr Lys Asn Asp Lys Gln Met Ser Tyr Gly Gly Leu Gly Pro
        595             600             605

Pro Tyr Leu Ser Ser Ser Pro Glu Ala Lys Tyr Asp Ala Phe Leu Val
        610             615             620

Thr Asn Met Val Pro Met Tyr Pro Ala Phe Lys Arg Val Trp Asn Tyr
625             630             635             640

Phe Gln Arg Val Leu Val Lys Lys Tyr Ala Ser Glu Arg Asn Gly Val
            645             650             655

Asn Val Ile Ser Gly Pro Ile Phe Asp Tyr Asp Tyr Asp Gly Leu His
            660             665             670

Asp Thr Glu Asp Lys Ile Lys Gln Tyr Val Glu Gly Ser Ser Ile Pro
        675             680             685

Val Pro Thr His Tyr Tyr Ser Ile Ile Thr Ser Cys Leu Asp Phe Thr
        690             695             700

Gln Pro Ala Asp Lys Cys Asp Gly Pro Leu Ser Val Ser Ser Phe Ile
705             710             715             720

Leu Pro His Arg Pro Asp Asn Glu Glu Ser Cys Asn Ser Ser Glu Asp
            725             730             735

Glu Ser Lys Trp Val Glu Glu Leu Met Lys Met His Thr Ala Arg Val
            740             745             750

Arg Asp Ile Glu His Leu Thr Ser Leu Asp Phe Phe Arg Lys Thr Ser
        755             760             765

Arg Ser Tyr Pro Glu Ile Leu Thr Leu Lys Thr Tyr Leu His Thr Tyr
        770             775             780

Glu Ser Glu Ile
785

<210> SEQ ID NO 37
<211> LENGTH: 2712
<212> TYPE: DNA
<213> ORGANISM: Homo sapiens
<220> FEATURE:
<223> OTHER INFORMATION: N-tera 2D1 ATX DNA sequence

<400> SEQUENCE: 37
tgtgacaact tgtgtaagag ctataccagt tgctgccatg actttgatga gctgtgtttg     60
aagacagccc gtgcgtggga gtgtactaag gacagatgtg gggaagtcag aaatgaagaa    120
```

-continued

| | |
|---|---|
| aatgcctgtc actgctcaga ggactgcttg gccaggggag actgctgtaa caattaccaa | 180 |
| gtggtttgca aaggagagtc gcattgggtt gatgatgact gtgaggaaat aaaggccgca | 240 |
| gaatgcctgc aggtttgttc gccctccatt aatcatcttc tccgtggatg gcttccgatg | 300 |
| acatcataca tgaagaaagg cagcaaagtc atgcctaata ttgaaaaact aaggtcttgt | 360 |
| ggcacacact ctccctacat gaggccggtg tacccaacta aaacctttcc taacttatac | 420 |
| actttggcca ctgggctata tccagaatca catggaattg ttggcaattc aatgtatgat | 480 |
| cctgtatttg atgccacttt tcatctgcga gggcgagaga aatttaatca tagatggtgg | 540 |
| ggaggtcaac cgctatggat tacagccacc aagcaaaggg gtgaaagctg aacattctt | 600 |
| ttggtctgtt gtcatccctc acgagcgag atattaacca tattgcagtg gctcaccctg | 660 |
| ccagatcatg agaggccttc ggtctatgcc ttctattctg agcaacctga tttctctgga | 720 |
| cacaaacata tgcctttcgg ccctgagatg acaaatcctc tgagggaaat gcacaaaatt | 780 |
| gtgggcaat taatggatgg actgaaacaa ctaaaactgc atcggtgtgt caacgtcatc | 840 |
| tttgtcgaga ccatggatgg aagatgtcac atgtatagaa ctgagttctt gagtaattac | 900 |
| ctaactaatg tggatgatat tactttagtg cctggaactc taggaagaat tcgatccaaa | 960 |
| tttagcaaca atgctaaata tcaccccaaa gccattattg ccaatctcac gtgtaaaaaa | 1020 |
| ccagatcagc actttaagcc ttacttgaaa cagcaccttc ccaaacgttt gcactatgcc | 1080 |
| aacaacagaa gaattgagga tatccattta ttggtggaac gcagatggca tgttgcaagg | 1140 |
| aaacctttgg atgtttataa gaaaccatca ggaaatgctt tttccaggga gaccacggca | 1200 |
| tttgataaca aggtcaacag catgcagact gtttttgtag gttatggccc aacatttaag | 1260 |
| tacaagacta aagtdcctcc atttgaaaac attgaacttt aaaatgttat gtgtgatctc | 1320 |
| ctgggattga agccagctcc taataatggg acccatggaa gtttgaatca tctcctgcgc | 1380 |
| actaatacct tcaggccaac catgccagag gaagttacca gacccatatta tccagggatt | 1440 |
| atgtaccttc agtctgattt tgacctgggc tgcacttgtg atgataaggt agagccaaag | 1500 |
| aacaagttgg atgaactcaa caacggctt catacaaaag ggtctacaga agagagacac | 1560 |
| ctcctctatg gggatcgacc tgcagtgctt tatcggacta gatatgatat cttatatcac | 1620 |
| actgactttg aaagtggtta tagtgaaata ttcctaatgc cactctggac atcatatact | 1680 |
| gtttccaaac aggctgaggt ttccagcgtt cctgaccatc tgaccagttg cgtccggcct | 1740 |
| gatgtccgtg tttctccgag tttcagtcag aactgtttgg cctacaaaaa tgataagcag | 1800 |
| atgtcctacg gattcctctt tcctccttat ctgagctctt caccagaggc taaatatgat | 1860 |
| gcattccttg taaccaatat ggttccaatg tatcctgctt tcaaacgggt ctggaattat | 1920 |
| ttccaaaggg tattggtgaa gaaatatgct tcggaaagaa atggagttaa cgtgataagt | 1980 |
| ggaccaatct tcgactatga ctatgatggc ttacatgaca cagaagacaa aataaaacag | 2040 |
| tacgtggaag gcagttccat tcctgttcca actcactact acagcatcat caccagctgt | 2100 |
| ctggatttca ctcagcctgc cgacaagtgt gacggccctc tctctgtgtc ctccttcatc | 2160 |
| ctgcctcacc ggcctgacaa cgaggagagc tgcaatagct cagaggacga atcaaaatgg | 2220 |
| gtagaagaac tcatgaagat gcacacagct agggtgcgtg acattgaaca tctccaccag | 2280 |
| ctggacttct tccgaaagac cagccgcagc tacccagaaa tcctgacact caagacatac | 2340 |
| ctgcatacat atgagagcga gatttaactt tctgagcatc tgcagtacag tcttatcaac | 2400 |
| tggttgtata tttttatatt gttttttgtat ttattaattt gaaaccagga cattaaaaat | 2460 |
| gttagtattt taatcctgta ccaaatctga catattatgc ctgaatgact ccactgtttt | 2520 |

```
tctctaatgc ttgatttagg tagccttgtg ttctgagtag agcttgtaat aaatactgca    2580
gcttgagttt ttagtggaag cttctaaatg gtgctgcaga tttgatattt gcattgagga    2640
aatattaatt ttccaatgca cagttgccac atttagtcct gtactgtatg gaaacactga    2700
ttttgtaaag tt                                                        2712
```

```
<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 38

Arg Val Trp Asn Tyr Phe Gln Arg
  1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 39

Met His Thr Ala Arg Val Arg Asp
  1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 40

Phe Ser Asn Asn Ala Lys Tyr Asp
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 41

Val Met Pro Asn Ile Glu Lys
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 42

Thr Ala Arg Gly Trp Glu Cys Thr
  1               5
```

```
<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide
<221> NAME/KEY: VARIANT
<222> LOCATION: (1)
<223> OTHER INFORMATION: Xaa represents either an unknown or any amino
      acid residue.
<221> NAME/KEY: VARIANT
<222> LOCATION: (7)

<400> SEQUENCE: 43

Xaa Asp Ser Pro Trp Thr Xaa Ile Ser Gly Ser
 1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 44

Leu Arg Ser Cys Gly Thr His Ser Pro Tyr Met
 1               5                  10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 45

Thr Tyr Leu His Thr Tyr Glu Ser
 1               5

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 46

Ala Ile Ile Ala Asn Leu Thr Cys Lys Lys Pro Asp Gln
 1               5                  10

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 47

Ile Val Gly Gln Leu Met Asp Gly
 1               5

<210> SEQ ID NO 48
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Thr Ser Arg Ser Tyr Pro Glu Ile Leu
 1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 49

Gln Ala Glu Val Ser Ser Val Pro Asp
 1               5

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 50

Arg Cys Phe Glu Leu Gln Glu Ala Gly Pro Pro Asp Asp Cys
 1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Ser Tyr Thr Ser Cys Cys His Asp Phe Asp Glu Leu
 1               5                   10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Gln Met Ser Tyr Gly Phe Leu Phe Pro Pro Tyr Leu Ser Ser Ser Pro
 1               5                   10                  15

<210> SEQ ID NO 53
<211> LENGTH: 117
<212> TYPE: DNA
<213> ORGANISM: Homo sapiens
<220> FEATURE:
<223> OTHER INFORMATION: 5' end of human liver ATX gene

<400> SEQUENCE: 53
atggcaagga ggagctcgtt ccagtcgtgt caagatatat ccctgttcac ttttgccgtt      60
```
ggagtcaata tctgcttagg attcactgca catcgaatta agagagcaga aggatgg        117

<210> SEQ ID NO 54
<211> LENGTH: 39
<212> TYPE: PRT
<213> ORGANISM: Homo sapiens
<220> FEATURE:
<223> OTHER INFORMATION: N-terminal region including transmembrane
      domain of liver ATX protein

<400> SEQUENCE: 54

Met Ala Arg Arg Ser Ser Phe Gln Ser Cys Gln Asp Ile Ser Leu Phe
 1               5                  10                  15

Thr Phe Ala Val Gly Val Asn Ile Cys Leu Gly Phe Thr Ala His Arg
             20                  25                  30

Ile Lys Arg Ala Glu Gly Trp
         35

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55
gctcagataa ggaggaaaga g                                               21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
gaatccgtag gacatctgct t                                               21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
tgtaggccaa acagttctga c                                               21

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer
<221> NAME/KEY: variation
<222> LOCATION: (3)
<223> OTHER INFORMATION: Base y represents t/u or c.
<221> NAME/KEY: variation
<222> LOCATION: (6)
<223> OTHER INFORMATION: Base n  represents inosine.
<221> NAME/KEY: variation
<222> LOCATION: (12)
<223> OTHER INFORMATION: Base r  represents g or a.
<221> NAME/KEY: variation
<222> LOCATION: (15)
<223> OTHER INFORMATION: Base n  represents inosine.
<221> NAME/KEY: variation
<222> LOCATION: (18)
<223> OTHER INFORMATION: Base n  represents inosine.
<221> NAME/KEY: variation
<222> LOCATION: (21)
<223> OTHER INFORMATION: Base y represents c or  t/u.
<221> NAME/KEY: variation
<222> LOCATION: (24)
<223> OTHER INFORMATION: Base n  represents inosine.

<400> SEQUENCE: 58
aaytcnatgc aracngtntt ygtng                               25

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence:  Synthetic
      Primer
<221> NAME/KEY: variation
<222> LOCATION: (3)
<223> OTHER INFORMATION: Base y represents c or  t/u.
<221> NAME/KEY: variation
<222> LOCATION: (6)
<223> OTHER INFORMATION: Base n  represents inosine..
<221> NAME/KEY: variation
<222> LOCATION: (9)
<223> OTHER INFORMATION: Base n  represents inosine.
<221> NAME/KEY: variation
<222> LOCATION: (12)
<223> OTHER INFORMATION: Base y  represents c or  t/u.
<221> NAME/KEY: variation
<222> LOCATION: (15)
<223> OTHER INFORMATION: Base n  represents inosine.
<221> NAME/KEY: variation
<222> LOCATION: (18)
<223> OTHER INFORMATION: Base n  represents inosine.
<221> NAME/KEY: variation
<222> LOCATION: (21)
<223> OTHER INFORMATION: Base n  represents inosine.
<221> NAME/KEY: variation
<222> LOCATION: (24)
<223> OTHER INFORMATION: Base y represents c or  t/u.

<400> SEQUENCE: 59
ttygtnggnt ayggnccnac nttyaa                              26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence:  Synthetic
      Primer
<221> NAME/KEY: variation
<222> LOCATION: (3)
<223> OTHER INFORMATION: Basen y represents c or  t/u.
<221> NAME/KEY: variation
<222> LOCATION: (6)
<223> OTHER INFORMATION: Base y represents c or  t/u.
<221> NAME/KEY: variation
<222> LOCATION: (9)
<223> OTHER INFORMATION: Base n  represents inosine.
<221> NAME/KEY: variation
<222> LOCATION: (12)
<223> OTHER INFORMATION: Base n  represents inosine.
<221> NAME/KEY: variation
<222> LOCATION: (15)
<223> OTHER INFORMATION: Base y  represents c or  t/u.
<221> NAME/KEY: variation
<222> LOCATION: (18)
<223> OTHER INFORMATION: Base n  represents inosine.

```
<221> NAME/KEY: variation
<222> LOCATION: (21)
<223> OTHER INFORMATION: Base y represents c or t/u.
<221> NAME/KEY: variation
<222> LOCATION: (24)
<223> OTHER INFORMATION: Base y represents c or t/u.

<400> SEQUENCE: 60
aaytayctna cnaaygtnga ygayat                                          26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer
<221> NAME/KEY: variation
<222> LOCATION: (3)
<223> OTHER INFORMATION: Base y represents c or t/u.
<221> NAME/KEY: variation
<222> LOCATION: (6)
<223> OTHER INFORMATION: Base y represents c or t/u.
<221> NAME/KEY: variation
<222> LOCATION: (9)
<223> OTHER INFORMATION: Base n represents inosine.
<221> NAME/KEY: variation
<222> LOCATION: (12)
<223> OTHER INFORMATION: Base n represents inosine.
<221> NAME/KEY: variation
<222> LOCATION: (15)
<223> OTHER INFORMATION: Base n represents inosine.
<221> NAME/KEY: variation
<222> LOCATION: (18)
<223> OTHER INFORMATION: Base n represents inosine..
<221> NAME/KEY: variation
<222> LOCATION: (21)
<223> OTHER INFORMATION: Base n represents inosine.
<221> NAME/KEY: variation
<222> LOCATION: (24)
<223> OTHER INFORMATION: Base n represents inosine.

<400> SEQUENCE: 61
gaygayatna cnctngtncc nggnac                                          26

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer
<221> NAME/KEY: variation
<222> LOCATION: (3)
<223> OTHER INFORMATION: Base y represents t/u or c.
<221> NAME/KEY: variation
<222> LOCATION: (6)
<223> OTHER INFORMATION: Base y represents c or t/u.
<221> NAME/KEY: variation
<222> LOCATION: (9)..(10)
<223> OTHER INFORMATION: Base r represents a or g. Base y represents
      c or t/u.
<221> NAME/KEY: variation
<222> LOCATION: (12)
<223> OTHER INFORMATION: Base n represents inosine.
<221> NAME/KEY: variation
<222> LOCATION: (15)
<223> OTHER INFORMATION: Base r represents a or g.
<221> NAME/KEY: variation
<222> LOCATION: (18)
<223> OTHER INFORMATION: Base r represents a or g.
<221> NAME/KEY: variation
<222> LOCATION: (21)
<223> OTHER INFORMATION: Base n represents inosine.
<221> NAME/KEY: variation
```

```
<222> LOCATION: (24)
<223> OTHER INFORMATION: Base n  represents inosine.
<221> NAME/KEY: variation
<222> LOCATION: (27)
<223> OTHER INFORMATION: Base n  represents inosine.

<400> SEQUENCE: 62
tgyttygary tncargargc nggnccncc                              29

<210> SEQ ID NO 63
<211> LENGTH: 18
<212> TYPE: DNA
<213> ORGANISM: Artificial Sequence
<220> FEATURE:
<223> OTHER INFORMATION: Putative autotoxin protein sequence from human
      liver
<221> NAME/KEY: VARIANT
<222> LOCATION: (860)
<223> OTHER INFORMATION: Xaa at positions: 860, 889, 905, 911, 927, 937,
      944, 950, 954, 967, 975 represents either an
      unknown or any amino acid residue.
<223> OTHER INFORMATION: Description of Artificial Sequence:Synthetic
      Primer

<400> SEQUENCE: 63
gctgtcttca aacacagc                                          18

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 64
ctggtggctg taatccatag c                                      21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 65
cgtgaaggca aagagaacac g                                      21

<210> SEQ ID NO 66
<211> LENGTH: 3104
<212> TYPE: DNA
<213> ORGANISM: Artificial Sequence
<220> FEATURE:
<223> OTHER INFORMATION: Description of Artificial Sequence:  Synthetic
      Polynucleotide

<400> SEQUENCE: 66
agtgcactcc gtgaaggcaa agagaacacg ctgcaaaagg ctttccaata atcctcgaca      60
tggcaaggag gagctcgttc cagtcgtgtc agataatatc cctgttcact tttgccgttg     120
gagtcaatat ctgcttagga ttcactgcac atcgaattaa gagagcagaa ggatgggagg     180
aaggtcctcc tacagtgcta tcagactccc ctggaccaa catctccgga tcttgcaagg      240
gcaggtgctt tgaacttcaa gaggctggac ctcctgattg tcgctgtgac aacttgtgta     300
agagctatac cagttgctgc catgactttg atgagctgtg tttgaagaca gcccgtgcgt     360
```

```
gggagtgtac taaggacaga tgtggagaag tcagaaatga agaaaatgcc tgtcactgct    420
cagaggactg cttggccagg ggagactgct gtaccaatta ccaagtggtt tgcaaaggag    480
agtcgcattg ggttgatgat gactgtgagg aaataaaggc cgcagaatgc cctgcagggt    540
ttgttcgccc tccattaatc atcttctccg tggatggctt ccgtgcatca tacatgaaga    600
aaggcagcaa agtcatgcct aatattgaaa aactaaggtc ttgtggcaca cactcgcccc    660
acatgaggcc ggtgtaccca actaaaacct ttcctaactt atacactttg gccactgggc    720
tatatccaga atcacatgga attgttggca attcaatgta tgatcctgta tttgatgcca    780
cttttcatct gcgagggcga gagaaattta atcatagatg gtggggaggt caaccgctat    840
ggattacagc caccaagcaa aggggtgaaa gctggaacat tcttttggtc tgttgtcatc    900
cctcacgagc ggagatatta accatattgc agtggctcac cctgccagat catgagaggc    960
ttcggtctat gccttctatt ctgagcaacc tgatttctct ggacacaaat atgcctttcg   1020
gccctgagat gacaaatcct ctgagggaaa tcgacaaaat tgtgggcaa ttaatggatg   1080 gactgaaaca actaaaactg catcggtgtg tcaacgtcat ctttgtcgga ccatggaa    1140 tggaagatgt cacatgtgat agaactgagt tcttgagtaa ttacctaact aatgtggatg   1200
atattacttt agtgcctgga actctaggaa ttcgatccaa atttagcaac aatgctaaat   1260
atgaccccaa agccattatt gccaatctca cgtgtaaaaa accagatcag cactttaagc   1320
cttacttgaa acagcacctt cccaaacgtt tgcactatgc caacaacaga gaattgagg   1380 atatccattt attggtggaa cgcagatggc atgttgcaag gaaacctttg gatgtttata   1440
agaaaccatc aggaaaatgc tttttccagg gagaccacgg atttgataac aaggtcaaca   1500
gcatgcagac tgttttttgta ggttatggcc caacatttaa gtacaagact aaagtgcctc   1560
catttgaaaa cattgaactt tacaatgtta tgtgtgatct cctgggattg aagccagctc   1620
ctaataatgg gacccatgga agtttgaatc atctcctgcg cactaatacc ttcaggccaa   1680
ccatgccaga ggaagttacc agacccaatt atccagggat tatgtacctt cagtctgatt   1740
ttgacctggg ctgcacttgt gatgataagg tagagccaaa gaacaagttg gatgaactca   1800
acaaacggct tcatacaaaa gggtctacag aagagagaca cctcctctat gggcgacctg   1860
cagtgcttta tcggactaga tatgatgtct tatatcacac tgactttgaa agtggttata   1920
gtgaaatatt cctaatgcca ctctggacat catatactgt ttccaaacag gctgaggttt   1980
ccagcgttcc tgaccatctg accagttgcg tccggcctga tgtccgtgtt tctccgagtt   2040
tcagtcagaa ctgtttggcc tacaaaaatg ataagcagat gtcctacgga ttcctctttc   2100
ctccttatct gagctcttca ccagaggcta aatatgatgc attccttgta accaatatgg   2160
ttccaatgta tcctgctttc aaacgggtct ggaattattt ccaaagggta ttggtgaaga   2220
aatatgcttc ggaaagaaat ggagttaacg tgataagtgg accaatcttc gactatgact   2280
atgatggctt acatgacaca gaagacaaaa taaaacagta cgtggaaggc agttccattc   2340
ctgttccaac tcactactac agcatcatca ccagctgtct ggatttcact cagcctgccg   2400
acaagtgtga cggccctctc tctgtgtcct ccttcatcct ccgtcaccgg cctgacaacg   2460
aggagagctg caatagctca gaggacgaat caaaatgggt agaagaactc atgaagatgc   2520
acacggctag ggtgcgtgac attgaacatc tcaccagcct ggacttcttc gaaagacca   2580 gccgcagcta cccagaaatc ctgacactca agacatacct gcatacatat gagagcgaga   2640
tttaactttc tgagcatctg cagtacagtc ttatcaactg gttgtatatt tttatattgt   2700
ttttgtattt attaatttga aaccaggaca ttaaaaatgt tagtatttta atcctgtacc   2760
```

-continued

```
aaatctgaca tattatgcct gaatgactcc actgtttttc tctaatgctt gatttaggta    2820
gccttgtgtt ctgagtagag cttgtaataa atactgcagc ttgagttttt agtggaagct    2880
tctaaatggt gctgcagatt tgatatttgc attgaggaaa tattaatttt ccaatgcaca    2940
gttgccacat ttagtcctgt actgtatgga aacactgatt ttgtaaagtt gcctttattt    3000
gctgttaact gttaactatg acagatatat ttaagcctta taaccaatc ttaaacataa     3060 taaatcacac attcagtttt ttctggtaaa aaaaaaaaa aaaa                      3104
```

<210> SEQ ID NO 67
<211> LENGTH: 861
<212> TYPE: PRT
<213> ORGANISM: Artificial Sequence
<220> FEATURE:
<223> OTHER INFORMATION: Description of Artificial Sequence: Synthetic Polypeptide

<400> SEQUENCE: 67

```
Met Ala Arg Arg Ser Ser Phe Gln Ser Cys Gln Ile Ile Ser Leu Phe
 1               5                   10                  15

Thr Phe Ala Val Gly Val Asn Ile Cys Leu Gly Phe Thr Ala His Arg
                20                  25                  30

Ile Lys Arg Ala Glu Gly Trp Glu Gly Pro Pro Thr Val Leu Ser
            35                  40                  45

Asp Ser Pro Trp Thr Asn Ile Ser Gly Ser Cys Lys Gly Arg Cys Phe
        50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Ala Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro His Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Arg Gly Glu Ser Trp
            260                 265                 270

Asn Ile Leu Leu Val Cys Cys His Pro Ser Arg Ala Glu Ile Leu Thr
        275                 280                 285

Ile Leu Gln Trp Leu Thr Leu Pro Asp His Glu Arg Leu Arg Ser Met
```

-continued

```
            290                 295                 300
Pro Ser Ile Leu Ser Asn Leu Ile Ser Leu Asp Thr Asn Met Pro Phe
305                 310                 315                 320
Gly Pro Glu Met Thr Asn Pro Leu Arg Glu Ile Asp Lys Ile Val Gly
                325                 330                 335
Gln Leu Met Asp Gly Leu Lys Gln Leu Lys Leu His Arg Cys Val Asn
                340                 345                 350
Val Ile Phe Val Gly Asp His Gly Met Glu Asp Val Thr Cys Asp Arg
                355                 360                 365
Thr Glu Phe Leu Ser Asn Tyr Leu Thr Asn Val Asp Asp Ile Thr Leu
                370                 375                 380
Val Pro Gly Thr Leu Gly Ile Arg Ser Lys Phe Ser Asn Asn Ala Lys
385                 390                 395                 400
Tyr Asp Pro Lys Ala Ile Ile Ala Asn Leu Thr Cys Lys Lys Pro Asp
                405                 410                 415
Gln His Phe Lys Pro Tyr Leu Lys Gln His Leu Pro Lys Arg Leu His
                420                 425                 430
Tyr Ala Asn Asn Arg Arg Ile Glu Asp Ile His Leu Leu Val Glu Arg
                435                 440                 445
Arg Trp His Val Ala Arg Lys Pro Leu Asp Val Tyr Lys Lys Pro Ser
450                 455                 460
Gly Lys Cys Phe Phe Gln Gly Asp His Gly Phe Asp Asn Lys Val Asn
465                 470                 475                 480
Ser Met Gln Thr Val Phe Val Gly Tyr Gly Pro Thr Phe Lys Tyr Lys
                485                 490                 495
Thr Lys Val Pro Pro Phe Glu Asn Ile Glu Leu Tyr Asn Val Met Cys
                500                 505                 510
Asp Leu Leu Gly Leu Lys Pro Ala Pro Asn Asn Gly Thr His Gly Ser
                515                 520                 525
Leu Asn His Leu Leu Arg Thr Asn Thr Phe Arg Pro Thr Met Pro Glu
                530                 535                 540
Glu Val Thr Arg Pro Asn Tyr Pro Gly Ile Met Tyr Leu Gln Ser Asp
545                 550                 555                 560
Phe Asp Leu Gly Cys Thr Cys Asp Asp Lys Val Glu Pro Lys Asn Lys
                565                 570                 575
Leu Asp Glu Leu Asn Lys Arg Leu His Thr Lys Gly Ser Thr Glu Glu
                580                 585                 590
Arg His Leu Leu Tyr Gly Arg Pro Ala Val Leu Tyr Arg Thr Arg Tyr
                595                 600                 605
Asp Val Leu Tyr His Thr Asp Phe Glu Ser Gly Tyr Ser Glu Ile Phe
                610                 615                 620
Leu Met Pro Leu Trp Thr Ser Tyr Thr Val Ser Lys Gln Ala Glu Val
625                 630                 635                 640
Ser Ser Val Pro Asp His Leu Thr Ser Cys Val Arg Pro Asp Val Arg
                645                 650                 655
Val Ser Pro Ser Phe Ser Gln Asn Cys Leu Ala Tyr Lys Asn Asp Lys
                660                 665                 670
Gln Met Ser Tyr Gly Phe Leu Phe Pro Pro Tyr Leu Ser Ser Ser Pro
                675                 680                 685
Glu Ala Lys Tyr Asp Ala Phe Leu Val Thr Asn Met Val Pro Met Tyr
                690                 695                 700
Pro Ala Phe Lys Arg Val Trp Asn Tyr Phe Gln Arg Val Leu Val Lys
705                 710                 715                 720
```

```
Lys Tyr Ala Ser Glu Arg Asn Gly Val Asn Val Ile Ser Gly Pro Ile
            725                 730                 735

Phe Asp Tyr Asp Tyr Asp Gly Leu His Asp Thr Glu Asp Lys Ile Lys
        740                 745                 750

Gln Tyr Val Glu Gly Ser Ser Ile Pro Val Pro Thr His Tyr Tyr Ser
        755                 760                 765

Ile Ile Thr Ser Cys Leu Asp Phe Thr Gln Pro Ala Asp Lys Cys Asp
    770                 775                 780

Gly Pro Leu Ser Val Ser Ser Phe Ile Leu Arg His Arg Pro Asp Asn
785                 790                 795                 800

Glu Glu Ser Cys Asn Ser Ser Glu Asp Glu Ser Lys Trp Val Glu Glu
                805                 810                 815

Leu Met Lys Met His Thr Ala Arg Val Arg Asp Ile Glu His Leu Thr
            820                 825                 830

Ser Leu Asp Phe Phe Arg Lys Thr Ser Arg Ser Tyr Pro Glu Ile Leu
        835                 840                 845

Thr Leu Lys Thr Tyr Leu His Thr Tyr Glu Ser Glu Ile
        850                 855                 860

<210> SEQ ID NO 68
<211> LENGTH: 3251
<212> TYPE: DNA
<213> ORGANISM: Artificial Sequence
<220> FEATURE:
<223> OTHER INFORMATION: Description of Artificial Sequence:  Synthetic
      Polynucleotide

<400> SEQUENCE: 68
cgtgaaggca aagagaacac gctgcaaaag gcttccaaga atcctcgaca tggcaaggag      60
gagctcgttc cagtcgtgtc agataatatc cctgttcact tttgccgttg gagtcagtat     120
ctgcttagga ttcactgcac atcgaattaa gagagcagaa ggatgggagg aaggtcctcc     180
tacagtgcta tcagactccc cctggaccaa catctccgga tcttgcaagg gcaggtgctt     240
tgaacttcaa gaggctggac ctcctgattg tcgctgtgac aacttgtgta agagctatac     300
cagttgctgc catgactttg atgagctgtg tttgaagaca gcccgtggct gggagtgtac     360
taaggacaga tgtggagaag tcagaaatga agaaaatgcc tgtcactgct cagaggactg     420
cttggccagg ggagactgct gtaccaatta ccaagtggtt tgcaaaggag agtcgcattg     480
ggttgatgat gactgtgagg aaataaaggc cgcagaatgc cctgcagggt ttgttcgccc     540
tccattaatc atcttctccg tggatggctt ccgtgcatca tacatgaaga aaggcagcaa     600
agtcatgcct aatattgaaa actaaggtc ttgtggcaca cactctccct acatgaggcc     660
ggtgtaccca actaaaacct ttcctaactt atacactttg gccactgggc tatatccaga     720
atcacatgga attgttggca attcaatgta tgatcctgta tttgatgcca cttttcatct     780
gcgagggcga gagaaattta atcatagatg gtggggaggt caaccgctat ggattacagc     840
caccaagcaa ggggtgaaag ctggaacatt cttttggtct gttgtcatcc ctcacgagcg     900
gagaatatta accatattgc ggtggctcac cctgccagat catgagaggc cttcggtcta     960
tgccttctat tctgagcaac tgatttctc tggacacaaa tatggccctt tcggccctga    1020
ggagagtagt tatggctcac cttttactcc ggctaagaga cctaagagga agttgccccc    1080
taagaggaga caggaaagac cagttgctcc tccaaagaaa agaagaagaa aatacatag    1140 gatggatcat tatgctgcgg aaactcgtca ggacaaaatg acaaatcctc tgagggaaat    1200
```

```
                                     -continued cgacaaaatt gtggggcaat taatggatgg actgaaacaa ctaaaactgc gtcggtgtgt    1260
caacgtcatc tttgtcggag accatggaat ggaagatgtc acatgtgata gaactgagtt    1320
cttgagtaat tacctaacta atgtggatga tattacttta gtgcctggaa ctctaggaag    1380
aattcgatcc aaatttagca acaatgctaa atatgacccc aaagccatta ttgccaatct    1440
cacgtgtaaa aaaccagatc agcactttaa gccttacttg aaacagcacc ttcccaaacg    1500
tttgcactat gccaacaaca aagaattga ggatatccat ttattggtgg aacgcagatg    1560
gcatgttgca aggaaacctt tggatgttta taagaaacca tcaggaaaat gcttttccca    1620
gggagaccac ggatttgata acaaggtcaa cagcatgcag actgtttttg taggttatgg    1680
cccaacattt aagtacaaga ctaaagtgcc tccatttgaa acattgaac tttacaatgt     1740 tatgtgtgat ctcctgggat gaagccagc tcctaataat gggacccatg aagtttgaa      1800 tcatctcctg cgcactaata ccttcaggcc aaccatgcca gaggaagtta ccagacccaa    1860
ttatccaggg attatgtacc ttcagtctga ttttgacctg ggctgcactt gtgatgataa    1920
ggtagagcca aagaacaagt tggatgaact caacaaacgg cttcatacaa aagggtctac    1980
agaagagaga cacctcctct atgggcgacc tgcagtgctt tatcggacta gatatgatat    2040
cttatatcac actgactttg aaagtggtta tagtgaaata ttcctaatgc tactctggac    2100
atcatatact gtttccaaac aggctgaggt ttccagcgtt cctgaccatc tgaccagttg    2160
cgtccggcct gatgtccgtg tttctccgag tttcagtcag aactgtttgg cctacaaaaa    2220
tgataagcag atgtcctacg gattcctctt tcctccttat ctgagctctt caccagaggc    2280
taaatatgat gcattccttg taaccaatat ggttccaatg tatcctgctt tcaaacgggt    2340
ctggaattat ttccaaaggg tattggtgaa gaaatatgct tcggaaagaa atggagttaa    2400
cgtgataagt ggaccaatct tcgactatga ctatgatggc ttacatgaca cagaagacaa    2460
aataaaacag tacgtggaag gcagttccat tcctgttcca actcactact acagcatcat    2520
caccagctgt ctggatttca ctcagcctgc cgacaagtgt gacggccctc tctctgtgtc    2580
ctccttcatc ctgcctcacc ggcctgacaa cgaggagagc tgcaatagct cagaggacga    2640
atcaaaatgg gtagaagaac tcatgaagat gcacacagct agggtgcgtg acattgaaca    2700
tctcaccagc ctggacttct tccgaaagac cagccgcagc tacccagaaa tcctgacact    2760
caagacatac ctgcatacat atgagagcga gatttaactt tctgagcatc tgcagtacag    2820
tcttatcaac tggttgtata ttttatatt gtttttgtat ttattaattt gaaaccagga    2880
cattaaaaat gttagtattt taatcctgta ccaaatctga catattatgc ctgaatgact    2940
ccactgtttt tctctaatgc ttgatttagg tagccttgtg ttctgagtag agcttgtaat    3000
aaatactgca gcttgagaaa aagtggaagc ttctaaatgg tgctgcagat tgatatttg     3060 cattgaggaa atattaattt tccaatgcac agttgccaca tttagtcctg tactgtatgg    3120
aaacactgat tttgtaaagt tgcctttatt tgctgttaac tgttaactat gacagatata    3180
tttaagcctt ataaaccaat cttaaacata ataaatcaca cattcagttt taaaaaaaaa    3240 aaaaaaaaa a                                                          3251
```

<210> SEQ ID NO 69
<211> LENGTH: 915
<212> TYPE: PRT
<213> ORGANISM: Artificial Sequence
<220> FEATURE:
<223> OTHER INFORMATION: Description of Artificial Sequence: Synthetic
      Polypeptide -continued

```
<400> SEQUENCE: 69

Met Ala Arg Arg Ser Ser Phe Gln Ser Cys Gln Ile Ile Ser Leu Phe
  1               5                  10                  15

Thr Phe Ala Val Gly Val Ser Ile Cys Leu Gly Phe Thr Ala His Arg
             20                  25                  30

Ile Lys Arg Ala Glu Gly Trp Glu Gly Pro Pro Thr Val Leu Ser
         35                  40                  45

Asp Ser Pro Trp Thr Asn Ile Ser Gly Ser Cys Lys Gly Arg Cys Phe
     50                  55                  60

Glu Leu Gln Glu Ala Gly Pro Pro Asp Cys Arg Cys Asp Asn Leu Cys
 65                  70                  75                  80

Lys Ser Tyr Thr Ser Cys Cys His Asp Phe Asp Glu Leu Cys Leu Lys
                 85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
            115                 120                 125

Asp Cys Cys Thr Asn Tyr Gln Val Val Cys Lys Gly Glu Ser His Trp
130                 135                 140

Val Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
                180                 185                 190

Arg Ser Cys Gly Thr His Ser Pro Tyr Met Arg Pro Val Tyr Pro Thr
            195                 200                 205

Lys Thr Phe Pro Asn Leu Tyr Thr Leu Ala Thr Gly Leu Tyr Pro Glu
210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
                260                 265                 270

Thr Phe Phe Trp Ser Val Val Ile Pro His Glu Arg Arg Ile Leu Thr
            275                 280                 285

Ile Leu Arg Trp Leu Thr Leu Pro Asp His Glu Arg Pro Ser Val Tyr
290                 295                 300

Ala Phe Tyr Ser Glu Gln Pro Asp Phe Ser Gly His Lys Tyr Gly Pro
305                 310                 315                 320

Phe Gly Pro Glu Glu Ser Ser Tyr Gly Ser Pro Phe Thr Pro Ala Lys
                325                 330                 335

Arg Pro Lys Arg Lys Val Ala Pro Lys Arg Arg Gln Glu Arg Pro Val
            340                 345                 350

Ala Pro Pro Lys Lys Arg Arg Lys Ile His Arg Met Asp His Tyr
            355                 360                 365

Ala Ala Glu Thr Arg Gln Asp Lys Met Thr Asn Pro Leu Arg Glu Ile
370                 375                 380

Asp Lys Ile Val Gly Gln Leu Met Asp Gly Leu Lys Gln Leu Lys Leu
385                 390                 395                 400

Arg Arg Cys Val Asn Val Ile Phe Val Gly Asp His Gly Met Glu Asp
                405                 410                 415
```

-continued

Val Thr Cys Asp Arg Thr Glu Phe Leu Ser Asn Tyr Leu Thr Asn Val
            420                 425                 430

Asp Asp Ile Thr Leu Val Pro Gly Thr Leu Gly Arg Ile Arg Ser Lys
            435                 440                 445

Phe Ser Asn Asn Ala Lys Tyr Asp Pro Lys Ala Ile Ile Ala Asn Leu
            450                 455                 460

Thr Cys Lys Lys Pro Asp Gln His Phe Lys Pro Tyr Leu Lys Gln His
465                 470                 475                 480

Leu Pro Lys Arg Leu His Tyr Ala Asn Asn Arg Arg Ile Glu Asp Ile
                485                 490                 495

His Leu Leu Val Glu Arg Arg Trp His Val Ala Arg Lys Pro Leu Asp
            500                 505                 510

Val Tyr Lys Lys Pro Ser Gly Lys Cys Phe Phe Gln Gly Asp His Gly
            515                 520                 525

Phe Asp Asn Lys Val Asn Ser Met Gln Thr Val Phe Val Gly Tyr Gly
            530                 535                 540

Pro Thr Phe Lys Tyr Lys Thr Lys Val Pro Pro Phe Glu Asn Ile Glu
545                 550                 555                 560

Leu Tyr Asn Val Met Cys Asp Leu Leu Gly Leu Lys Pro Ala Pro Asn
                565                 570                 575

Asn Gly Thr His Gly Ser Leu Asn His Leu Leu Arg Thr Asn Thr Phe
            580                 585                 590

Arg Pro Thr Met Pro Glu Glu Val Thr Arg Pro Asn Tyr Pro Gly Ile
            595                 600                 605

Met Tyr Leu Gln Ser Asp Phe Asp Leu Gly Cys Thr Cys Asp Asp Lys
            610                 615                 620

Val Glu Pro Lys Asn Lys Leu Asp Glu Leu Asn Lys Arg Leu His Thr
625                 630                 635                 640

Lys Gly Ser Thr Glu Glu Arg His Leu Leu Tyr Gly Arg Pro Ala Val
                645                 650                 655

Leu Tyr Arg Thr Arg Tyr Asp Ile Leu Tyr His Thr Asp Phe Glu Ser
                660                 665                 670

Gly Tyr Ser Glu Ile Phe Leu Met Leu Leu Trp Thr Ser Tyr Thr Val
            675                 680                 685

Ser Lys Gln Ala Glu Val Ser Ser Val Pro Asp His Leu Thr Ser Cys
690                 695                 700

Val Arg Pro Asp Val Arg Val Ser Pro Ser Phe Ser Gln Asn Cys Leu
705                 710                 715                 720

Ala Tyr Lys Asn Asp Lys Gln Met Ser Tyr Gly Phe Leu Phe Pro Pro
                725                 730                 735

Tyr Leu Ser Ser Pro Glu Ala Lys Tyr Asp Ala Phe Leu Val Thr
                740                 745                 750

Asn Met Val Pro Met Tyr Pro Ala Phe Lys Arg Val Trp Asn Tyr Phe
            755                 760                 765

Gln Arg Val Leu Val Lys Lys Tyr Ala Ser Glu Arg Asn Gly Val Asn
            770                 775                 780

Val Ile Ser Gly Pro Ile Phe Asp Tyr Asp Tyr Asp Gly Leu His Asp
785                 790                 795                 800

Thr Glu Asp Lys Ile Lys Gln Tyr Val Glu Gly Ser Ser Ile Pro Val
                805                 810                 815

Pro Thr His Tyr Tyr Ser Ile Ile Thr Ser Cys Leu Asp Phe Thr Gln
            820                 825                 830

```
Pro Ala Asp Lys Cys Asp Gly Pro Leu Ser Val Ser Ser Phe Ile Leu
        835                 840                 845

Pro His Arg Pro Asp Asn Glu Glu Ser Cys Asn Ser Ser Glu Asp Glu
        850                 855                 860

Ser Lys Trp Val Glu Glu Leu Met Lys Met His Thr Ala Arg Val Arg
865                 870                 875                 880

Asp Ile Glu His Leu Thr Ser Leu Asp Phe Phe Arg Lys Thr Ser Arg
                885                 890                 895

Ser Tyr Pro Glu Ile Leu Thr Leu Lys Thr Tyr Leu His Thr Tyr Glu
            900                 905                 910

Ser Glu Ile
        915

<210> SEQ ID NO 70
<211> LENGTH: 979
<212> TYPE: PRT
<213> ORGANISM: Homo sapiens
<220> FEATURE:
<223> OTHER INFORMATION: Putative autotoxin protein sequence from human
      liver.
<221> NAME/KEY: VARIANT
<222> LOCATION: (860)
<223> OTHER INFORMATION: Xaa at positions: 860, 889, 905, 911, 927, 937,
      944, 950, 954, 967, and 975 represents an unknown
      or other amino acid.

<400> SEQUENCE: 70

Met Ala Arg Arg Ser Ser Phe Gln Ser Cys Gln Asp Ile Ser Leu Phe
 1               5                  10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Ala Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Leu Gln Val
145                 150                 155                 160

Cys Ser Pro Ser Ile Asn His Leu Leu Arg Gly Trp Leu Pro Met Thr
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240
```

```
Thr Phe His Leu Arg Gly Arg Glu Lys Phe Asn His Arg Trp Trp Gly
                245                 250                 255

Gly Gln Pro Leu Trp Ile Thr Ala Thr Lys Gln Arg Gly Glu Ser Trp
            260                 265                 270

Asn Ile Leu Leu Val Cys Cys His Pro Ser Arg Ala Glu Ile Leu Thr
                275                 280                 285

Ile Leu Gln Trp Leu Thr Leu Pro Asp His Glu Arg Pro Ser Val Tyr
            290                 295                 300

Ala Phe Tyr Ser Glu Gln Pro Asp Phe Ser Gly His Lys His Met Pro
305                 310                 315                 320

Phe Gly Pro Glu Met Thr Asn Pro Leu Arg Glu Met His Lys Ile Val
                325                 330                 335

Gly Gln Leu Met Asp Gly Leu Lys Gln Leu Lys Leu His Arg Cys Val
                340                 345                 350

Asn Val Ile Phe Val Glu Thr Met Asp Gly Arg Cys His Met Tyr Arg
                355                 360                 365

Thr Glu Phe Leu Ser Asn Tyr Leu Thr Asn Val Asp Asp Ile Thr Leu
            370                 375                 380

Val Pro Gly Thr Leu Gly Arg Ile Arg Ser Lys Phe Ser Asn Asn Ala
385                 390                 395                 400

Lys Tyr Asp Pro Lys Ala Ile Ile Ala Asn Leu Thr Cys Lys Lys Pro
                405                 410                 415

Asp Gln His Phe Lys Pro Tyr Leu Lys Gln His Leu Pro Lys Arg Leu
                420                 425                 430

His Tyr Ala Asn Asn Arg Arg Ile Glu Asp Ile His Leu Leu Val Glu
            435                 440                 445

Arg Arg Trp His Val Ala Arg Lys Pro Leu Asp Val Tyr Lys Lys Pro
450                 455                 460

Ser Gly Asn Ala Phe Ser Arg Glu Thr Thr Ala Phe Asp Asn Lys Val
465                 470                 475                 480

Asn Ser Met Gln Thr Val Phe Val Gly Tyr Gly Pro Thr Phe Lys Tyr
                485                 490                 495

Lys Thr Lys Val Pro Pro Phe Glu Asn Ile Glu Leu Tyr Asn Val Met
                500                 505                 510

Cys Asp Leu Leu Gly Leu Lys Pro Ala Pro Asn Asn Gly Thr His Gly
            515                 520                 525

Ser Leu Asn His Leu Leu Arg Thr Asn Thr Phe Arg Pro Thr Met Pro
            530                 535                 540

Glu Glu Val Thr Arg Pro Asn Tyr Pro Gly Ile Met Tyr Leu Gln Ser
545                 550                 555                 560

Asp Phe Asp Leu Gly Cys Thr Cys Asp Asp Lys Val Glu Pro Lys Asn
                565                 570                 575

Lys Leu Asp Glu Leu Asn Lys Arg Leu His Thr Lys Gly Ser Thr Glu
            580                 585                 590

Glu Arg His Leu Leu Tyr Gly Asp Arg Pro Ala Val Leu Tyr Arg Thr
            595                 600                 605

Arg Tyr Asp Ile Leu Tyr His Thr Asp Phe Glu Ser Gly Tyr Ser Glu
610                 615                 620

Ile Phe Leu Met Pro Leu Trp Thr Ser Tyr Thr Val Ser Lys Gln Ala
625                 630                 635                 640

Glu Val Ser Ser Val Pro Asp His Leu Thr Ser Cys Val Arg Pro Asp
                645                 650                 655

Val Arg Val Ser Pro Ser Phe Ser Gln Asn Cys Leu Ala Tyr Lys Asn
```

-continued

```
                    660                     665                     670
Asp Lys Gln Met Ser Tyr Gly Phe Leu Phe Pro Pro Tyr Leu Ser Ser
        675                     680                     685

Ser Pro Glu Ala Lys Tyr Asp Ala Phe Leu Val Thr Asn Met Val Pro
        690                     695                     700

Met Tyr Pro Ala Phe Lys Arg Val Trp Asn Tyr Phe Gln Arg Val Leu
705                     710                     715                     720

Val Lys Lys Tyr Ala Ser Glu Arg Asn Gly Val Asn Val Ile Ser Gly
                725                     730                     735

Pro Ile Phe Asp Tyr Asp Tyr Asp Gly Leu His Asp Thr Glu Asp Lys
                740                     745                     750

Ile Lys Gln Tyr Val Glu Gly Ser Ser Ile Pro Val Pro Thr His Tyr
        755                     760                     765

Tyr Ser Ile Ile Thr Ser Cys Leu Asp Phe Thr Gln Pro Ala Asp Lys
    770                     775                     780

Cys Asp Gly Pro Leu Ser Val Ser Ser Phe Ile Leu Pro His Arg Pro
785                     790                     795                     800

Asp Asn Glu Glu Ser Cys Asn Ser Ser Glu Asp Glu Ser Lys Trp Val
                805                     810                     815

Glu Glu Leu Met Lys Met His Thr Ala Arg Val Arg Asp Ile Glu His
                820                     825                     830

Leu Thr Ser Leu Asp Phe Phe Arg Lys Thr Ser Arg Ser Tyr Pro Glu
        835                     840                     845

Ile Leu Thr Leu Lys Thr Tyr Leu His Thr Tyr Glu Ser Glu Ile Xaa
    850                     855                     860

Leu Ser Glu His Leu Gln Tyr Ser Leu Ile Asn Trp Leu Tyr Ile Phe
865                     870                     875                     880

Ile Leu Phe Leu Tyr Leu Leu Ile Xaa Asn Gln Asp Ile Lys Asn Val
                885                     890                     895

Ser Ile Leu Ile Leu Tyr Gln Ile Xaa His Ile Met Pro Glu Xaa Leu
                900                     905                     910

His Cys Phe Ser Leu Met Leu Asp Leu Gly Ser Leu Val Phe Xaa Val
        915                     920                     925

Glu Leu Val Ile Asn Thr Ala Ala Xaa Val Phe Ser Gly Ser Phe Xaa
    930                     935                     940

Met Val Leu Gln Ile Xaa Tyr Leu His Xaa Gly Asn Ile Asn Phe Pro
945                     950                     955                     960

Met His Ser Cys His Ile Xaa Ser Cys Thr Val Trp Lys His Xaa Phe
                965                     970                     975

Cys Lys Val
```

US 6,417,338 B1

AUTOTAXIN: MOTILITY STIMULATING PROTEIN USEFUL IN CANCER DIAGNOSIS AND THERAPY

This application is a continuation of application Ser. No. 08/977,221 filed Nov. 24, 1997, which is now U.S. Pat. No. 6,084,069, which is a divisional of application Ser. No. 08/364,455 filed Dec. 27, 1994 now abandoned, which is a continuation-in-part of application Ser. No. 08/249,182 filed May 25, 1994 now abandoned, which is a continuation-in-part of application Ser. No. 07/822,043 filed Jan. 17, 1992, which is now U.S. Pat. No. 5,449,753.

FIELD OF THE INVENTION

The present invention relates, in general, to a motility stimulating protein and compositions comprising the same. In particular, the present invention relates to a purified form of the protein and peptides thereof, for example, autotaxin (herein alternative referred to as "ATX"); a DNA segment encoding autotaxin; recombinant DNA molecules containing the DNA segment; cells containing the recombinant DNA molecule; a method of producing autotaxin; antibodies to autotaxin; and methods of cancer diagnosis and therapy using the above referenced protein or peptides thereof and DNA segments.

BACKGROUND OF THE INVENTION

Cell motility plays an important role in embryonic events, adult tissue remodeling, wound healing, angiogenesis, immune defense, and metastasis of tumor cells (Singer, 1986). In normal physiologic processes, motility is tightly regulated. On the other hand, tumor cell motility may be aberrantly regulated or autoregulated. Tumor cells can respond in a motile fashion to a variety of agents. These include host-derived factors such as scatter factor (Rosen, et al., 1989) and growth factors (Kahan, et al., 1987; Stracke, et al.; Tamm, et al., 1989; Wang, et al. 1990; and Jouanneau, et al. 1991), components of the extracellular matrix (McCarthy, et al. 1984), and tumor-secreted or autocrine factors (Liotta, et al. 1988; Ruff, et al. 1985; Atnip, et al. 1987; Ohnishi, et al. 1990; Silletti, et al. 1991; and Watanabe, et al. 1991).

Many types of host-derived soluble factors act in a paracrine fashion to stimulate cell locomotion. Motility-stimulating proteins called "scatter factors" have been identified which are produced by embryonic fibroblasts and by smooth muscle cells (Stoker, et al. 1987). Scatter factors stimulate random and directed motility by epithelial cells, keratinocytes, vascular endothelial cells and carcinoma cells (Stoker, et al. 1987; Rosen, et al. 1990; and Weidner, et al. 1990), but not fibroblasts. In addition, a number of host-secreted growth factors have been demonstrated to stimulate motility in tumor cells, including nerve growth factor (Kahan, et al. 1987) insulin-like growth factor-I (Stracke, et al. 1988), interleukin-6 (Tamm, et al. 1989), interleukin-8 (Wang, et al. 1990), and acidic fibroblast growth factor (Jouanneau, et al. 1991). These paracrine factors may influence "homing" or the directionality of tumor cell motility.

In contrast to these host-derived factors, many types of tumor cells have been found to produce proteins termed "autocrine motility factors" which stimulate motility by the same tumor cells which make the factor (Liotta, et al. 1986). Autocrine motility factors are not specific for a given type of cancer cell but have a wide spectrum of activity on many types of cancer cells (Kohn, et al. 1990), with little effect on normal fibroblasts or leukocytes.

Autocrine motility factors identified to date act through cell-surface receptors (Stracke, et al. 1987; Nabi, et al. 1990; Watanabe, et al. 1991) resulting in pseudopodial protrusion (Guirguis, et al. 1987) leading to both random and directed migration (Liotta, et al. 1986; Atnip, et al. 1987; Ohnishi, et al. 1990).

Prior studies of human A2058 melanoma cells have demonstrated that these cells are a particularly rich source of autocrine motility factors. An autocrine motility factor with a molecular mass of approximately 60 kDa has been previously isolated from the conditioned media of these cells. (Liotta, et al. 1986). Similar tumor cells derived or induced factors with the same molecular weight have subsequently been reported and purified by several investigators (Atnip, et al. 1987; Schnor, et al. 1988; Ohnishi, et al. 1990; Silletti, et al. 1991; Watanabe et al. 1990). Such factors are thought to play a key role in tumor cell invasion.

Most of the motility factors identified to date have not been purified to homogeneity and have not been sequenced. The novel tumor motility factor of the present invention, named herein as autotaxin ("ATX"), has been purified and verified to be a homogeneous sample by two-dimensional gel electrophoresis. The protein of the present invention is unique from any previously identified or purified motility factor. The molecular size of ATX is about 125 kilo Daltons ("kDa") and it has an isoelectric point of approximately 7.7. ATX stimulates both random and directed migration of human A2058 melanoma cells at picomolar concentrations. The activity of the ATX factor is completely sensitive to inhibition by pertussis toxin. No significant homology has been found to exist between the protein of the invention and any mammalian protein including previous factors known to stimulate cell motility.

There is a great clinical need to predict the aggressiveness of a patient's individual tumor, to predict the local recurrence of treated tumors and to identify patients at high risk for development of invasive tumors. The present invention provides a functional marker which is functionally related to the invasive potential of human cancer. The invention further provides an assay for this secreted marker in body fluids, or in tissues. The assay of the invention can be used in the detection, diagnosis, and treatment of human malignancies and other inflammatory, fibrotic, infectious or healing disorders.

SUMMARY OF THE INVENTION

The present invention relates, generally, to a motility stimulating protein and corresponding peptides thereof, and to a DNA segment encoding same. A human cDNA clone encoding a tumor cell motility-stimulating protein, herein referred to as autotaxin or "ATX", reveals that this protein is an ecto/exoenzyme with significant homology to the plasma cell membrane differentiation antigen PC-1. ATX is a 125 kDa glycoprotein, previously isolated from a human melanoma cell line (A2058), which elicits chemotactic and chemokinetic responses at picomolar to nanomolar concentrations.

It is a specific object of the present invention to provide autotaxin and peptide fragments thereof.

It is a further object of the present invention to provide a DNA segment that encodes autotaxin and a recombinant DNA molecule comprising same. It is a further object of the present invention to provide a cell that contains such a recombinant molecule and a method of producing autotaxin using that cell.

Another object of the present invention is the identification of a transmembrane domain of the human liver autotaxin protein and its apparent absence in tumorous forms of autotaxin. The tumorous form of autotaxin appears to be a secreted protein. The present invention relates to utilization of the different sites of localization for diagnosis and prognosis of the stages of tumor progression. Further, the invention relates to treatment methods, designed to advantageously block the secreted form of autotaxin activity while having little effect on the membrane-bound form of autotaxin.

Yet another object of the present invention relates to the identification of a highly variable region within the autotaxin gene, called a "hot spot". The variations in sequence apparently result in mutations, insertions, deletions and premature termination of translation. The present invention relates to manipulating this region so as to alter the activity of the protein. Further, the hot spot can serve as a marker in tumor diagnosis differentiating between different forms of the autotaxin protein.

It is yet another object of the present invention to provide a method of purifying autotaxin.

It is a further object of the present invention to provide cloned DNA segments encoding autotaxin and fragments thereof. The cDNA encoding the entire autotaxin protein contains 3251 base pairs, and has an MRNA size of approximately 3.3 kb. The full-length deduced amino acid sequence of autotaxin comprises a protein of 915 amino acids. Database analysis of the ATX sequence revealed a 45% amino acid identity (including 30 out of 33 cysteines) with PC-1, a pyrophosphatase/type I phosphodiesterase expressed on the surface of activated B cells and plasma cells. ATX, like PC-1, was found to hydrolyze the type I phosphodiesterase substrate p-nitrophenyl thymidine-5' monophosphate. Autotaxin now defines a novel motility-regulating function for this class of ecto/exo-enzymes.

Further objects and advantages of the present invention will be clear from the description that follows.

BRIEF DESCRIPTION OF THE DRAWINGS

FIG. 7. Two-dimensional gel electrophoresis of ATX. Purified ATX (FIG. 6, Panel C) was subjected to non-equilibrium isoelectric focusing (5 hr. at 500v), then applied to a 7.5% SDS-polyacrylamide gel for the second dimension. The pH separation which resulted was measured in 0.5 cm samples of concurrently run tube gels and is shown at the top. Molecular weight standards for the second dimension are shown on the right. This analysis reveals a single component with pI=7.7±0.2 and $M_r$=120,000.

FIG. 13. Schematic Diagram of autotaxin gene region.

For A2058: 4C11 is the original DNA clone obtained by screening an A2058 cDNA expression library in λgt11 with anti-peptide ATX-102. Upstream ATX peptide sequences were utilized for PCR amplification of A2058 MRNA, using the technique of reverse transcription/PRC. These peptides include ATX-101, ATX-103, and ATX-224. The approximate localization of each of peptide was obtained by matching the peptide with its homologous region on PC-1.

For N-tera 2D1, a λgt10 cDNA library was amplified and the cDNA inserts were isolated. PCR amplification, based on homologies with A2058 sequence, was utilized for DNA sequencing.

For normal human liver, a MRNA from liver was amplified with 5' RACE using primers from the known ATX-224 region of A2058 and N-tera 2D1.

Figure 14:
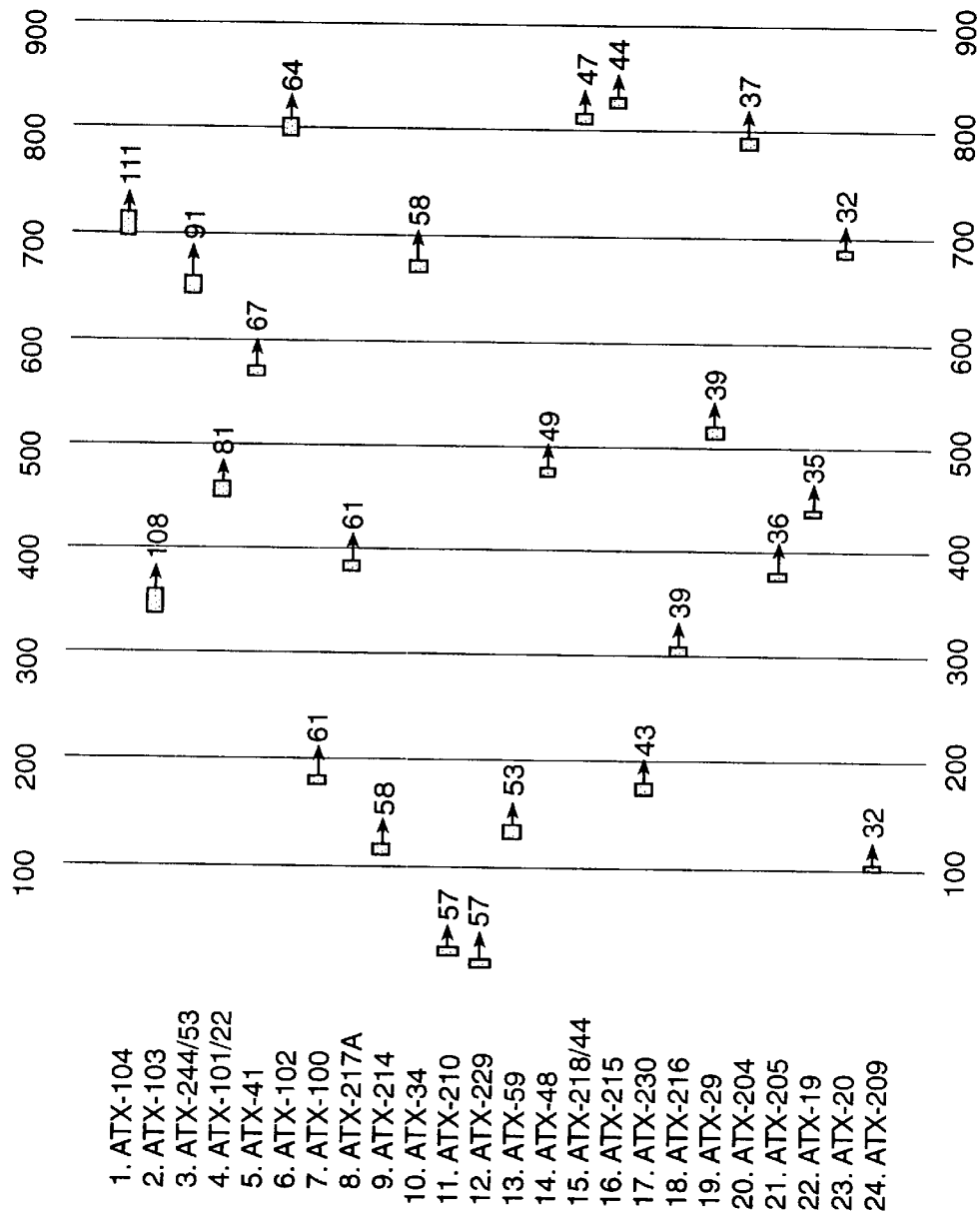

FIG. 14. Schematic match-up of ATX peptides with putative A2058 protein sequence.

Figure 15:
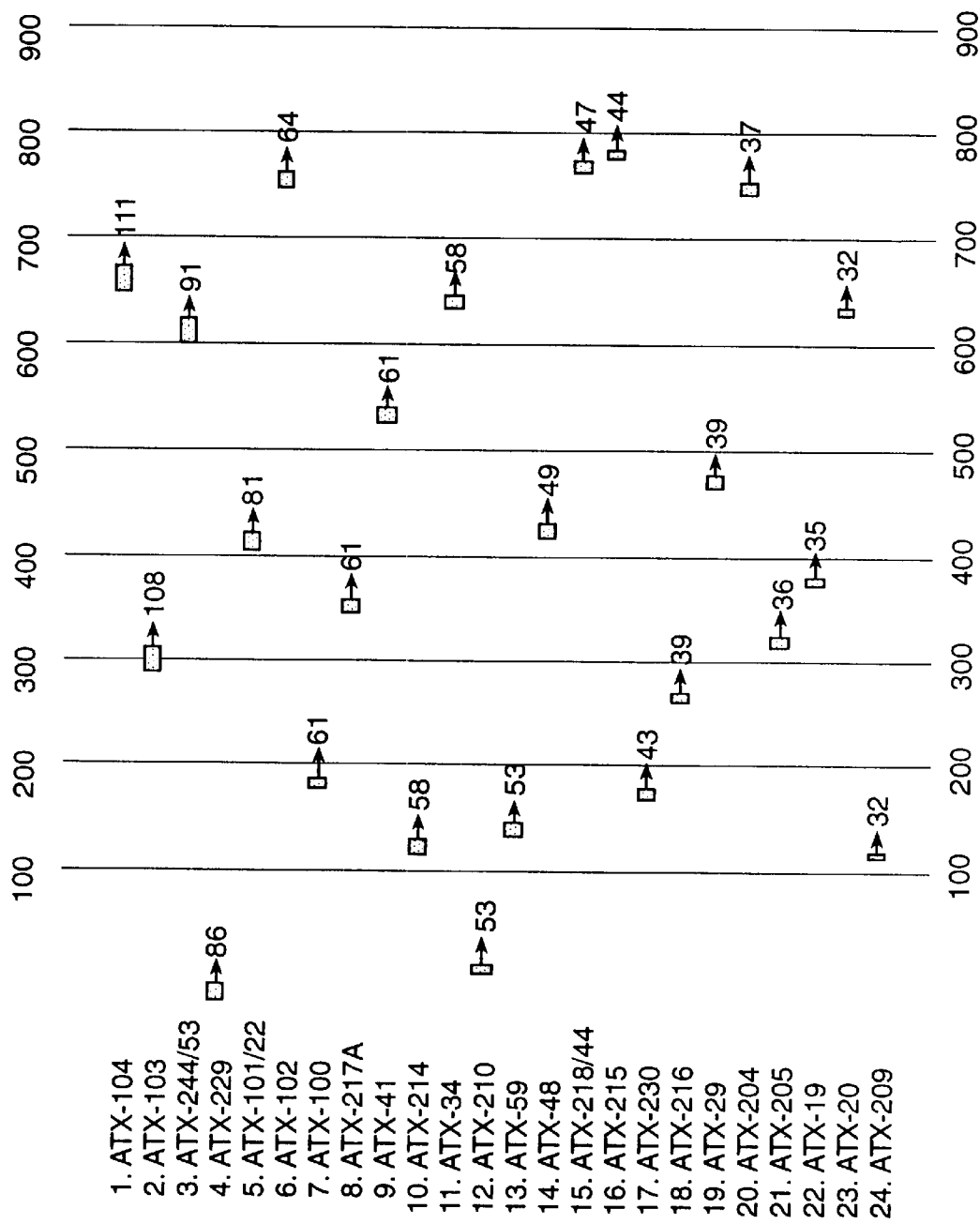

FIG. 15. Schematic match-up of ATX peptides with putative N-tera 2D1 protein sequence.

Figure 16:
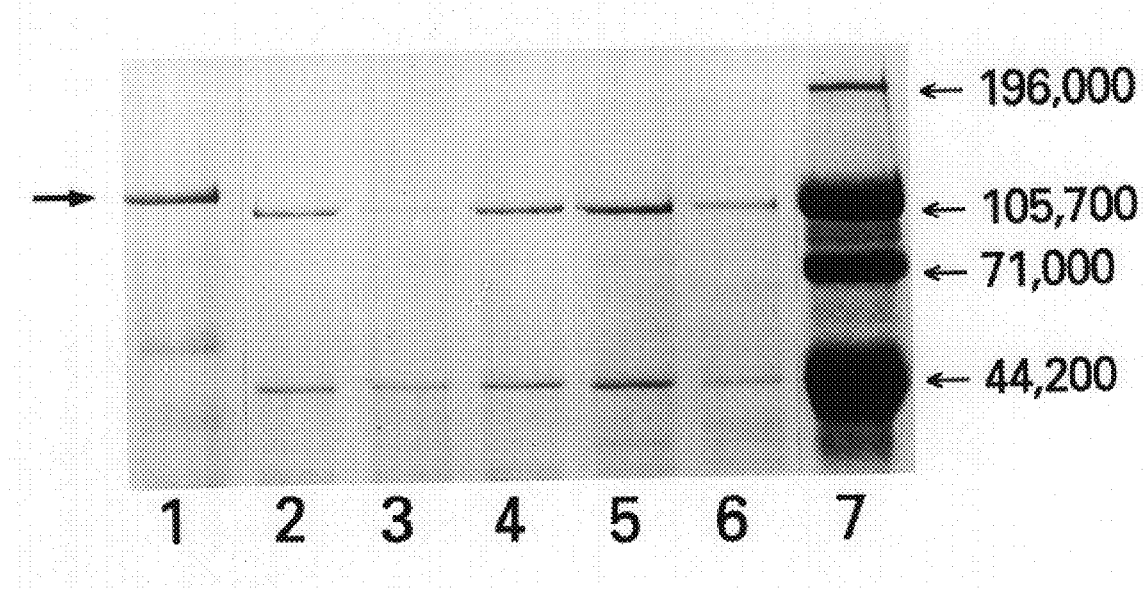

FIG. 16: ATX Treatment with PGNase F.

Partially purified ATX was treated with 60 mU/ml PNGase F at 37° C. for 16 hr under increasingly denaturing conditions. The treated ATX samples were separated by SDS polyacrylamide gel electrophoresis run under reducing conditions and stained with Coomassie blue G-250. Lane 1 contains untreated ATX (arrow) with no enzyme added. Lane 2 contains the reaction mixture run under non-denaturing conditions (50 mM tris/10% ethylene glycol, pH 7). Lanes 3 and 4 have added 0.1 M β-mercaptoethanol and 0.5% Nonidet-P40, respectively. Lanes 5 and 6 contain the reaction mixtures in which the ATX sample was first boiled for 3 min in 0.1% SDS with (lane 6) or without (lane 5) 0.1 M β-mercaptoethanol, then had 0.5% Nonidet-P40 added to prevent enzyme denaturation. The enzyme can be detected as an ~44 kDa band in lanes 2–6.

FIG. 17: Effect of varying concentrations of PNGase F on ATX molecular weight and motility-stimulating activity.

Figure 17A:
Figure 17B:
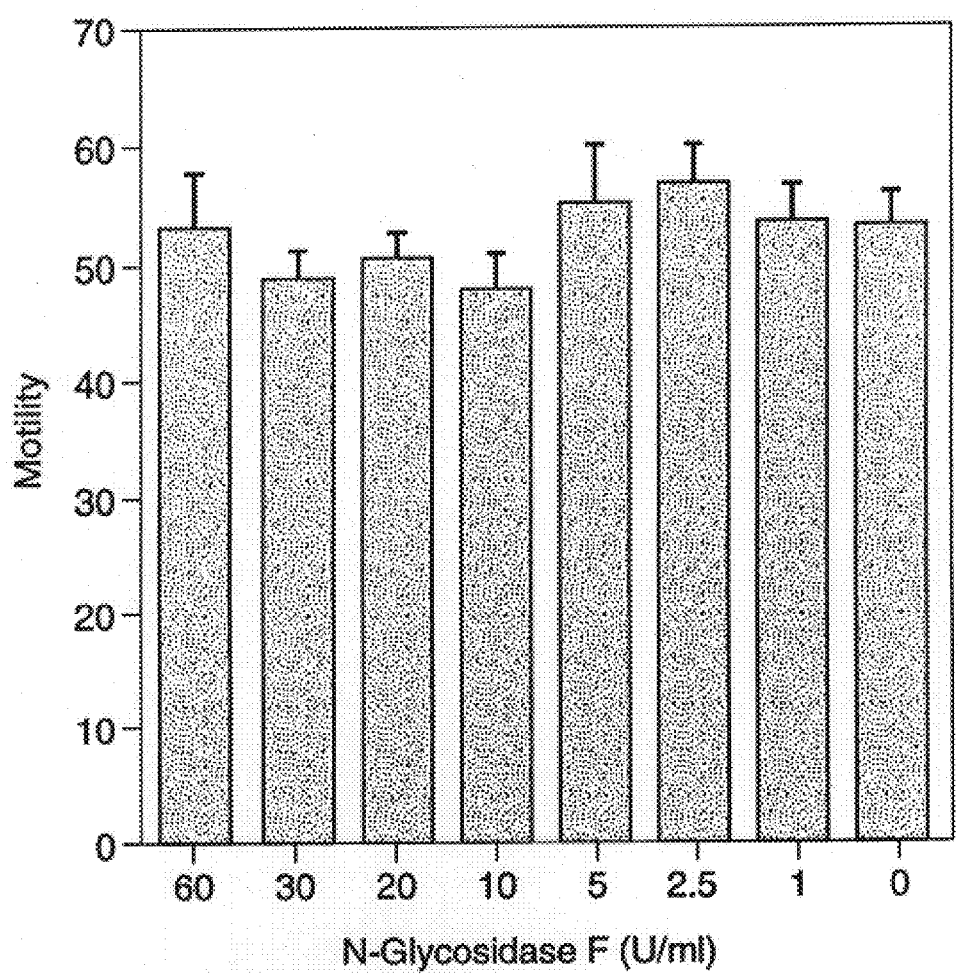

Partially purified ATX was treated with various concentrations (range 0–60 mU/ml, shown on horizontal axis) of PNGase F at 37° C. for 16 hr. FIG. 17A shows the effect of the different treatments on ATX molecular weight. At concentrations of enzyme ≧30 mU/ml, the deglycosylation reaction appears to be complete. FIG. 17B shows the effect of the identical reaction mixtures on motility-stimulating capacity (immediately below the corresponding protein band of FIG. 17A). There is no significant difference between any of the treatment groups.

FIG. 18: Comparison of amino acid sequences of ATX and PC-1. The amino acid sequences of ATX and PC-1 are compared. Amino acid identity is indicated by a vertical line between the sequences. The location of the putative transmembrane/signal sequence is shown by a solid line. The two somatomedin B domains are identified by dashed lines. The putative phosphodiesterase active site is indicated by emboldened lines (residues 201 through 213 of SEQ ID NO:69). The loop region of a single EF hand loop region is identified with double lines. The presumed cleavage site for each protein is indicated with arrows.

FIG. 19: Domain structure of ATX and PC-1. Putative domains are indicated for the two homologous proteins, ATX and PC-1.

DETAILED DESCRIPTION OF THE INVENTION

Tumor cell motility is a critical component of invasion and metatasis, but the regulation of this motility is still poorly understood. At least some tumor cells secrete autocrine motility factors (AMF's) that stimulate motility in the producing cells. Like the analogous autocrine growth factors, these AMF's allow tumor cells independence from the host in this important component of the metastatic cascade. One AMF, autotaxin (ATX), has recently been purified to homogeneity from the human melanoma cell line, A2058 (Stracke, et al., 1992). The purified protein was enzymatically digested and the peptide fragments were separated by reverse phase HPLC. A number of these peptides have been sequenced by standard Edman degradation (Table 6) from different purifications and different enzymatic digestion. Sequence information, obtained initially on 19 purified tryptic peptides, confirmed that the protein is unique with no significant homology to growth factors or previously described motility factors. These peptide sequences have now been used as the basis for identifying and sequencing the cDNA clone for ATX. The present invention comprises an amino acid sequence of ATX as well as a nucleic acid sequence coding for the ATX protein.

TABLE 6

PEPTIDE SEQUENCES FOR AUTOTAXIN.

| PEPTIDE NO. | AMINO ACID SEQUENCE | SEQ ID: NO: |
|---|---|---|
| ATX-18 | WHVAR | SEQ ID NO: 1 |
| ATX-19 | PLDVYK | SEQ ID NO: 2 |
| ATX-20 | YPAFK | SEQ ID NO: 3 |
| ATX-29 | PEEVTRPNYL | SEQ ID NO: 5 |
| ATX-34B | RVWNYFQR | SEQ ID NO: 38 |
| ATX-41 | HLLYGRPAVLY | SEQ ID NO: 29 |
| ATX-48 | VPPFENIELY | SEQ ID NO: 7 |
| ATX-59 | TFPNLYTFATGLY | SEQ ID NO: 32 |
| ATX-100 | GGQPLWITATK | SEQ ID NO: 8 |
| ATX-101/223A | VNSMQTVFVGYGPTFK | SEQ ID NO: 9 |
| ATX-102 | DIEHLTSLDFFR | SEQ ID NO: 10 |

TABLE 6-continued

PEPTIDE SEQUENCES FOR AUTOTAXIN.

| PEPTIDE NO. | AMINO ACID SEQUENCE | SEQ ID: NO: |
|---|---|---|
| ATX-103 | TEFLSNYLTNVDDITLVPETLGR | SEQ ID NO: 11 |
| ATX-104 | VNVISGPIDDYDYDGLHDTEDK | SEQ ID NO: 33 |
| ATX-204 | MHTARVRD | SEQ ID NO: 39 |
| ATX-205 | FSNNAKYD | SEQ ID NO: 40 |
| ATX-209 | VMPNIEK | SEQ ID NO: 41 |
| ATX-210 | TARGWECT | SEQ ID NO: 42 |
| ATX-212 | (N)DSPWT(N)ISGS | SEQ ID NO: 43 |
| ATX-214 | LRSCGTHSPYM | SEQ ID NO: 44 |
| ATX-215/34A | TYLHTYES | SEQ ID NO: 45 |
| ATX-213/217A | AIIANLTCKKPDQ | SEQ ID NO: 46 |
| ATX-216 | IVGQLMDG | SEQ ID NO: 47 |
| ATX-218/44 | TSRSYPEIL | SEQ ID NO: 48 |
| ATX-223B/24 | QAEVSSVPD | SEQ ID NO: 49 |
| ATX-224 | RCFELQEAGPPDDC | SEQ ID NO: 50 |
| ATX-229 | SYTSCCHDFDEL | SEQ ID NO: 51 |
| ATX-244/53 | QMSYGFLFPPYLSSSP | SEQ ID NO: 52 |

ATX is a glycosylated protein due to its high affinity for concanavalin A and amino acid sequence analysis of the ATX peptides. ATX has been demonstrated to be a 125 kDa glycoprotein whose molecular weight reduced to 100–105 kDa after deglycosylation with N-glycosidase F. The calculated molecular weight of the cloned protein is 100 kDa (secreted form) or 105 kDa (full length protein). Based on amino acid composition, the estimated pI is 9.0 which is higher than the pI determined by 2-D gel electrophoresis analysis (7.7–8.0) of purified ATX. This difference can be explained by the presence of sialic acid residues on the sugar moieties.

Autotaxin is secreted by A2058 human melanoma cells cultured in low abundance in serum-free conditioned medium. Autotaxin is a potent new cytokine with molecular mass 125 kDa which has been purified to homogeneity from the conditioned medium of the human melanoma cell line, A2058, utilizing sequential chromatographic methods as described herein. This new cytokine, termed autotaxin (ATX), is a basic glycoprotein with pI~7.8. ATX is active in the high picomolar to low nanomolar range, stimulating both chemotactic and chemokinetic responses in the ATX-producing A2058 cells as well as other tumor cells. This motile response is abolished by pretreatment of the cells with pertussis toxin. ATX may therefore act through a G protein-linked cell surface receptor. These characteristics distinguish ATX from several small growth factors and interleukins which are implicated in tumor cell motility (Stracke et al., 1988; Ruff et al., 1985; Maciag et al., 1984; Gospodarowicz, 1984; Van Snick, 1990; Yoshimura 1987).

The protein of the present invention, which in one embodiment is derived from A2058 human melanoma cells, can be prepared substantially free from proteins with which it is normally associated using, for example, the purification protocol disclosed herein. Alternatively, the protein of the present invention can be prepared substantially free from proteins, by cloning and expressing the cDNA encoding autotaxin as disclosed herein.

A large volume of serum-free conditioned medium from appropriate producer cells (e.g., tumor cells) is collected and concentrated approximately 500-fold. This concentrated conditioned medium is then separated from other contaminating proteins by techniques that rely on the chemical and physical characteristics of the protein. These include the molecular weight, relative hydrophobicity, net charge, isoelectric focusing point, and the presence of lectin-binding sugar residues on the protein.

Alternatively, the protein, or functional portion thereof, can be synthesized using chemical or recombinant means.

The protein of the present invention has a potent biological activity. Purified ATX is active in the picomolar range and 1 unit of activity corresponds to a concentration of approximately 500 pM as assessed by the cell motility assay described herein and elsewhere (Stracke et al., 1989).

The protein of the present invention has a molecular size, as determined by two dimensional gel electrophoresis, of from 120 to 130 kDa, or more specifically, about 125 kDa. Further, the protein of the present invention can have a pI in the range of 7.5 to 8.0, preferably, approximately 7.7. The present invention relates to autotaxin and peptides thereof having cell motility properties as described herein. These proteins and peptides thereof can be produced by isolation from a natural host or isolation as an expression product from a recombinant host.

The present invention also relates to a DNA segment coding for a polypeptide comprising an amino acid sequence corresponding to ATX, or a unique portion of such a sequence (unique portion being defined herein as at least 5, 10, 25, or 50 amino acids). In one embodiment, the DNA segment encodes any one of the amino acid sequences shown in SEQ ID NO:1 to SEQ ID NO:11 and SEQ ID NO:26 to SEQ ID NO:33. Another embodiment uses larger DNA fragments encoding amino acid sequences shown in SEQ ID NO:34, SEQ ID NO: 36 and SEQ ID NO:70. The entire coding region for autotaxin can also be used in the present invention shown in SEQ ID NO:66 through SEQ ID NO:69.

In another embodiment, the present invention relates to a recombinant DNA molecule comprising a vector (for example plasmid or viral vector) and a DNA segment coding for a polypeptide corresponding to ATX, as can be prepared by one skilled in the art. Preferably, the coding segment is present in the vector operably linked to a promoter. The present invention also relates to a recombinant protein produced from a host cell expressing a cDNA containing a coding region of ATX. Examples of ATX cDNAs from a variety of sources have been cloned and can be used for expression, including inter alia A2058 carcinoma cells, N-tera 2D1 cells and human liver.

In a further embodiment, the present invention relates to a cell containing the above-described recombinant DNA molecule. Suitable host cells include procaryotic cells (such as bacteria, including E. coli) and both lower eucaryotic cells (for example, yeast) and higher eucaryotic cells (for example, mammalian cells). Introduction of the recombinant molecule into the host cells can be effected using methods known in the art.

In another embodiment, the present invention relates to a method of producing a polypeptide having an amino acid sequence corresponding to ATX. The method comprises culturing the above-described cells under conditions such that the DNA segment is expressed, and isolating ATX thereby produced.

In a further embodiment, the present invention relates to an antibody having affinity for ATX or peptide fragments thereof. The invention also relates to binding fragments of such antibodies. In one preferred embodiment, the antibodies are specific for ATX peptides having an amino acid sequence set forth in one of SEQ ID NO:1 through SEQ ID NO:11 and SEQ ID NO:26 through SEQ ID NO:34, SEQ ID NO: 36 and SEQ ID NO:38 through SEQ ID NO:52. In addition, the antibodies may recognize an entire autotaxin protein.

Antibodies can be raised to autotaxin or its fragment peptides, either naturally-occurring or recombinantly produced, using methods known in the art.

The ATX protein and peptide fragments thereof described above can be joined to other materials, particularly polypeptides, as fused or covalently joined polypeptides to be used as carrier proteins. In particular, ATX fragments can be fused or covalently linked to a variety of carrier proteins, such as keyhole limpet hemocyanin, bovine serum albumin, tetanus toxoid, etc. See for example, Harper and Row, (1969); Landsteiner, (1962); and Williams et al., (1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., and references cited therein, and in particular in Kohler and Milstein (1975), which discusses one method of generating monoclonal antibodies.

In another embodiment, the present invention relates to an oligonucleotide probe synthesized according to the sense or antisense degenerative sequence set forth in one of SEQ ID NO:1 through SEQ ID NO:11, SEQ ID NO:26 through SEQ ID NO:33, SEQ ID NO:39 through SEQ ID NO:52, and SEQ ID NO:55 through SEQ ID NO:65.

Protein database searches of this sequence revealed a 45% amino acid identity with the plasma cell membrane marker protein, PC-1. ATX and PC-1 appear to share a number of domains, including two somatomedin B domains, the loop region of an EF hand, and the enzymatic site of type I phosphodiesterase/ nucleotide pyrophosphatase. Like PC-1, ATX hydrolyzes p-nitrophenyl thymidine-5'-monophosphate, a type 1 phosphodiesterase substrate. This enzymatic function of ATX suggests a newly identified function for ecto/exo-enzymes in cellular motility.

In a further embodiment, the present invention relates to a method of diagnosing cancer metastasis and to a kit suitable for use in such a method. Preferably, antibodies to ATX can be used in, but not limited to, ELISA, RIA or immunoblots configurations to detect the presence of ATX in body fluids of patients (e.g. serum, urine, pleural effusions, etc.). These antibodies can also be used in immunostains of patient samples to detect the presence of ATX.

In yet another embodiment, the present invention relates to in vivo and in vitro diagnostics. ATX may be radiolabelled, by means known to one skilled in the art, and injected in cancer patients with appropriate ancillary substances also known to one skilled in the art, in order to ultimately detect distant metastatic sites by appropriate imagery. The level of ATX in tissue or body fluids can be used to predict disease outcomes and/or choice of therapy which may also include ATX inhibitors.

In a further embodiment, the present invention relates to a treatment of cancer. ATX antibodies can be cross-linked to toxins (e.g., Ricin A), by means known to one skilled in the art, wherein the cross-linked complex is administered to cancer patients with appropriate ancillary agents by means known to one skilled in the art, so that when the antibody complex binds to the cancer cell, the cell is killed by the cross-linked toxin.

In another embodiment, the different localizations of the normal versus tumorous forms of the ATX proteins within the tissue can be used as a tool for diagnosis and prognosis.

The stage of disease progression can be monitored by elevated levels of ATX in the extracellular space as opposed to its normal cell membranes association. In addition, treatment methods for control of tumor progression can be designed to specifically block the activity of the secreted form of ATX. Such methods would have a preferential effect upon secreted ATX during tumor progression while not effecting normal ATX formation.

Yet another embodiment utilizes the hot spot located in the region from approximately nucleotides 1670 through 1815, as a marker gene for identification of tissues carrying a tumorous form of ATX.

The present invention is described in further detail in the following non-limiting examples.

EXAMPLES

The following protocols and experimental details are referenced in the Examples that follow:

Materials. The polycarbonate Nuclepore membranes and the 48-well microchemotaxis chambers were obtained from Neuro Probe, Inc. Pertussis toxin (PT), ethylene glycol (biotechnology grade), methyl α-D-mannopyranoside were obtained from commercial vendors. The ampholyte, pH 3–10 Bio-Lyte and pH 8–10 Bio-Lyte, were obtained from Bio-Rad. Phenyl Sepharose CL-4B; affi-Gel concanavalin A; ZORBAX BioSeries-WAX (weak anion exchange) column (9.4 mm×24 cm); Spherogel-TSK 4000SW, 3000SW and 2000SW columns (each 7.5 mm×30 cm); the Pro-Pac PA1 (4×50 mm) strong anion exchange column; the Aquapore RP300 C-8 reverse phase column (220×2.1 mm); and the AminoQuant C-18 reverse phase column (200×2.1 mm) were also obtained from commercial sources.

Affi-Gel 10 affinity resin was from Bio-Rad. The Gene-Amp PCR Reagent kit with AmpliTaq and the GeneAmp RNA PCR kit were purchased from Perkin-Elmer. The 5' RACE kit came from Gibco BRL Life Technologies, Inc. The p-nitrophenyl thymidine-5' monophosphate was obtained from Calbiochem Biochemicals.

Ethylene glycol (biotechnology grade) was from Fisher Biochemicals (Pittsburg, Pa.). Peptide N-glycosidase F ("PNGase F"), O-glycosidase, neuraminidase (Arthrobacter ureafaciens), and swainsonine ("Swn") came from Boehringer-Mannheim (Indianapolis, Ind.). 1-Deoxymannojirimycin ("dMAN"), and N-methyl-1-deoxynojirimycin ("NMdNM") were from Oxford GlycoSystems, Inc. (Rosedale, N.Y.). Biotinylated concanavalin A, HRP-conjugated streptavidin, and HRP-conjugated goat anti-rabbit immunoglobulin were purchased from Pierce Chemicals (Rockford, Ill.). Polyvinyl pyrrolidone-free polycarbonate membranes and the microchemotaxis chamber were from NeuroProbe, Inc. (Cabin John, Md.).

Cell Culture. The human melanoma cell line A2058, originally isolated by Todaro (Todaro et al., 1980), was maintained as previously described by Liotta (Liotta et al., 1986). The N-tera 2 (D1 clone) was a kind gift from Dr. Maxine Singer, Laboratory of Biochemistry, National Cancer Institute, National Institutes of Health and was maintained as described (Andrews, P. W., Goodfellow, P. N. and Bronson, D. L. (1983) Cell surface characteristics and other markers of differentiation of human teratocarcinoma cells in culture.).

Production of Autotaxin. A2058 cells were grown up in T-150 flasks, trypsinized, and seeded into 24,000 $cm_2$ cell factories at a cell density of $1\times10^{10}$ cells/factory. After 5–6 days, the serum-containing medium was removed and the cells were washed with DPBS. The factories were maintained in DMEM without phenol red, supplemented with 4 mM glutamine, 100 units/ml penicillin, 100 μg/ml streptomycin, 5 μg/ml crystallized bovine serum albumin, 10 μg/ml bovine insulin, and 1 μM aprotinin. Culture supernatants were harvested every 3 days, frozen at −40° C. and replaced with fresh serum-free medium. Each cycle of supernatant was tested for ATX production with a cell motility assay detailed below. Typically, a cell factory continued to be productive for 9–11 of these cycles.

After accumulation of approximately 45–60 L of supernatant, the culture supernatants were thawed and concentrated down to 2–2.5 L using an Amicon S10Y30 spiral membrane ultrafiltration cartridge. This supernatant was further concentrated in an Amicon high performance ultrafiltration cell using Diaflo membranes. The final volume achieved from 100–200 L of conditioned medium was typically 250–400 ml. All ultrafiltrations were performed at 4° C.

Cell Motility Assays. Purification of autotaxin was monitored by testing the motility-stimulating capacity of the fractions collected from the columns. These fractions were in buffers unsuitable for a chemotaxis assay so each fraction had to be washed into an appropriate buffer, i.e., 0.1% (w/v) BSA in DPBS containing calcium and magnesium. This dialysis was performed by adding aliquots of each fraction to be tested into Centricon-30™ ultrafiltration tubes, which retain molecular species larger than 30,000 daltons.

The assay to determine motility was performed in triplicate using a 48-well microchemotaxis chamber as described elsewhere in detail (Stracke et al., 1987; Stracke, et al., 1989). The Nuclepore™ membranes used in these modified Boyden chambers were fixed and stained with Diff-Quik.™ Chemotaxis was quantitated either by reading the stained membranes with a 2202 Ultroscan laser densitometer or by counting 5 randomly chosen high power fields (HPF) under light microscopy (400×) for each replicate. Densitometer units (wavelength—633 nm) have been shown to be linearly related to the number of cells per HPF (Taraboletti, 1987; Stracke, et al., 1989). Typically, unstimulated motility (background) corresponded to 5–10 cells/HPF and highly responding cells to 70–100 cells/HPF above unstimulated background (i.e., 75–110 total cells/HPF).

For experiments using PT, the toxin was pre-incubated with the cells for 1–2 hr. at room temperature prior to the assay and maintained with the cells throughout the assay (Stracke, et al., 1987). The treated cells were tested for their motility response to the chemoattractant as well as for unstimulated random motility.

Purification of Autotaxin. Ammonium sulfate, to a final concentration of 1.2 M, was added to the concentrated A2058 conditioned medium for 1 hr. at 4° C. The solution was spun in a RC2-B Ultraspeed Sorvall centrifuge at 10,000×g for 15 min. Only the supernatant had the capacity to stimulate motility.

In the first step, the sample was fractionated by hydrophobic interaction chromatography using 200 ml phenyl Sepharose CL-4B column equilibrated into 50 mM Tris (pH 7.5), 5% (v/v) methanol and 1.2 M ammonium sulfate. The supernatant from the ammonium sulfate fractionation was added to this column and eluted using linear gradients of 50 mM Tris (pH 7.5), 5% (v/v) methanol, with decreasing (1.2–0.0) M ammonium sulfate and increasing (0–50) % (v/v) ethylene glycol at 1 ml/min.

The active peak was pooled, dialyzed into 50 mM Tris, 0.1 M NaCl, 0.01 M $CaCl_2$, 20% (v/v) ethylene glycol, and subjected to a second fractionation by lectin affinity chromatography using a 40 ml Affi-Gel concanavalin A column run at 1 ml/min. The sample was eluted in a stepwise fashion in the same buffer with 0, 10, and 500 mM methyl α-mannopyranoside added successively. Fractions from each step of the gradient were pooled and tested for their capacity to stimulate motility.

In the third purification step, the sample that eluted at 500 mM α-methyl-mannopyranoside was dialyzed into 10 mM Tris (pH 7.5) with 30% (v/v) ethylene glycol and fractionated by weak anion exchange chromatography. Chromatography was carried out on a ZORBAX BioSeries-WAX column using a Shimadzu BioLiquid chromatograph and eluted with a linear gradient of (0.0–0.4 M) sodium chloride at 3 ml/min.

The active peak was pooled, dialyzed against 0.1 M sodium phosphate (pH 7.2), 10% (v/v) methanol, and 10% (v/v) ethylene glycol, and subjected to a fourth fractionation step on a series of Spherigel TSK columns (4000SW, 4000SW, 3000SW, 2000SW, in that order). This molecular sieve step was run using the Shimadzu BioLiquid chromatograph at 0.4 ml/min.

The active peak was pooled and dialyzed into 10 mM Tris (pH 7.5), 5% (v/v) methanol, 20% (v/v) ethylene glycol and subjected to a fifth (strong anion exchange) chromatography step, a Pro-Pac PA1 column run at 1 ml/min using a Dionex BioLC with AI450 software. The sample was eluted with a linear gradient of (0.0–0.4M) NaCl.

In order to calculate activity yields after each step of purification, a unit of activity had to be derived. The dilution curve of ATX was biphasic with a broad peak and a linear range at sub-optimal concentrations. One unit of activity/well (i.e., 40 units/ml) was defined as 50% of the maximal activity in a full dilution curve. This allowed calculation of the activity contained in any volume from the dilution needed to achieve 1 unit/well. Therefore, if a 1:10 dilution were needed in order to produce 1 unit of activity/well, the material contained 10×40=400 units/ml.

Gel Electrophoresis. Protein samples were analyzed by SDS-polyacrylamide gel electrophoresis using the conditions of Laemmli (Laemmli, 1970). In brief, 7 or 8% SDS-containing polyacrylamide gels were prepared or pre-poured (8–16%) gradient gels were obtained commercially. Samples were prepared with or without reducing conditions (5% β-mercaptoethanol). After electrophoretic separation, the gels were stained using Coomassie Blue G-250 as previously described (Neuhoff, et al., 1988). In this staining protocol, which ordinarily requires no destaining step, the Coomassie stain appears to be able to stain as little as 10 ng of protein.

For two-dimensional electrophoresis, the protein, in 20% ethylene glycol, was dried in a Speed-vac and redissolved in loading solution: 9M urea, 1% (v/v) pH 3–10 Bio-Lyte, and 2.5% (v/v) Nonidet-P40. This sample was then subjected to isoelectric focusing (O° Farrell, 1975) using a Bio-Rad tube cell in 120×3 mm polyacrylamide tube gels containing 9M urea, 2% (v/v) pH 3–10 Bio-Lyte, 0.25% (v/v) pH 8–10 Bio-Lyte and 2.5% (v/v) Nonidet-P40. Reservoir solutions were 0.01 M phosphoric acid and 0.02 M NaOH. Non-equilibrium isoelectric focusing (O'Farrell, et al., 1977) was run initially with constant voltage (500 v) for 5 hr. Since the protein was basic, the procedure was repeated under equilibrium conditions (500 v for 17 hr.). Electrophoresis in the second dimension was performed on a 7.5% polyacrylamide using the conditions of Laemmli (1970). The gel was stained with Coomassie Blue G-250 as above.

Preparation of peptides for internal sequence of autotaxin. Homogeneous ATX was sequentially digested with cyanogen bromide and, following reduction and pyridylethylation, with trypsin (Stone, et al., 1989). The resulting fragments were then separated by gradient elution on an Aquapore RP300 C-8 reverse phase column: 0.1% (v/v) trifluoroacetic acid and (0–70)% acetonitrile over 85 min. at a flow rate of 0.2 ml/min. A Dionex AI450 BioLC system was utilized and fractions were collected manually while monitoring the absorbance at 215 nm.

Sequence analysis of peptides. The amino acid sequences of peptides resulting from digestion and purification of ATX peptides #1–7 and 12–18, corresponding to SEQ ID NO:1 through SEQ ID NO:7 and SEQ ID NO:26 through SEQ ID NO:32, respectively, were determined on a Porton Instruments 2020 off-line sequenator using standard program #1. Phenylthiohydantoin amino acid analysis of sequenator runs were performed on a Beckman System Gold HPLC using a modified sodium acetate gradient program and a Hewlett-Packard C-18 column. ATX-100 (SEQ ID NO:8), ATX-101 (SEQ ID NO:9), ATX-102 (SEQ ID NO:10), ATX-103 (SEQ ID NO:11) and ATX 104 (SEQ ID NO:33) were sequenced from gel-purified ATX.

Protein databases (Pearson, et al. 1988) that were searched for homologies in amino acid sequence with the ATX peptides include: GenBank (68.0), EMBL (27.0), SWISS-PROT (18.0), and GenPept (64.3).

Example 1

Purification of Autotaxin

The A2058 cells had been previously shown to produce protein factors which stimulate motility in an autocrine fashion (Liotta, et al., 1986). Conditioned medium from these cells was therefore used to identify and purify a new motility-stimulating factor, which is here named autotaxin and referred to as ATX. Since the purification was monitored with a biological assay, motility-stimulating activity had to be maintained throughout. The activity proved to be labile to freezing, acidic buffers, proteases (but not DNase or RNase), reduction, strong chaotrophic agents (e.g. >4 M urea), and a variety of organic solvents (isopropanol, ethanol, acetonitrile). An organic solvent, ethylene glycol, which did not decrease bioactivity, was added for both storage and chromatographic separation.

100–200 L of serum-free conditioned medium were required in order to produce enough ATX for amino acid sequence analysis. The medium contained low concentrations of both BSA (5 μg/ml) which was needed as a carrier protein and insulin (10 μg/ml) which was required to support cell growth in low protein medium. Ultrafiltration to concentrate this large volume was performed with low protein-binding YM30 membranes which retain molecular species with $M_r$>30,000. As seen in Table 1, 200 L of conditioned medium prepared in this manner resulted in 10×10$^6$ units of activity. However, the initial unfractionated conditioned medium contained additional substances known to stimulate activity, particularly insulin, which does not completely wash out in the ultrafiltration step and which is additive to the motility stimulating activity in a complex manner (Stracke, et al., 1989). This had to be taken into account in order to determine yields for subsequent steps in which insulin had been removed.

TABLE 1

PURIFICATION OF AUTOTAXIN

| Purification Step | Protein (mg) | Activity[a] (total units) | Specific Activity (units/mg) | Recovery (%)[b] |
|---|---|---|---|---|
| 200 L Conditioned Medium | 33,000 | 10,000,000[c] | 300 | |
| Phenyl Sepharose | 1,235 | 460,000 | 370 | 100 |
| Concanavalin A | 58 | 660,000 | 11,400 | 100 |
| Weak Anion Exchange | 4.5 | 490,000 | 110,000 | 100 |
| TSK Molecular Sieves | ~0.4[d] | 220,000 | 550,000 | 48 |
| Strong Anion Exchange | ~0.04[d] | 24,000[e] | 600,000 | 5.2 |

[a]Activity calculated from Boyden chamber assay. The dilution which resulted in 50% of maximal activity (generally approximately 20 laser density units or ~40 cells/HPF) was chosen to have 1 unit of activity per well (equivalent to 40 units/ml).
[b]Recovery was estimated from activity, after the first purification column (i.e., phenyl sepharose).
[c]Initial activity in the unfractionated conditioned medium reflected the fact that insulin was used in the medium as a necessary growth factor under low protein conditions.
[d]Estimated protein is based on quantification by amino acid analysis.
[e]This specific activity for purified protein corresponds to ~10 fmol ATX/unit of motility activity (in a Boyden chamber well).

Figure 1:
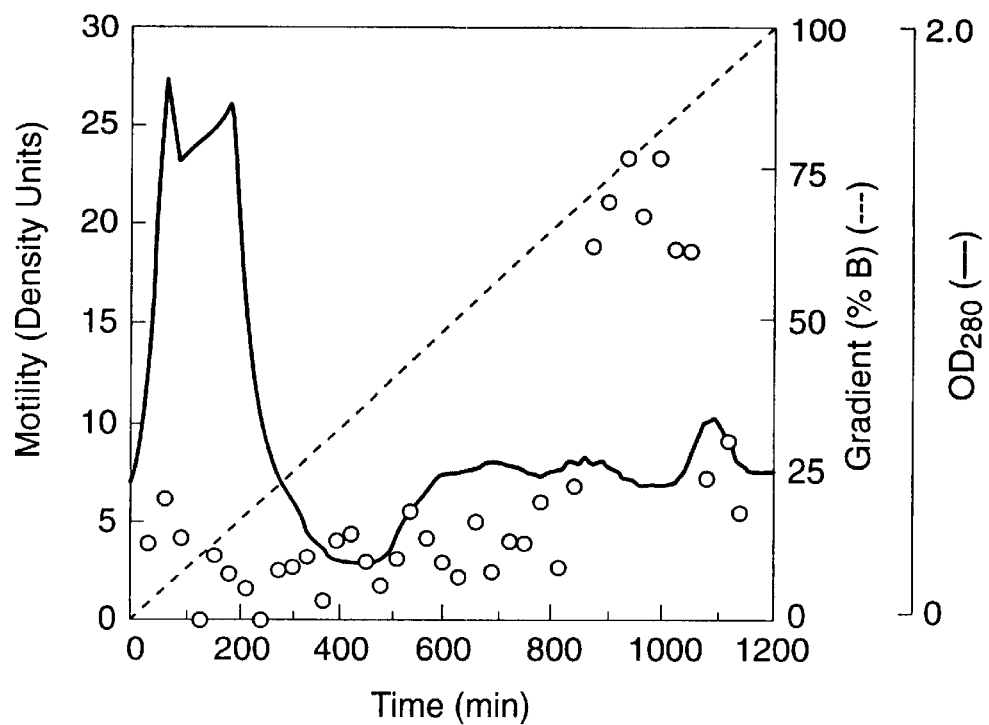
FIG. 1. Fractionation of ATX by hydrophobic interaction. A 200 ml sample of A2058 conditioned media was chromatographed on a 200 mL column of phenyl Sepharose-4B. Buffer A was 50 mM Tris (pH 7.5), 5% methanol, and 1.2 M ammonium sulfate. Buffer B was 50 mM Tris (pH 7.5), 5% methanol and 50% ethylene glycol. The gradient (----) represents a double linear gradient with decreasing ammonium sulfate (1.2 to 0.0 M) and increasing ethylene glycol (0 to 50%). Absorbance was monitored at 280 nm () and indicated that most of the protein did not bind to the column. Ten ml fractions were assayed for motility stimulating capacity using the Boyden Chamber assay (o). The peak of motility activity occurred between 900 and 1050 minutes, ~12% of the gradient.

The first step in the purification involved fractionation by hydrophobic interaction chromatography using a phenyl Sepharose CL-4B column. The results are shown in FIG. 1. Most proteins, including insulin, eluted from the column in early fractions or in the void. However, the peak of activity eluted relatively late. The activity which was purified was estimated as 460,000 units ±20% (Table 1). As the pooled peak of activity from the phenyl Sepharose fractionation is considered to be the first sample without significant insulin contamination, subsequent yields are measured against its total activity. Gel electrophoresis of a small portion of the pooled peak of activity (FIG. 6A, column 2) revealed a large number of protein bands with BSA predominant from the original conditioned medium.

Figure 2:
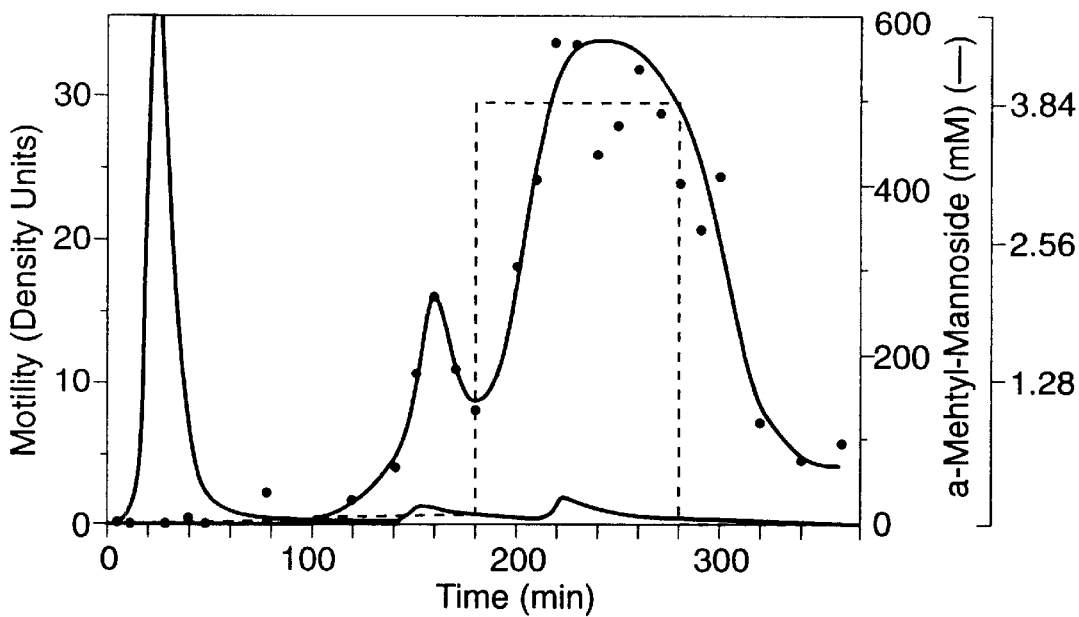
FIG. 2. Isolation of ATX by lectin affinity chromatography. 20 ml portions of the phenyl Sepharose activity peak were affinity purified on a 40 ml concanavalin A Affi-Gel column. The bound components were eluted with a step gradient (----) of methyl α-D-mannopyranoside (0.0 mM, 10 mM, and 500 mM) in a buffer consisting of 0.05 M Tris (pH 7.5), 0.1 M NaCl, 0.01 M $CaCl_2$ and 20% ethylene glycol. Absorbance was monitored at 280 nm () and indicated that the majority of the protein components did not bind to the column. Motility was assayed in 10 mL fractions (...o...) and was found predominantly in the 500 mM elution concentration. One of seven chromatographic runs is shown.

In the second step of purification, the active peak was applied to the lectin affinity column, Affi-Gel concanavalin A. As shown in FIG. 2, most protein (estimated to be 90% of the total absorbance at 280 nm) failed to bind to the column at all. The non-binding fraction contained essentially no motility-stimulating activity (see dotted line in FIG. 2). When a linear gradient of methyl α-D-mannopyranoside was applied to the column, chemotactic activity eluted off in a prolonged zone, beginning at a concentration of approximately 20 mM sugar. Consequently, a step gradient was used to elute. Pure BSA failed to bind to con A.

Activity was found primarily in the 500 mM step of methyl α-D-mannopyranoside. There appeared to be no significant loss of activity as seen in Table 1; however, specific activity (activity/mg total protein) increased thirty-fold. Gel electrophoresis of the pooled and concentrated peak (FIG. 6A, column 3) revealed that the BSA overload was no longer apparent and the number of bands were much reduced. When the unbound protein was concentrated and applied to a gel, it appeared identical to the active peak from phenyl Sepharose-4B with a large BSA band.

Figure 3:
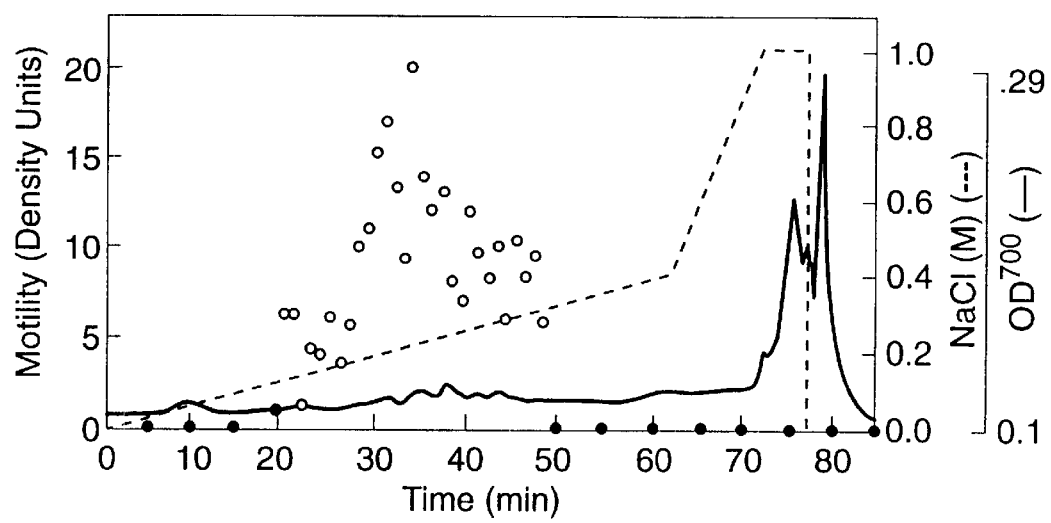
FIG. 3. Purification of ATX by weak anionic exchange chromatography. Approximately 30% of the activity peak eluted from the Con A affinity column was applied to a ZORBAX BioSeries-WAX column. The bound components were eluted with an NaCl gradient (----) in a buffer consisting of 10 mM Tris (pH 7.5) and 30% ethylene glycol. Motility (o) was assayed in 1.0 ml fractions. The peak of activity eluted in a discrete but broad region in the shallow portion of the gradient. Absorbance was monitored at 230 nm (). The majority of the protein components not associated with activity bound strongly to the column were eluted at 1.0 M NaCl. One of two chromatographic runs is shown.
Figure 6A:
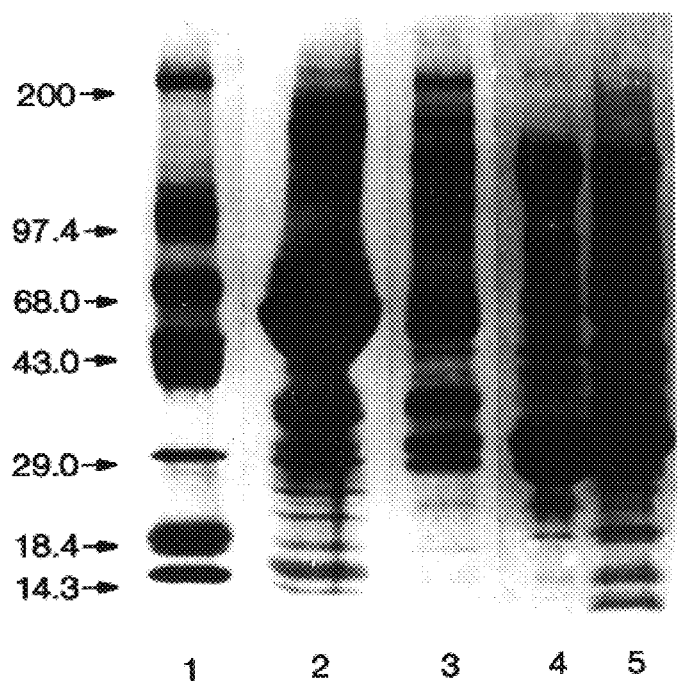
FIGS. 6A, 6B and 6C. Protein components associated with the activity peaks from various stages of purification. The activity peak from each chromatographic fractionation was pooled, concentrated and analyzed by SDS-polyacrylamide gel electrophoresis. Molecular weight standards are in Lane 1 for each panel. Panel 6A) 8–16% gradient gel of the first three purification steps, run under non-reducing conditions. Lane 2 is an aliquot of the pooled activity peak eluted from the phenyl sepharose fractionation. Lane 3 is an aliquot of the pooled activity peak eluted from the Con A affinity purification. Lanes 4 and 5 show the "peak" and "shoulder" of activity fractionated by weak anion exchange chromatography (FIG. 3). Panel 6B) 7% gel of the activity peak fractionated by molecular sieve exclusion chromatography. Lanes 2 and 3 show the protein separation pattern of the total pooled activity peak when the gel was run under non-reducing and reducing conditions, respectively. Panel 6C) 8–16% gradient gel of the final strong anionic exchange chromatographic separation, run under non-reducing conditions. Lane 2 comprises ~1% of the total pooled activity peak eluted from the column.

The third purification step involved fractionating the previous active peak by weak anion exchange chromatography as shown in FIG. 3. Under the running conditions, activity eluted in a broad peak-shoulder or double peak in the middle of the shallow portion (0.0–0.4 M) of the NaCl gradient. The largest proportion of protein, lacking in motility-stimulating capacity, bound strongly to the column and eluted off in high salt (1 M NaCl). There appeared to be no significant loss of activity, though specific activity increased by twenty-fold (Table 1). Analysis by gel electrophoresis of both the peak (28–34 min. in FIG. 3) and the shoulder (35–45 min. in FIG. 3) is shown in FIG. 6A (columns 4 and 5, respectively). Two predominant protein bands resulted: a broad doublet around 25–35 kDa and a second doublet around 110–130 kDa.

Figure 4:
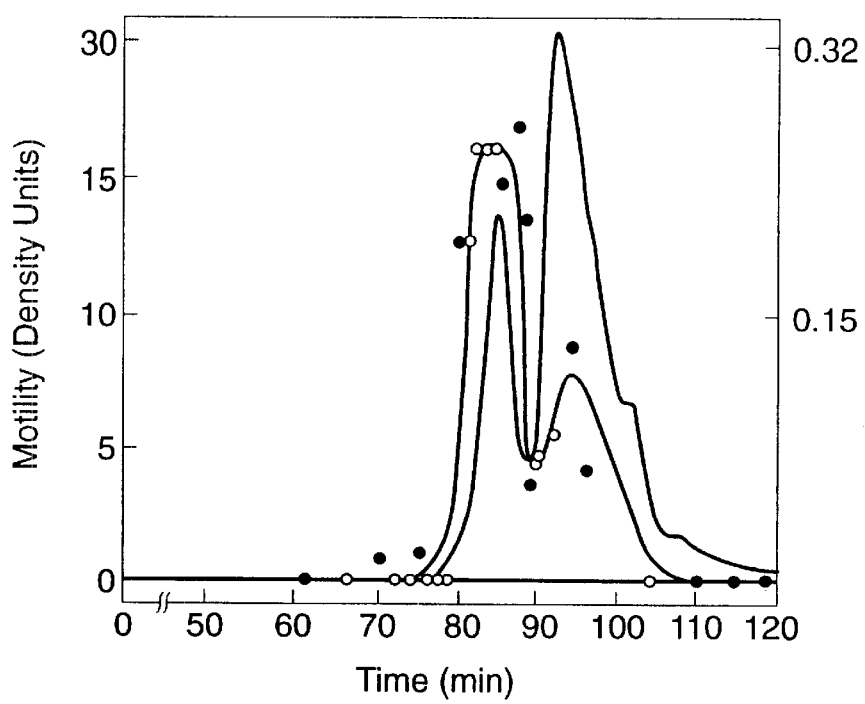
FIG. 4. Purification of ATX by molecular sieve exclusion chromatography. The entire activity peak eluted from the weak anion exchange column was applied to a series of TSK columns (4000SW, 4000SW, 3000SW, and 2000SW, in this order). Proteins were eluted in a buffer consisting of 0.1M $NaPO_4$ (pH 7.2) with 10% methanol and 10% ethylene glycol. Two major protein peaks were evident by monitoring the absorbance at 235 nm (). Motility (...o...) was assayed in 0.4 ml samples and found predominantly in the first, smaller, protein peak.
Figure 6B:
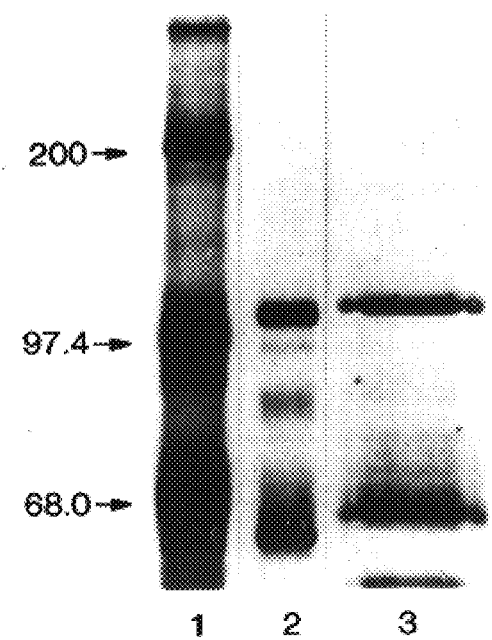

In the fourth purification step, the active peak was applied to a series of molecular sieves. Spectrophotometric monitoring of the eluant revealed two large peaks of protein (FIG. 4). Activity corresponded to the first, higher molecular weight peak. Recovery of activity was ~48% with a five-fold increase in specific activity. Analysis by gel electrophoresis was performed under non-reducing and reducing conditions as shown in FIG. 6B (columns 2 and 3, respectively). This fractionation step had essentially removed all contaminating protein of molecular weight<55 kDa. The predominant band remaining has a molecular weight of 120 kDa unreduced and 125 kDa reduced; there are two minor bands with molecular weights 85 kDa and 60 kDa. The fact that the 120 kDa protein changes so little in electrophoretic mobility after reduction would tend to indicate a paucity of disulfide bonds. However, the existing disulfide bonds have functional significance because motility-stimulating activity is labile to reduction.

Figure 5:
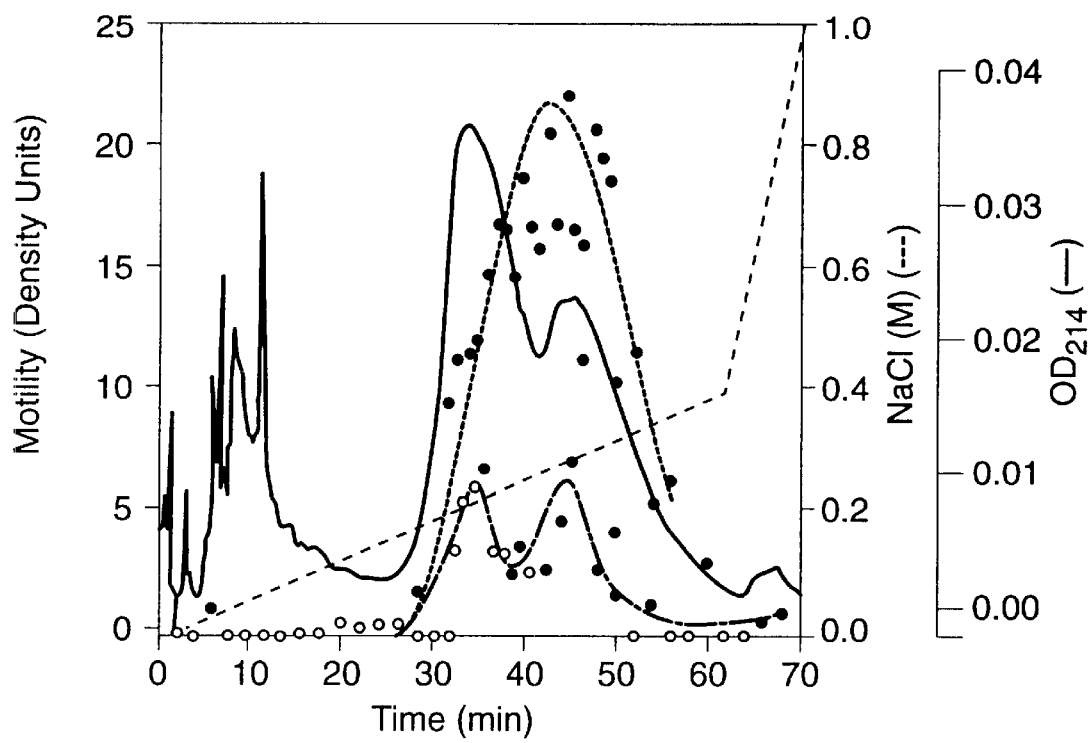
FIG. 5. Final purification of ATX by strong anionic exchange chromatography. Approximately 15% of the activity peak from the molecular sieve exclusion series was applied to a Pro-Pac PA1 column. Protein which bound to the column was eluted with a NaCl gradient (----) in a buffer consisting of 10 mM Tris (pH 7.5), 5% methanol and 20% ethylene glycol. Absorbance was monitored at 215 nM (). Motility activity was assayed in 1.0 ml fractions at two different dilutions: ⅕ (...o...) or ⅟₁₅ (..o..). Activity was found to correspond to a double protein peak in the central region of the gradient.
Figure 6C:

The fifth purification step involved fractionation of the active peak by strong anion exchange chromatography. As shown in FIG. 5, activity corresponds to two broad optical absorbance peaks in the middle of the gradient with contaminating proteins eluting earlier. These two peaks were identical by amino acid analysis and by polyacrylamide gel electrophoretic separation. They presumably represent different glycosylation states of the same parent protein. Activity is shown in FIG. 5 at two different sample dilutions. Several dilutions of the fractionated samples were often necessary in order to resolve the true "peak" of activity as the shape of the ATX dilution curve was not sharp due to saturation and down regulation at high concentrations. Recovery from this chromatographic step is lower (5% compared to phenyl Sepharose), as might be expected when a minute quantity of protein is applied to a column; however, specific activity again increased (Table 1). Analysis by gel electrophoresis revealed a single protein band at molecular weight 120 kDa, unreduced (FIG. 6C, column 2).

Example 2

Characterization of Autotaxin

Two dimensional gel electrophoresis of the purified protein (FIG. 7) revealed a single predominant band. The band slopes downward slightly toward the basic side of the gel in a manner that is characteristic of glycosylated proteins. A basic pI of 7.7±0.2 was essentially the same whether the isoelectric focusing was run under non-equilibrium conditions (5 hr.) or was allowed to go to equilibrium (17 hr.).

Figure 8:
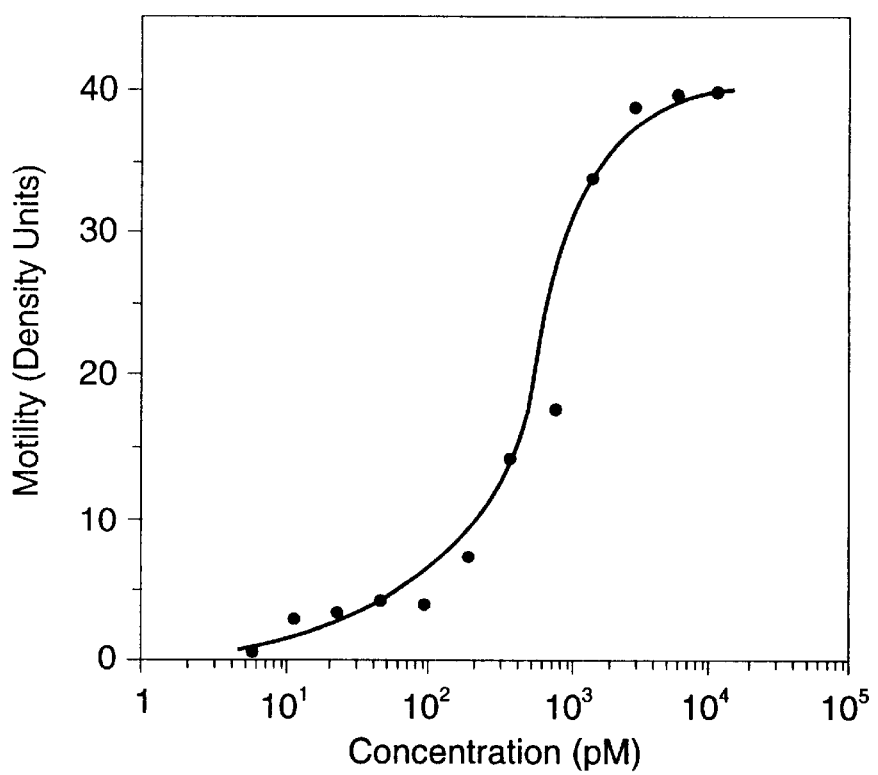
FIG. 8. Dilution curve of ATX. Purified ATX (FIG. 6, Panel C) was serially diluted and tested for motility-stimulating activity. The result, with unstimulated background motility subtracted out, shows that activity is half-maximal at ~500 pM ATX.
Figure 9:
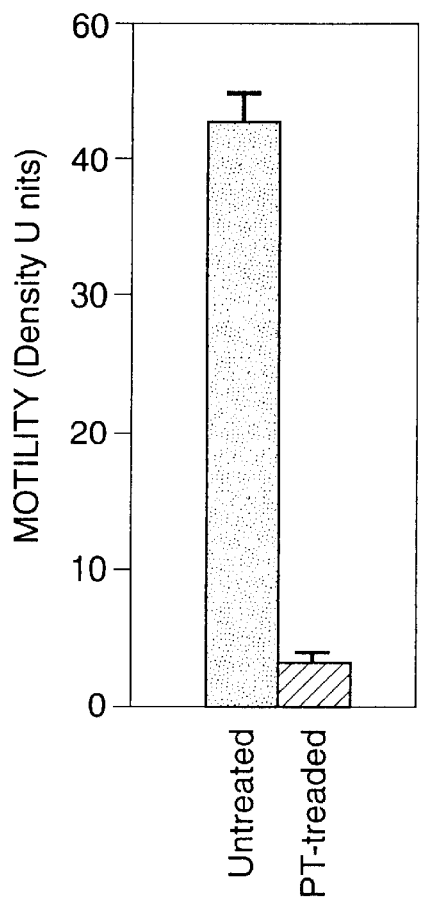
FIG. 9. Pertussis toxin (PT) sensitivity of ATX. A2058 cells were pre-treated for 1 hr. prior to the start of the motility assay with 0.5 μg/ml PT in 0.1% BSA-DMEM or with 0.1% BSA-DMEM alone (for untreated control). The motility activity stimulated by purified ATX (FIG. 6, Panel C) was then assessed for the two treatment groups. The result, expressed as cells/HPF±S.E.M. with unstimulated background motility subtracted out, reveals profound inhibition of PT-treated cells (hatched) compared to untreated cells (solid). PT had no effect on cell viability. S.E.M.'s were <10%.

A dilution curve of the purified protein is shown in FIG. 8. The protein is active in the picomolar range and 1 unit of activity appears to correspond to a concentration of 400–600 picomolar (or approximately 10 fmol of ATX/Boyden chamber well). When dilutions were begun at higher concentrations of ATX, the resultant curve showed a broad plateau with down-regulation at the highest concentrations. The motility response to purified autotaxin is highly sensitive to pertussis toxin (hereinafter referred to as "PT") (Table 2 and FIG. 9) with approximately 95% inhibition of activity at 0.5 μg/ml PT.

TABLE 2

Effect of Pertussis Toxin (PT) on Autotaxin-stimulated motility

| | A2058 Motility Response (density units[1]) | |
|---|---|---|
| | control cells[2] | Pertussis toxin-treated cells[3] |
| Condition medium[4] | 60.3 | 0.4 |
| Purified Autotaxin | 38.5 | 0.0 |

Chemotaxis quantitated by motility assay (Stracke, et al., 1978).
[2]A2058 cell suspended at 2 × 10⁶ cells/ml in DMEM supplemented with 1 mg/ml bovine serum and rocked at room temperature for 1 hr.
[3]As control with 0.5 μg/ml pertussis toxin.
[4]Prepared by adding DMEM without phenol red supplemented with 0.1 mg/ml bovine serum albumin to subconfluent flasks of A2058 cells. The medium was harvested after 2 days incubation at 37° C. in a humidified atmosphere and concentrated 25–30 fold using an Amicon ultrafiltration assembly with a YM-30 membrane.

Figure 10:
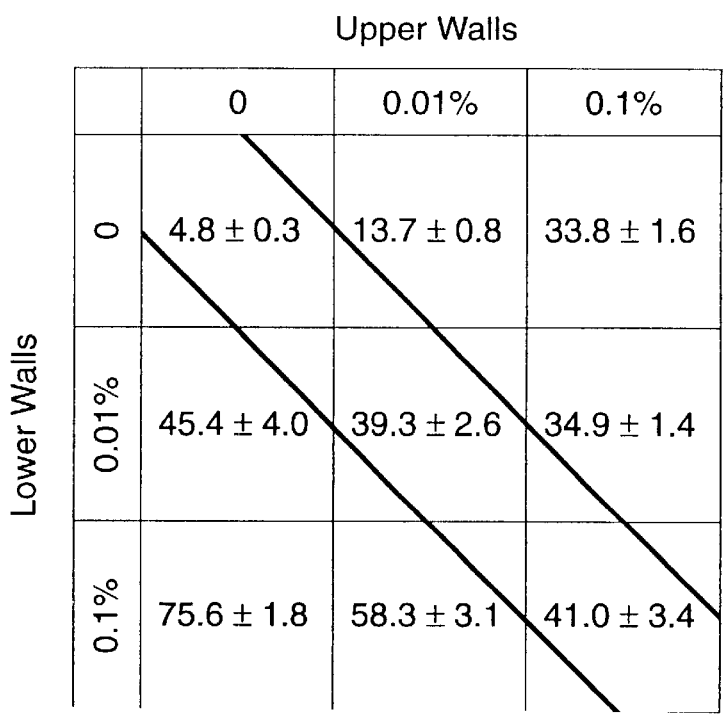
FIG. 10. Checkerboard analysis of ATX-stimulated motility. Varying dilutions of autotaxin were added to the upper chamber with the cells and/or to the lower chamber, as shown. Motility response, expressed as cells/HPF±S.E.M., was assessed for each point in the checkerboard.

Checkerboard analysis was performed to assess the random (chemokinetic) versus the directed (chemotactic) nature of the motility response to ATX. Chambers were assembled with different concentrations of ATX above and below the filter, using ATX purified through the weak anion exchange fractionation step. Squares below the diagonal reflect response to a positive gradient, squares above reflect response to a negative gradient, and squares on the diagonal reflect random motility in the absence of a gradient. ATX stimulates both chemotactic and chemokinetic responses (FIG. 10), with chemotactic responses as high as fifteen-fold above background and chemokinesis as high as eight-fold above background.

Amino acid analysis after complete acid hydrolysis was used to quantitate purified protein. This hydrolysis was carried out on protein excised from a polyacrylamide gel and presumed to be pure. The analysis indicated that 2.7 nmol of protein was present after fractionation on the molecular sieve. After fractionation by strong anion exchange chromatography, approximately 300 pmol remained. The results of the analysis are shown in Table 3.

TABLE 3

AMINO ACID COMPOSITION OF AUTOTAXIN
(CYS and TRP were not determined in this analysis)

| Amino Acid | Residues/100 |
|---|---|
| ASX | 12.5 |
| THR | 6.0 |
| SER | 5.7 |
| GLX | 9.4 |
| PRO | 7.4 |
| GLY | 7.0 |
| ALA | 3.9 |
| VAL | 6.7 |
| MET | 1.2 |
| ILE | 4.3 |
| LEU | 9.0 |
| TYR | 5.2 |
| PHE | 5.2 |
| HIS | 3.8 |
| LYS | 7.4 |
| ARG | 5.4 |

Example 3

ATX Degradation and Determination of Amino Acid Sequence

Figure 11:
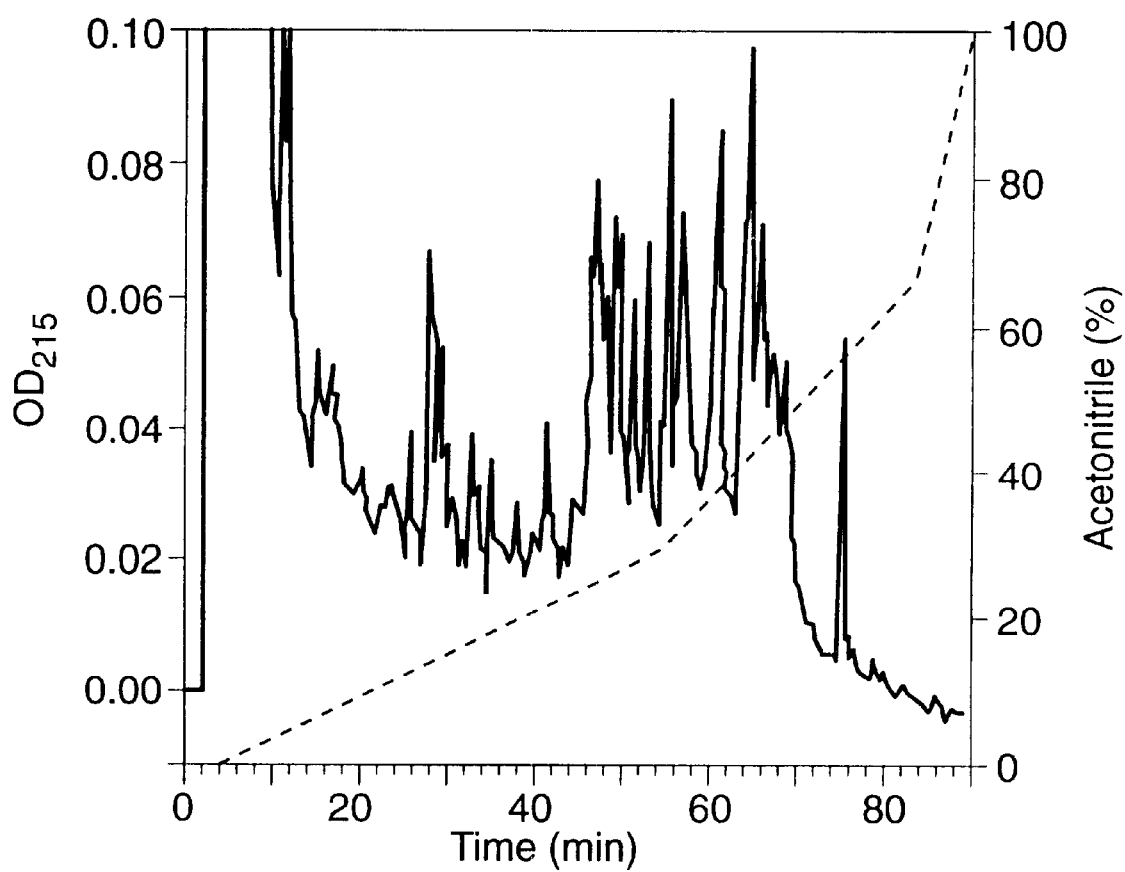
FIG. 11. Purification of ATX peptides on HPLC. ATX, purified to homogeneity by strong anionic exchange chromatography, was sequentially digested by cyanogen bromide, subjected to reduction and pyridylethylation, and digested by trypsin. The resulting peptides were purified on an Aquapore RP300 C-8 reverse phase column using a (0–70)% acetonitrile gradient in 0.1% trifluoroacetic acid (----). The absorbance was monitored at 215 nm () and peaks were collected. Seven peaks, chosen at random for N-terminal amino acid sequence analysis, are shown with appropriate numbers.

Attempts to obtain N-terminal sequence information from purified ATX repeatedly proved futile. The purified protein was therefore, sequentially digested and the resulting peptides fractionated by reverse phase chromatography. The results are shown in FIG. 11. Multiple sharp peaks including clusters at both the hydrophilic and hydrophobic ends of the gradient are seen.

Several of these peptide peaks were chosen randomly for Edman degradation and N-terminal amino acid sequence analysis. Seven of the eight peaks (shown in FIG. 11) chosen gave clear single sequence information as seen in Table 4. Using material from a separate digestion and purification, the remaining four sequences were also obtained.

Separate sense and antisense oligonucleotide probes were synthesized according to the fragment sequences of Table 4 by methods known to one skilled in the art. Representative probes are shown in Table 5.

TABLE 4

Peptide sequences for Autotaxin.

| PEPTIDE NO. | AMINO ACID SEQUENCE | SEQ ID: NO: | NAME |
|---|---|---|---|
| 1. | WHVA | SEQ ID NO: 1 | ATX 18 |
| 2. | PLDVYK | SEQ ID NO: 2 | ATX 19 |
| 3. | YPAFK | SEQ ID NO: 3 | ATX 20 |
| 4. | QAEVS | SEQ ID NO: 4 | ATX 24 |
| 5. | PEEVTRPNYL | SEQ ID NO: 5 | ATX 29 |
| 6. | YDVPWNETI | SEQ ID NO: 6 | ATX 47 |
| 7. | VPPFENIELY | SEQ ID NO: 7 | ATX 48 |
| 8. | GGQPLWITATK | SEQ ID NO: 8 | ATX 100 |
| 9. | VNSMQTVFVGY-GPTFK | SEQ ID NO: 9 | ATX 101 |
| 10. | DIEHLTSLDFFR | SEQ ID NO: 10 | ATX 102 |
| 11. | TEFLSNYLTNVDD-ITLVPETLGR | SEQ ID NO: 11 | ATX 103 |
| 12. | QYLHQYGSS | SEQ ID NO: 26 | ATX 37 |
| 13. | VLNYF | SEQ ID NO: 27 | ATX 39 |
| 14. | YLNAT | SEQ ID NO: 28 | ATX 40 |
| 15. | HLLYGRPAVLY | SEQ ID NO: 29 | ATX 41 |
| 16. | SYPEILTPADN | SEQ ID NO: 30 | ATX 44 |
| 17. | XYGFLFPPYLSSSP | SEQ ID NO: 31 | ATX 53 |
| 18. | TFPNLYTFATGLY | SEQ ID NO: 32 | ATX 59 |
| 19. | VNVISGPIFDYDYDGLH DTEDK | SEQ ID NO: 33 | ATX 104 |

Peptide numbers 1–7 refer to peaks numbered in FIG. 11. Peptide numbers 12–18 refer to peptides purified from the preparation which yielded peptide numbers 1–7. Peptides 8–11 and 19, are from a separate purification, not shown in FIG. 11.

X refers to potentially glycosylated residues.

TABLE 5

Oligonucleotides synthesized from peptide sequences of autotaxin (ATX). The number of the oligonucleotide corresponds to the ATX peptide number as per Table 4. The final letter suffix distinguishes whether the oligonucleotide is a sense (S) or antisense (A) sequence.

| Oligo | Sequence | SEQ ID NO: |
|---|---|---|
| A-18A | GTT-GGC-AGC-NAC-RTG-CCA | SEQ ID NO:12 |
| A-18S | TGG-CAY-GTN-GCT-GCC-AAC | SEQ ID NO:13 |
| A-20A | CTT-GAA-GGC-AGG-GTA | SEQ ID NO:14 |
| A-20S | TAY-CCT-GCN-TTY-AAG | SEQ ID NO:15 |
| A-29A | GGT-NAC-YTC-YTC-AGG | SEQ ID NO:16 |
| A-29S | CCT-GAR-GAR-GTN-ACC | SEQ ID NO:17 |
| A-47A | NGT-NGC-RTC-RAA-TGG-CAC-RTC | SEQ ID NO:18 |
| A-47S | GAY-GTG-CCA-TTY-GAY-GCN-ACN | SEQ ID NO:19 |
| A-48A | GTT-DAT-RTT-STC-RAA-TGG-GGG | SEQ ID NO:20 |
| A-48S | CCC-CCA-TTT-GAG-AAC-ATC-AAC | SEQ ID NO:21 |

TABLE 5-continued

Oligonucleotides synthesized from peptide sequences of autotaxin (ATX). The number of the oligonucleotide corresponds to the ATX peptide number as per Table 4. The final letter suffix distinguishes whether the oligonucleotide is a sense (S) or antisense (A) sequence.

| Oligo | Sequence | SEQ ID NO: |
|---|---|---|
| A-100A | CTT-NGT-NGC-NGT-DAT-CCA-NAR-GGG-YTG-GCC-GCC | SEQ ID NO:22 |
| A-100S | GGC-GGC-CAR-CCC-YTN-TGG-ATH-ACN-GCN-ACN-AAG | SEQ ID NO:23 |
| A-101A | CTT-RAA-GGT-GGG-GCC-RTA-GCC-CAC-RAA-GAC-TGT-YTG-CAT | SEQ ID NO:24 |
| A-101S | ATG-CAR-ACA-GTC-TTY-GTG-GGC-TAY-GGC-CCC-ACC-TTY-AAR | SEQ ID NO:25 |

Example 4

Antipeptide Antibodies

Rabbits were injected with ATX-101 (SEQ ID NO:10) which had been cross-linked to bovine serum albumin. Antisera from these rabbits was subjected to salt precipitation followed by purification using affinity chromatography with Affi-Gel 10 beads covalently linked to the peptide, ATX-101 (SEQ ID NO:10). This affinity purified antibody reacted with the partially purified protein on immunoblots. This same antibody has been used to perform immunohistochemical stains on human tissue.

Example 5

Enzymatic Deglycosylation of ATX

Purified ATX that was to be treated with peptide N-glycosidase F (PNGase F) was first dialyzed into 0.2 M sodium phosphate, 10% (v/v) ethylene glycol pH 7.0, using Centricon-30 ultrafiltration tubes. Varying concentrations of PNGase F were added to the ATX and incubated 16–18 hr. at 37° C. Complete digestion appeared to occur at concentrations of enzyme above 30 mU/ml (where 1 U converts 1 mmol of substrate/min). For comparison, the experiments were repeated in the presence of 0.1 M β-mercaptoethanol or 0.1% (w/v) SDS plus 0.5% (v.v) Nonidet-P40. ATX that was to be treated with neuraminidase or O-glycosidase was dialyzed into 20 mM sodium phosphate, 0.1 M calcium acetate, and 10% (v/v) ethylene glycol (pH 7.2). Neuraminidase was added to a final concentration of 2 U/ml. For treatment with neuraminidase alone, this mixture was incubated 16–18 hr at 3° C. Since O-glycosidase requires the removal of terminal sialic acid residues for efficient deglycosylation, ATX was pre-incubated with neuraminidase for 30–125 mU/ml and incubated 16–18 hr. at 37° C. The treated ATX was then dialyzed into 50 mM Tris with 20% ethylene glycol for storage at 5%C.

Treatment of ATX with N-glycosylation Altering Agents

A2058 cells were split into four 150 $cm^2$ flasks and incubated until just subconfluent in DMEM supplemented with 10% fetal calf serum. The medium was then replaced with fresh 10% FCS/DMEM to which had been added DPBS for control, 1 mM dMAN, 1 mM NMdNM, or 10 mM (1.7 mg/ml) Swn. Concentrations of these pharmacological agents were similar to those previously described as inhibiting N-glycan processing enzymes in melanoma cells (Seftor, et al. 1991; Dennis, et al. 1990) as well as carcinoma cells (Ogier, et al. 1990). On the next day, each flask was washed twice with Dulbecco's phosphate buffered saline with calcium ("DPBS") then 20 ml of Dulbecco's minimum essential medium ("DMEM") supplemented with 0.01% (w/v) bovine serum albumin ("BSA") was added. The same concentration of each agent was added to the appropriate equilibrated flask and incubated for ~24 hr, after which the medium from each treatment group was collected, concentrated, washed into DPBS and stored at 5° C.

Cells from each flask were trypsinized and counted. There was no loss of viability or reduced cell number in any of the treatment groups compared to control cells.

Effect of PNGase F on ATX

ATX binds to concanavalin A ("Con A") agarose beads and is eluted with buffer containing 0.5 M methyl a-D-mannopyranoside, indicating that ATX is likely to contain mannose residues. Such mannose sugar residues are most characteristic of N-linked oligosaccharides. In order to verify that ATX contained asparagine-linked oligosaccharides, we treated it with the endoglycosidase, PNGase F, which cleaves high mannose, hybrid, and complex N-linked oligosaccharides at the asparagine residue.

Partially purified ATX was treated with 60 mU/ml of enzyme under a variety of increasingly denaturing conditions and then separated by polyacrylamide gel electrophoresis (FIG. 16). Lane 1 shows untreated material; the 125 kDA band (arrow) is autotaxin. When this material is treated overnight with PNGase F under very mild conditions, the size of the 125 kDa band decreases to ~100–105 kDa. Addition of 0.1 M b-mercaptoethanol (Lane 2) or 0.5% Nonidet-P40 (lane 3) to the ATX sample has no effect on the size of the resultant protein band. Even complete denaturation of ATX of boiling the sample for 3 min in 0.1% SDS with (lane 5) or without (lane 4) β-mercaptoethanol, followed by addition of 0.5% Nonidet-P40 to maintain enzymatic activity, has no effect on the final size of deglycosylated protein, indicating that the deglycosidation reaction was complete even under mild conditions.

Because these results showed that ATX contained N-linked oligosaccharide groups, it became important to see if these sugar moieties were necessary for stimulation of motility. The partially purified ATX sample was treated with varying concentrations of PNGase F (0.1 to 60 mU/ml) under mild, non-denaturing conditions. Analysis of the resulting digest by polyacrylamide gel electrophoresis is shown in FIG. 17A. As this figure shows, the digestion was incomplete using from 0.1 to 10 mU/ml of enzyme and resulted in a smear of protein between 100–125 kDa. However, at higher concentrations of enzyme, cleavage of N-linked oligosaccharides from ATX appears to be complete. When these different digestion products were compared for their capacity to stimulate motility (FIG. 17B), there was no significant difference between groups.

Example 6

Cloning the 3' End of Autotaxin (4C11)

Figure 12:
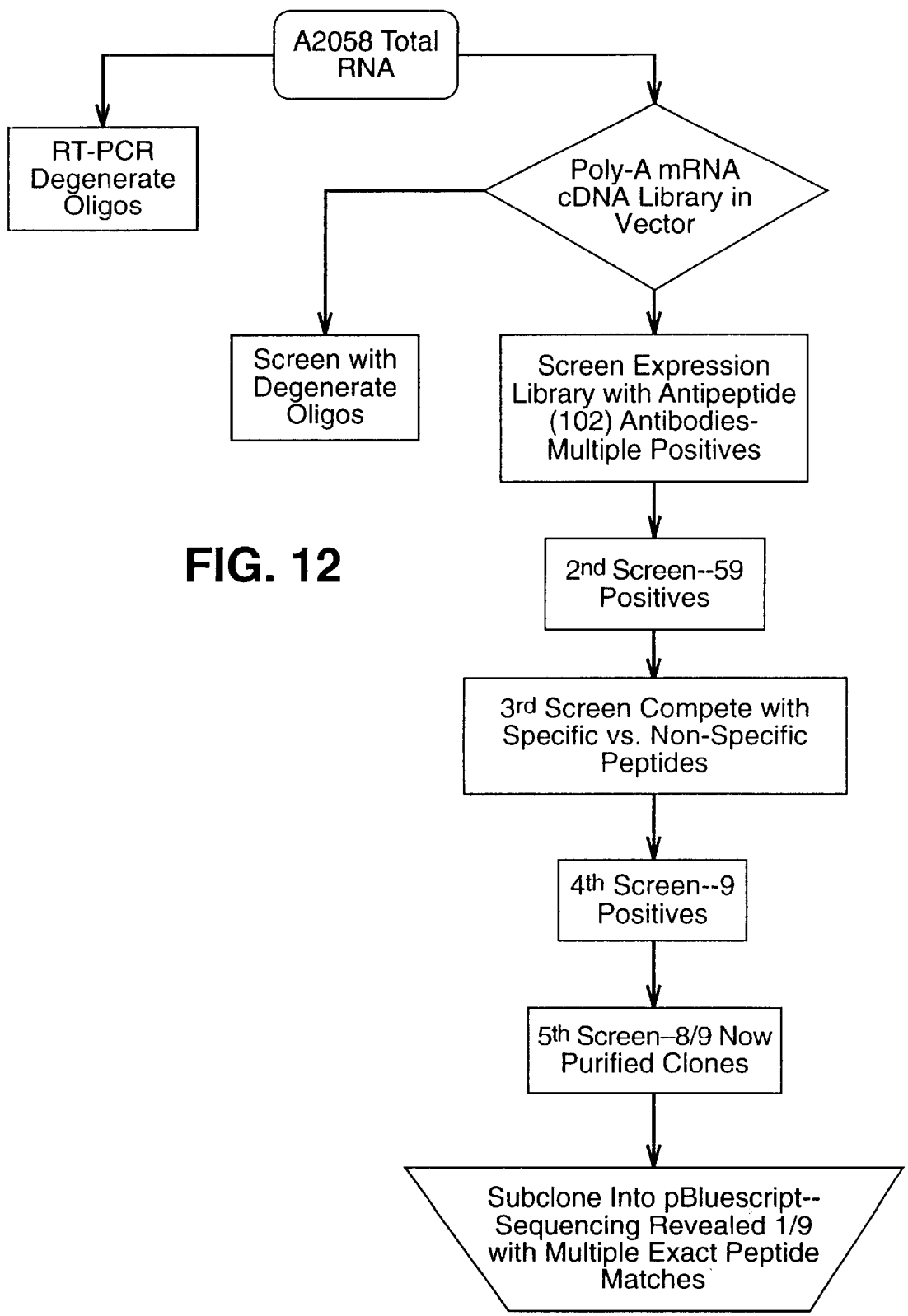
FIG. 12. Cloning Strategy, schematically depicted.

ATX is active in picomolar to nanomolar concentrations and is synthesized in very small concentrations by A2058 cells. As might be expected, the cDNA clone was relatively rare, requiring various strategies and multiple library screenings in order to identify it (FIG. 12). Attempts to utilize degenerate oligonucleotides deduced from known peptide sequences were unsuccessful—whether we used the oligo nucleotides for screening cDNA libraries or for reverse transcription of mRNA followed by amplification with the polymerase chain reaction (RT/PCR). We then utilized an affinity-purified anti-peptide ATX-102 antibodies to screen an A2058 expression library.

These anti-peptide antibodies were generated by methods well established in the art and described previously with slight modification (Wacher, et al., 1990). In brief, the previously identified peptide, ATX-102 (Stracke, et al., 1992), was synthesized on a Biosearch 9600 peptide synthesizer. It was then solubilized in 1X PBS containing 20% (v/v) DMSO and conjugated to the protein carrier, bovine serum albumin (BSA), with glutaraldehyde. For the first injection into New Zealand white rabbits, the BSA-peptide conjugate was emulsified with complete Freund's adjuvant and injected subcutaneously. For subsequent injections, the BSA-peptide conjugate was emulsified with incomplete Freund's adjuvant. The resultant antiserum was heat-inactivated at 56° C. for 30 min. Immunoglobulins were precipitated out in 47% saturated ammonium sulfate, then redissolved and dialyzed into PBS. Antibodies were adsorbed onto peptide-conjugated Affi-Gel 10 resin (made using the BioRad protocol), eluted with 0.1 N acetic acid, and neutralized with 2 M Tris-HCl, pH 8. The resulting affinity-purified antibodies were dialyzed into DPBS, concentrated, aliquotted, and stored at −20° C. The antibodies were found to recognize a 125 kDa protein on immunoblots of partially purified A2058 conditioned medium and to preferentially stain some breast carcinoma cells compared to normal breast using immunohistochemical techniques.

An A2058 cDNA library was prepared by purifying poly-A purified MRNA from the cells then size-selecting MRNA>1000 bp for the preparation of cDNA. The cDNA inserts were placed into λgt11 directionally, using the ProMega cDNA kit using standard methods well-established in the field. LE 392 cells were infected with the λgt11 and plaques were transferred onto nitrocellulose membranes by overnight incubation at 37° C. The antibody was incubated with the membranes in blocking buffer for 2 hr at room temperature, using approximately twice the concentration of antibody which gave a strong response on Western blot analysis. Secondary antibody was goat anti-rabbit immunoglobulin, and the blot was developed colorimetrically with 4-chloro-1-naphthol.

Positive clones were confirmed by antibody competition with specific peptides but not unrelated peptides. Using this technique and multiple subclonings, we obtained a partial cDNA clone of the autotaxin gene, which we called 4C11. The 4C11 insert was removed from λgt11 by restriction enzyme digests and subcloned into pBluescript for sequencing by standard Sanger techniques (Sanger, et al., 1977). The 4C11 clone contained bases, including the poly-adenylated tail and the AATAAA adenylation signal locus, i.e., it contained the 3' terminus of the gene. It also included a 627 base open reading frame. Database analysis of this nucleotide sequence revealed that it is unique. The predicated amino acid sequence for 4C11 is 209 amino acids long with exact matches for 7 previously identified ATX peptides: (ATX-20, ATX-34, ATX-102, ATX-104, ATX-204, ATX-215, and ATX-244).

Example 7

Cloning the 5' Terminus of ATX

Database analysis of the 3' terminus of the ATX gene demonstrated a novel protein. However, we have found an interesting homology that has helped to guide us in exploring its function. ATX had a 45% amino acid identity and a 57% nucleotide identity with PC-1, a marker of B cell activation found on the surface of plasma cells. Using the PC-1 protein sequence as a guide, we found that ATX peptide homologies were scattered throughout the length of the protein. The only exception was the far amino terminus of PC-1, which includes the transmembrane and intracellular domains, and which had no homologies. Knowing approximate localization of the ATX peptides along the length of ATX, we then amplified different segments of ATX by the PCR (FIG. 13). These amplified segments of DNA were then subcloned into plasmids utilizing the TA Cloning kit of ProMega. The PCR amplified DNA could then be sequenced using standard Sanger sequencing techniques (Sanger, et al., 1977).

Cloning of Full length ATX Gene

A reverse transcriptase reaction was performed using total or oligo-(dT) purified RNA from A2058 or N-tera 2D1 cells as template and an anti-sense primer from the 5' end of 4C11 (GCTCAGATAAGGAGGAAAGAG; SEQ ID NO: 55). This was followed by one or two PCR amplification of the resultant cDNA using the commercially available kit from Perkin-Elmer and following manufacturer's directions. These PCR reactions utilized nested antisense primers from 4C11 (GAATCCGTAGGACATCTGCTT; SEQ ID NO: 56 and TGTAGGCCAAACAGTTCTGAC; SEQ ID NO: 57) as well as degenerate, nested sense primers deduced from ATX peptides: ATX-101 (AAYTCIATGCARACIGTITTYGTIG; SEQ ID NO: 58 and TTYGTIGGITAYGGICCIACITYAA; SEQ ID NO: 59), ATX-103 (AAYTAYCTIACIAAYGTIGAYGAYAT; SEQ ID NO: 60 and GAYGAYATIACICTIGTICCIGGIAC; SEQ ID NO: 61), or ATX-224 (TGYTTYGARYTICARGARGCIGGICCICC; SEQ ID NO: 62). The amplified DNA was then purified from a polyacrylamide gel using standard procedures and ligated into the pCR™ plasmid using the TA cloning kit (Invitrogen Corporation) according to manufacturer's directions.

The 5' RACE kit was utilized to extend the 5' end of ATX cDNA using total RNA from N-tera 2D1 as template and previously obtained sequence as primer (GCTGTCTTCAAACACAGC; SEQ ID NO: 63). The 5' end of the A2058 synthesized protein was obtained by using previously obtained sequence as primer (CTGGTGGCTGTAATCCATAGC; SEQ ID NO: 64) in a reverse transcriptase reaction with total A2058 RNA as template, followed by PCR amplification utilizing the 5' end of N-tera 2D1 sequence as sense primer (CGTGAAGGCAAAGAGAACACG; SEQ ID NO: 65) and a nested antisense primer (GCTGTCTTCAAACACAGC; SEQ ID NO: 63). A2058 DNA encoding ATX is set forth in a SEQ ID NO:68 and the amino acid sequence is provided in SEQ ID NO:69.

DNA sequencing: DNA sequencing was performed using dideoxy methodology (Sanger, et al. 1977) and ($^{35}$S)dATP (Du Pont, New England Nuclear).

We have found one region between the 5' end of the 4C111 and the ATX peptide designated ATX-101, also referred to as the "hot spot". This region has been sequenced five times with different sequences found each time. The hot spot appears to be located within the region from approximately nucleotide 1670 to 1815. The consensus sequence is represented by amino acids position 559 through 604. Variations found include DNA sequence that results in single and multiple amino acid insertions. One sequence had a stop codon in this region and may have represented an intron. This region has been found to be variable in forms of ATX.

Example 8

Cloning ATX in a Human Teratocarcinoma Cell Line

The fact that ATX is present in other cancer cells was confirmed by sequence information from N-tera 2D1, a human teratocarcinoma cell line. For these cells, a prepared cDNA library in λgt10 was amplified and the cDNA inserts were extracted. Using oligonucleotide primers based on known A2058 ATX sequence, DNA segments were amplified by PCR. The DNA segments were then subcloned into plasmids and sequenced as for A2058. We have 3104 bp DNA sequence for N-tera ATX (SEQ ID NO:66) and smaller portions thereof. This includes an open reading frame that codes for a putative protein containing 861 amino acids (SEQ ID NO:67) and smaller portions thereof. Like the A2058 ATX, the N-tera 2D1 sequence has homologies for multiple ATX peptides (FIG. 15). Sequence homology between the A2058 and N-tera 2D1 cells is approximately 99%.

Example 9

Cloning 5' End of ATX in Human Normal Liver

The 5' end of ATX has proven difficult to obtain from either tumor cell line to date. Normal human liver mRNA was therefore amplified using the 5' RACE kit (Clontech) with known sequence from A2058 ATX as antisense primer. A DNA segment was obtained and has been sequenced. This segment codes for 979 amino acids, including an initiating methionine (SEQ ID NO: 70). The putative protein sequence also includes a 20 amino acid transmembrane domain which is different from the tumor ATX's (SEQ ID NO:54), as shown in Table 7. Both tumorous forms of ATX apparently lack a transmembrane region and are instead secreted proteins.

TABLE 7

Nucleotide and Amino Acid Sequences Encoding Liver ATX Amino Terminus containing the Transmembrane region Protein Sequence (SEQ ID NO:54)
Met Ala Arg Arg Ser Ser Phe Gln Ser Cys Gln Asp Ile Ser Leu Phe Thr Phe Ala Val Gly Val Asn Ile Cys Leu Gly Phe Thr Ala His Arg Ile Lys Arg Ala Glu Gly Trp

TABLE 7-continued

Nucleotide and Amino Acid Sequences Encoding Liver ATX Amino Terminus containing the Transmembrane region DNA Sequence (SEQ ID NO:53)

ATGGCAAGGA GGAGCTCGTT CCAGTCGTGT CAAGATATAT CCCTGTTCAC

TTTTGCCGTT GGAGTCAATA TCTGCTTAGG ATTCACTGCA CATCGAATTA

AGAGAGCAGA AGGATGG

Example 10

Domains of ATX

Searches of protein databases (Pearson, et. al. 1988) confirmed that the homology between ATX and PC-1 was present throughout the length of the extracellular portion of the molecules (Buckley, et. al., 1990: Funakoshi, et. al. 1992). There is a 45% amino acid identity and a 64% similarity between the 2 protein sequences (FIG. 18). For the cDNA sequence, the identity is ~57%.

These proteins share several interesting properties and domains (FIG. 19). Both have a number of potential N-linked glycosylation sites: four for ATX (Asn54, Asn463, Asn577, Asn859) and nine for PC-1. Both have adjacent somatomedin B domains near the amino end of the extracellular domain. This somatomedin B domain is a cysteine-rich region containing 3 presumed cystine cross-linkages. ATX has 33 Cys residues and PC-1 has 37; 30 of these Cys residues are identical in placement. Both proteins also contain the loop region of an EF hand (Buckley, et. al. 1990; Kretsinger, 1987). In addition, both proteins have a transmembrane/signal peptide region with a short intracellular peptide, common in ectoenzymes (Maroux, 1987). However, the amino acid identity between ATX and PC-1 in the intracellular and transmembrane regions is only 11%.

Finally, both proteins have a region homologous to the bovine intestinal phosphodiesterase enzymatic domain with conversation of the threonine that is thought to act as the intermediate phosphate binding site (Culp, et al. 1985). PC-1 has been demonstrated to have phosphodiesterase type I, nucleotide pyrophosphatase, and threonine-specific kinase enzymatic activities (Rebbe, et al. 1991; Oda, et al. 1991). In order to test whether purified ATX had type I phosphodiesterase activity, samples were incubated with p-nitrophenyl thymidine-5'-monophosphate at pH 8.9 for 30 min. Samples were assayed in a 100 µl volume containing 50 mM Tris-HCl, pH 8.9 and 5 mM p-nitrophenyl thymidine-5'-monophosphate. After a 30 minute incubation at 37° C. the reactions were terminated by addition of 900 ml 0.1 N NaOH and the amount of product formed was determined by reading the absorbance at 410 nm. ATX was found to hydrolyze the p-nitrophenyl thymidine-5'-monophosphate (Razzell, 1963) at a rate of 10 pmol/ng/min, a reaction rate similar to that reported for PC-1 (Oda, et al. 1993).

REFERENCES

Atnip, K. D., et al. (1987) *Biochem. Biophys. Res. Comm.* 146, 996–1002

Buckley, M. F., Loveland, K. A., McKinstry, W. J., Garson, O. M. and Goding, J. W. (1990) *J. Biol. Chem.* 265, 17506–17511

Culp, J. S., Blytt, H. J., Hermodson, M. and Butler, L. G. (1985) *J. Biol. Chem.* 260, 8320–8324

Dennis, J. W., Koch, K., Yousefi, S. and VanderElst, I. (1990) *Cancer Res.* 50, 1867–1872

Funakoshi, I., Kato, H., Horie, K., Yano, T., Hori, Y., Kobayashi, H., Inoue, T., Suzuki, H., Fukui, S., Tsukahara, M., Kajii, T. and Yamashina, I. (1992) *Arch. Biochem. Biophys.* 295, 180–187

Gospodarowicz, D. (1984) *Proc. Natl. Acad. Sci. USA* 81, 6963–6967

Guirguis, R., et al. (1987) *Nature* 329, 261–263

Jouanneau, J., et al. (1991) *Proc. Natl. Acad. Sci. USA* 88, 2893–2897

Kahan, B. W. et al., (1987) *Cancer Res.* 47, 6324–6328

Kretsinger, R. H. (1987) *Cold Spring Harbor Symp. Quant. Bio.* 52, 499–510

Kohler and Milstein, (1975) *Nature* 256:495–497

Kohn, E. C., et al. (1990) *Int. J. Cancer* 46, 287–292

Laemmli U. K. (1970) *Nature* 227, 680–685

Landsteiner, *Specificity of Serological Reactions* (Dover Publications, New York, 1962)

Liotta, L. A., et al. (1986) *Proc. Natl. Acad. Sci. USA* 83, 3302–3306

Liotta, L. A., et al. (1988) *Cancer Surveys* 7, 631–652

Maciag, T., et al. (1984) *Sci.* 225, 932–935

Maroux, S. (1987) In A. J. Kenny and A. J. Turner (eds.) *Mammalian Ectoenzymes*, Elsevier Science Publishers B.V., Amsterdam, The Netherlands, 15–45

McCarthy, J. B., et al. (1984) *J. Cell Biol.* 98, 1474–1480

Microbiology, Hoeber Medical Division (Harper and Row, 1969)

Nabi, I. R., et al. (1990) *Cancer Res.* 50, 409–414

Neuhoff, V., et al. (1988) *Electrophoresis* 9, 255–262

Oda, Y., Kuo, M.-D., Huang, S. S. and Huang, J. S. (1991) *J. Biol. Chem.* 266, 16791–16795

Oda, Y., Kuo, M.-D., Huang, S. S. and Huang, J. S. (1993) *J. Biol. Chem.* 268, 27318–27326

O'Farrell, P. H. (1975) *J. Biol. Chem.* 250, 4007–4021

O'Farrell, P. H., et al. (1977) *Cell* 12, 1133–1142

Ogier-Denis, E., Trugnan, G., Sapin, C., Aubery, M. and Codogno, P. (1990) *J. Biol. Chem.* 265, 5366–5369

Ohnishi, T., et al. (1990) *J. Neurosurg.* 73, 881–888

Pearson, W. R., et al. (1988) *Proc. Natl. Acad. Sci. USA* 85, 2444–2448

Razzell, W. E. (1963) *Methods Enzymol.* 6, 236–258

Rebbe, N.,F., Tong, B. D., Finley, E. M. and Hickman, S. (1991) *Proc. Natl. Acad. Sci. USA* 88, 5192–5196

Rosen, E. M. et al., (1989) *In Vitro Cell Devel. Biol.* 25, 163–173

Rosen, E. M., et al. (1990) *Proc. Soc. Exp. Biol. Med.* 195, 34–43

Ruff, M., et al. (1985) *Clin. Immunol. Immunopath.* 37, 387–396

Sanger, F. et al. (1977) *Proc. National Acad. Sci. USA.* 74, 5463–5467 Schnor, S. L., et al. (1988) *J. Cell Sci.* 90, 391–399

Seftor, R. E. B., Seftor, E. A., Grimes, W. J., Liotta, L. A., Stetler-Stevenson, W. G., Welch, D. R. and Hendrix, M. J. C. (1991) *Melanoma Res.* 1, 43–54

Silletti, S., et al. (1991) *Cancer Res.* 51, 3507–3511

Singer, S. J. and Kupfer, A. (1986) *Ann. Rev. Cell Biol.* 2, 337–365

Stites et al., editors, *Basic and Clinical Immunology*, (Lange Medical Publications, Los Altos, Calif., Fourth edition)

Stoker, M., et al. (1987) *Nature* 327, 239–242

Stone, M, et al. (1989) *A Practical Guide to Protein and Peptide Purification for Microseguencing* (Matsudaira, P.T., ed.) pgs. 33–47, Academic Press, N.Y.

Stracke, M. L. et al., *Biochem. Biophys. Res. Comm.* 153, 1076–1083

Stracke, M. L., et al. (1978) *Biochem. Biophys. Res. Comm.* 146, 339–345

Stracke, M. L., et al. (1987) *Biochem. Biophys. Res. Comm.* 147, 339–345

Stracke, M. L., et al. (1988) *Biochem. Biophys. Res. Comm.* 153, 1076–1083

Tamm, I., et al., (1989) *J. Exp. Med.* 170, 1649–1669

Taraboletti, G., (1987) *J. Cell Biol.* 105, 2409–2415

Todaro, G. J., et al. (1980) *Proc. Natl. Acad. Sci. USA* 77, 5258–5262

Van Snick, J. (1990) *Ann. Rev. Immunol.* 8, 253–278

Wang, J. M., et al. (1990) *Biochem. Biophys. Res. Comm.* 169, 165–170

Watanabe, H., et al. (1990) *J. Cell Biol.* 111, 2097–2108

Watanabe, H., et al. (1991) *J. Biol. Chem.* 266, 13442–13448

Weidner, K. M., et al. (1990) *J. Cell. Biol.* 111, 2097–2108

Williams et al., *Methods in Immunology and Immunochemistry*, Vol. 1 (Academic Press, New York, 1967)

Yoshimura, T. (1987) *Proc. Natl. Acad. Sci. USA* 84, 9233–9237

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the present invention and appended claims.

What is claimed is:

1. A method of purifying an isolated autotaxin polypeptide comprising the steps of:
   i) collecting and concentrating supernatant from cultured cells whereby a first preparation of said polypeptide is produced;
   ii) salt fractionating said first preparation to produce a second polypeptide preparation; and
   isolating said polypeptide from said second preparation so that said polypeptide is obtained in substantially pure form, wherein the polypeptide comprises an amino acid sequence of human autotaxin having phosphodiesterase activity and cell motility-stimulating activity, wherein the polypeptide comprises the amino acid sequence N-Tyr-Met-Arg-Pro-Val-Tyr-Pro-Thr-Lys-Thr-Phe-Pro-Asn-C, residues 201 through 213 of SEQ ID NO: 69.

2. The method of claim 1, wherein said isolating step is effected by column chromatography.

3. An isolated polypeptide comprising an amino acid sequence of human autotaxin having phosphodiesterase activity and cell motility-stimulating activity, wherein the polypeptide comprises the amino acid sequence N-Tyr-Met-Arg-Pro-Val-Tyr-Pro-Thr-Lys-Thr-Phe-Pro-Asn-C, residues 201 through 213 of SEQ ID NO: 69.

4. The isolated polypeptide according to claim 3, wherein the polypeptide comprises 788 amino acid residues.

* * * * *